United States Patent
Barmada et al.

(10) Patent No.: US 10,928,381 B2
(45) Date of Patent: Feb. 23, 2021

(54) IN VITRO METHODS OF MONITORING AUTOPHAGY IN A HUMAN CELL USING A PHOTOCONVERTABLE FLUORESCENT PROTEIN LINKED BIOMARKER

(71) Applicant: The Regents of the University of Michigan, Ann Arbor, MI (US)

(72) Inventors: Sami Barmada, Ann Arbor, MI (US); Nathaniel Safren, Ann Arbor, MI (US); Elizabeth Tank, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 16/288,802

(22) Filed: Feb. 28, 2019

(65) Prior Publication Data

US 2019/0271687 A1 Sep. 5, 2019

Related U.S. Application Data

(60) Provisional application No. 62/637,503, filed on Mar. 2, 2018.

(51) Int. Cl.
| | |
|---|---|
| *G01N 33/50* | (2006.01) |
| *G01N 21/64* | (2006.01) |
| *C07K 14/435* | (2006.01) |
| *C12N 5/071* | (2010.01) |
| *C12N 5/073* | (2010.01) |
| *C12N 15/65* | (2006.01) |

(52) U.S. Cl.
CPC ....... *G01N 33/5005* (2013.01); *C07K 14/435* (2013.01); *C12N 5/0603* (2013.01); *C12N 5/0686* (2013.01); *C12N 15/65* (2013.01); *G01N 21/6428* (2013.01); *C07K 2319/60* (2013.01)

(58) Field of Classification Search
CPC .................................................. C07K 2319/60
USPC ....................................................... 435/69.7
See application file for complete search history.

(56) References Cited

PUBLICATIONS

Al-Chalabi et al., The genetics and neuropathology of amyotrophic lateral sclerosis. Acta Neuropathol. Sep. 2012;124(3):339-52.
Barmada et al., Autophagy induction enhances TDP43 turnover and survival in neuronal ALS models. Nat Chem Biol. Aug. 2014;10(8):677-85.
Berghauser et al., The HDAC Inhibitors Scriptaid and LBH589 Combined with the Oncolytic Virus Delta24-RGD Exert Enhanced Anti-Tumor Efficacy in Patient-Derived Glioblastoma Cells.PLoS One. May 18, 2015;10(5):e0127058.
Brunk et al., Lipofuscin: mechanisms of age-related accumulation and influence on cell function. Free Radic Biol Med. Sep. 1, 2002;33(5):611-9.
Burrell et al., Motor Neuron dysfunction in frontotemporal dementia. Brain. Sep. 2011;134(Pt 9):2582-94.
Cheng et al., Rapamycin Alleviates Pathogenesis of a New *Drosophila* Model of ALS-TDP. J Neurogenet. 2015;29(2-3):59-68.
Cho et al., Analysis of off-target effects of CRISPR/Cas-derived RNA-guided endonucleases and nickases. Genome Res. Jan. 2014;24(1):132-41.
Chudakov et al., Tracking intracellular protein movements using photoswitchable fluorescent proteins PS-CFP2 and Dendra2. Nat Protoc. 2007;2(8):2024-32.
Chudakov et al., Using photoactivatable fluorescent protein Dendra2 to track protein movement. Biotechniques. May 2007;42(5):553, 555, 557 passim.
Ciechanover et al., Degradation of misfolded proteins in neurodegenerative diseases: therapeutic targets and strategies. Exp Mol Med . Mar. 13, 2015;47(3):e147.
Cong et al., Multiplex genome engineering using CRISPR/Cas systems. Science. Feb. 15, 2013;339(6121):819-23.
Cuervo et al., Age-mediated autophagy: roles in disease and aging. Cell Res. Jan. 2014;24(1):92-104.
Cuervo et al., Age-related decline in chaperone-mediated autophagy. J Biol Chem. Oct. 6, 2000;275(40):31505-1.
Cuervo, Autophagy and aging: keeping that old broom working. Trends Genet. Dec. 2008;24(12):604-12.
Dixit et al., SAR and Computer-Aided Drug Design Approaches in the Discovery of Peroxisome Proliferator-Activated Receptor γActivators: A Perspective. J Comput Med 2013;2013:1-38.
Donati et al., Age-related changes in the regulation of autophagic proteolysis in rat isolated hepatocytes. J Gerontol A Biol Sci Med Sci. Jul. 2001;56(7):B288-93.
Hara et al., Suppression of basal autophagy in neural cells causes neurodegenerative disease in mice. Nature. Jun. 15, 2006;441(7095):885-9.
Hetz et al., XBP-1 deficiency in the nervous system protects against amyotrophic lateral sclerosis by increasing autophagy. Genes Dev. Oct. 1, 2009;23(19):2294-306.
Kabeya et al., LC3, a mammalian homologue of yeast Apg8p, is localized in autophagosome membranes after processing. EMBO J. Nov. 1, 2000;19(21):5720-8.
Kamada et al., Tor-mediated induction of autophagy via an Apg1 protein kinase complex. J Cell Biol. Sep. 18, 2000;150(6):1507-13.
Klionsky et al., Guidelines for the use and interpretation of assays for monitoring autophagy (3rd edition). Autophagy. 2016;12(1):1-222.

(Continued)

*Primary Examiner* — Sheridan Swope
(74) *Attorney, Agent, or Firm* — Casimir Jones SC; David W. Staple

(57) ABSTRACT

Provided herein are compositions and systems comprising engineered cells useful for the measurement of autophagy induction, maturation and flux in a high-throughput manner. In particular, provided herein are human embryonic kidney (HEK) cells that express the native autophagy substrate and marker protein LC3 fused to Dendra2, a photoconvertable fluorescent protein; this manipulation allows assessment of all three stages of autophagy (e.g., induction, maturation, and cargo degradation), noninvasively in living cells, without the need for protein overexpression that may interfere with autophagy activity.

4 Claims, 48 Drawing Sheets
(44 of 48 Drawing Sheet(s) Filed in Color)

(56) References Cited

PUBLICATIONS

Komatsu et al., Loss of autophagy in the central nervous system causes neurodegeneration in mice. Nature. Jun. 15, 2006;441(7095):880-4.

Lee et al., Lysosomal Proteolysis Inhibition Selectively Disrupts Axonal Transport of Degradative Organelles and Causes an Alzheimer's-Like Axonal Dystrophy. J Neurosci May 25, 2011;31(21):7817-30.

Li, et al., Autophagy Enhancer Carbamazepine AlleviateAutophagy Enhancer Carbamazepine Alleviates Memory Deficits and Cerebral amyloid-β Pathology in a Mouse Model of Alzheimer's Disease. Curr Alzheimer Res. May 1, 2013;10(4):433-41.

Lillo et al., Amyotrophic lateral sclerosis and frontotemporal dementia: A behavioural and cognitive continuum. Amyotroph Lateral Scler. Jan. 2012;13(1):102-9.

Mahé et al., Graph Kernels for Molecular Structure—Activity Relationship Analysis with Support Vector Machines. J Chem Inf Model. Jul.-Aug. 2005;45(4):939-51.

Malo et al., Statistical practice in high-throughput screening data analysis. Nat Biotechnol. Feb. 2006;24(2):167-75.

Murphy et al., Continuum of Frontal Lobe Impairment in Amyotrophic Lateral Sclerosis. Arch Neurol. Apr. 2007;64(4):530-4.

Neumann et al., Ubiquitinated TDP-43 in frontotemporal lobar degeneration and amyotrophic lateral sclerosis. Science. Oct. 6, 2006;314(5796):130-3.

Niu et al., Support Vector Machine for SAR/QSAR of Phenethyl-Amines. Acta Pharmacol Sin. Jul. 2007;28(7):1075-86.

Pajouhesh et al., Medicinal chemical properties of successful central nervous system drugs. NeuroRx. Oct. 2005;2(4):541-53.

Ran et al., Double nicking by RNA-guided CRISPR Cas9 for enhanced genome editing specificity. Cell. Sep. 12, 2013;154(6):1380-9.

Renna et al., Chemical Inducers of Autophagy That Enhance the Clearance of Mutant Proteins in Neurodegenerative Diseases. J Biol Chem. Apr. 9, 2010;285(15):11061-7.

Renton et al., State of play in amyotrophic lateral sclerosis genetics. Nat Neurosci. Jan. 2014;17(1):17-23.

Rubinsztein et al., of Autophagosome Biogenesis Minireview. Curr Biol. Jan. 10, 2012;22(1):R29-34.

Serra et al., NVP-BEZ235, a Dual PI3K/mTOR Inhibitor, Prevents PI3K Signaling and Inhibits the Growth of Cancer Cells with Activating PI3K Mutations. Cancer Res. Oct. 1, 2008;68(19):8022-30.

Terman, The effect of age on formation and elimination of autophagic vacuoles in mouse hepatocytes. Gerontology. 1995;41 Suppl 2:319-26.

Thoreen et al., An ATP-competitive mammalian target of rapamycin inhibitor reveals rapamycin-resistant functions of mTORC1. J Biol Chem. Mar. 20, 2009;284(12):8023-32.

Tsvetkov et al., A small-molecule scaffold induces autophagy in primary neurons and protects against toxicity in a Huntington disease model. Proc Natl Acad Sci U S A. Sep. 28, 2010;107(39):16982-7.

Tsvetkov et al., proteostasis of polyglutamine varies among neurons and predicts neurodegeneration. Nat Chem Biol. Sep. 2013;9(9):586-92.

Vittorini et al., The age-related accumulation of protein carbonyl in rat liver correlates with the age-related decline in liver proteolytic activities. J Gerontol A Biol Sci Med Sci. Aug. 1999;54(8):B318-23.

Wager et al., Moving beyond Rules: The Development of a Central Nervous System Multiparameter Optimization (CNS MPO) Approach to Enable Alignment of Druglike Properties. ACS Chem Neurosci. Jun. 16, 2010;1(6):435-49.

Wang et al., Autophagy activators rescue and alleviate pathogenesis of a mouse model with proteinopathies of the TAR DNA-binding protein 43. Proc Natl Acad Sci U S A. Sep. 11, 2012;109(37):15024-9.

White et al., Amyotrophic lateral sclerosis. Curr Opin Neurol. Oct. 2016;29(5):557-64.

Wong et al., Integration of clearance mechanisms: the proteasome and autophagy. Cold Spring Harb Perspect Biol. Dec. 2010;2(12):a006734.

Xu et al., for cognitive and behavioural impairment in amyotrophic lateral sclerosis: Frequency of abnormality and effect on survival. J Neurol Sci. May 15, 2017;376:16-23.

Yoshimori et al., Bafilomycin A1, a specific inhibitor of vacuolar-type H(+)-ATPase, inhibits acidification and protein degradation in lysosomes of cultured cells. J Biol Chem. Sep. 15, 1991;266(26):17707-12.

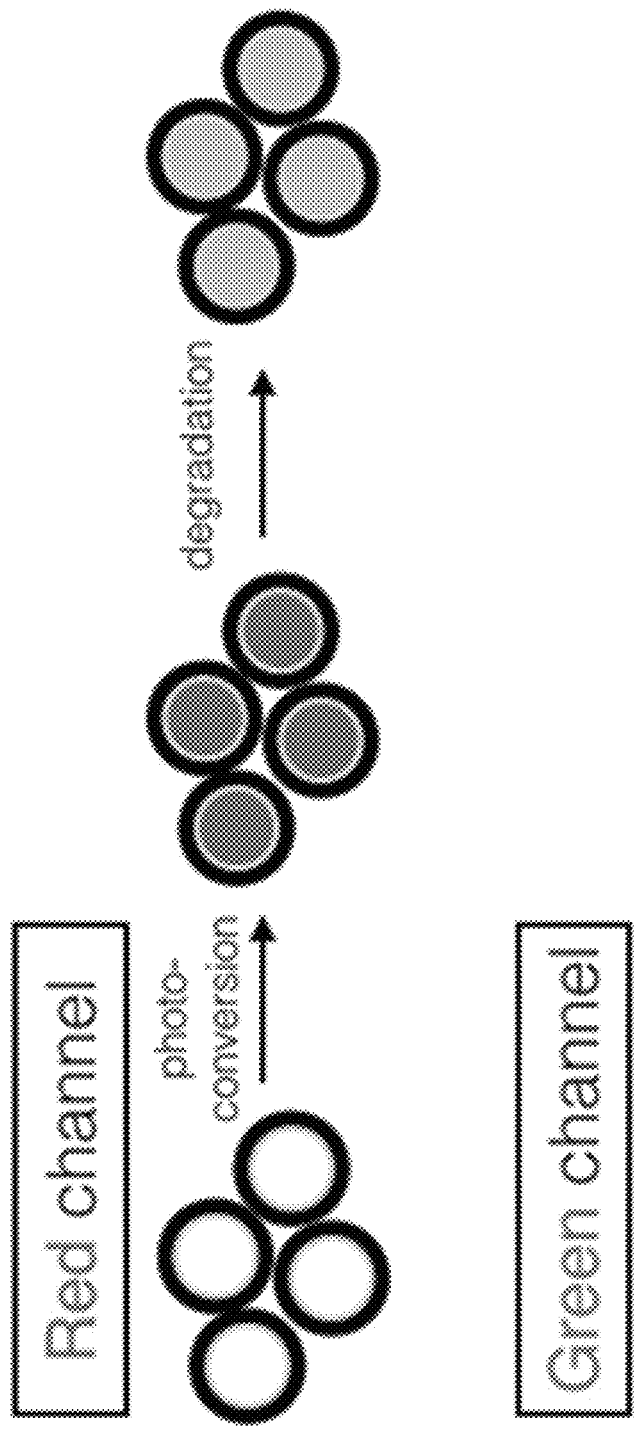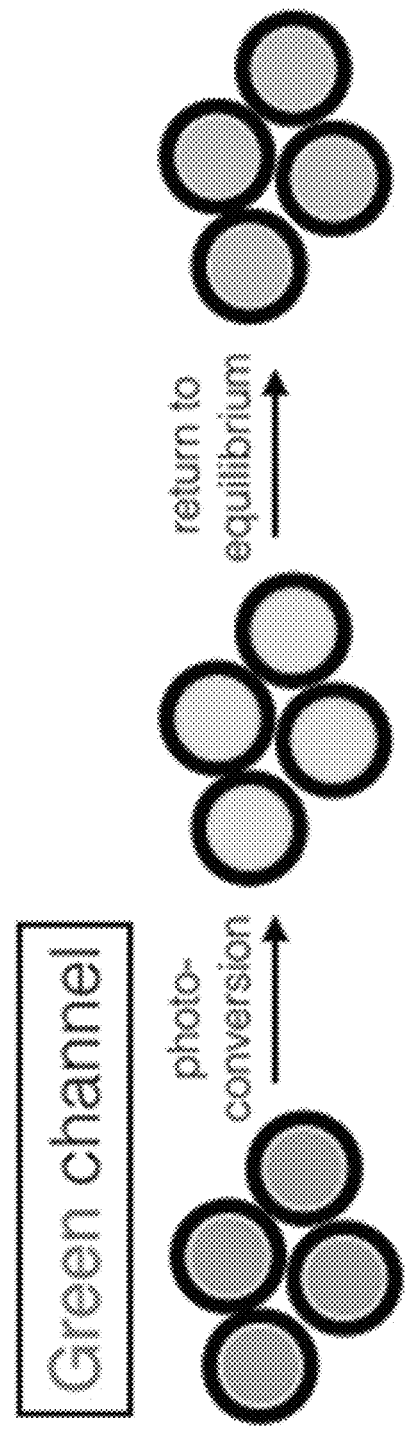

FIG. 3C
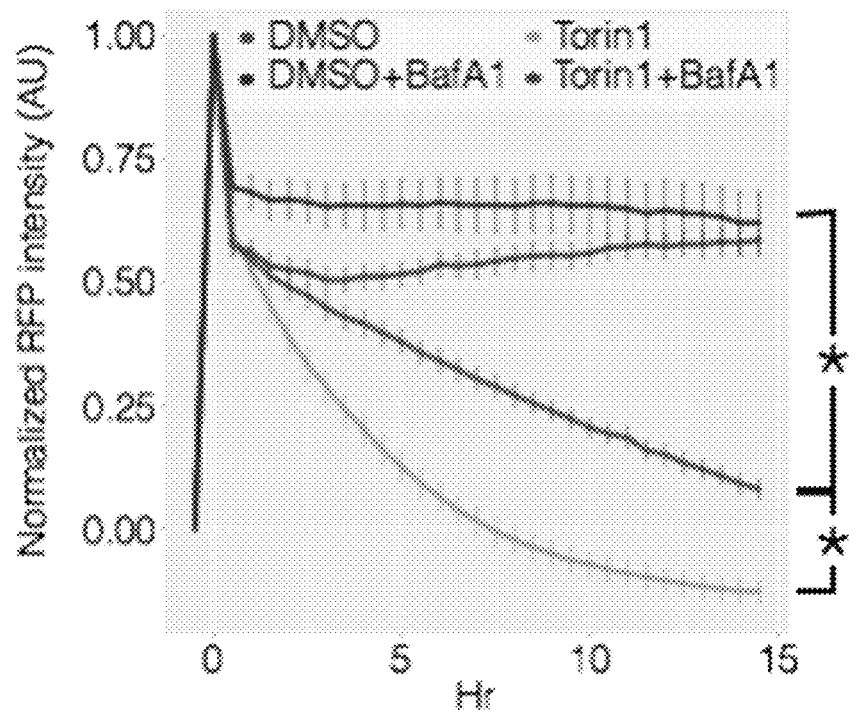
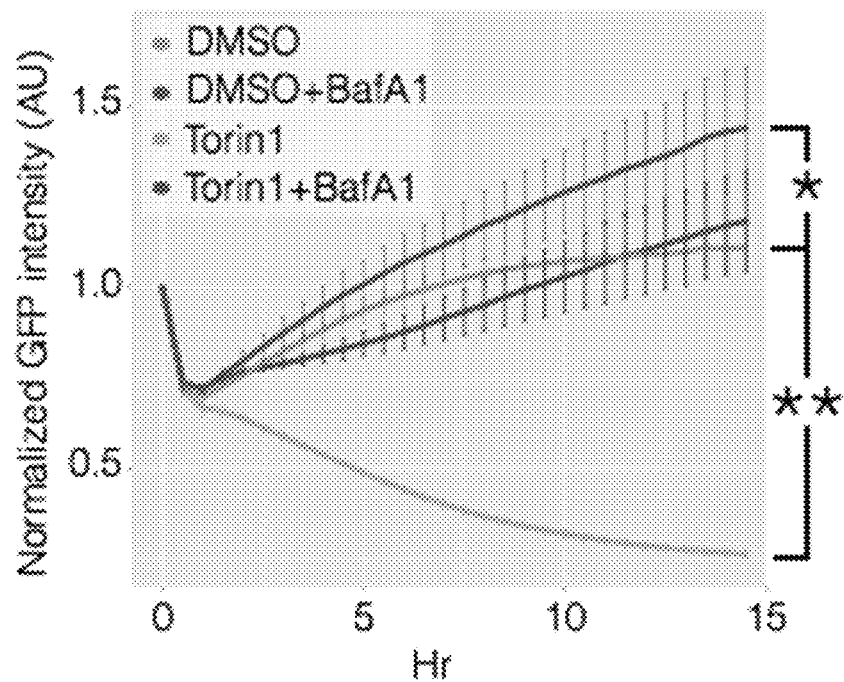
FIG. 3D

FIG. 7B
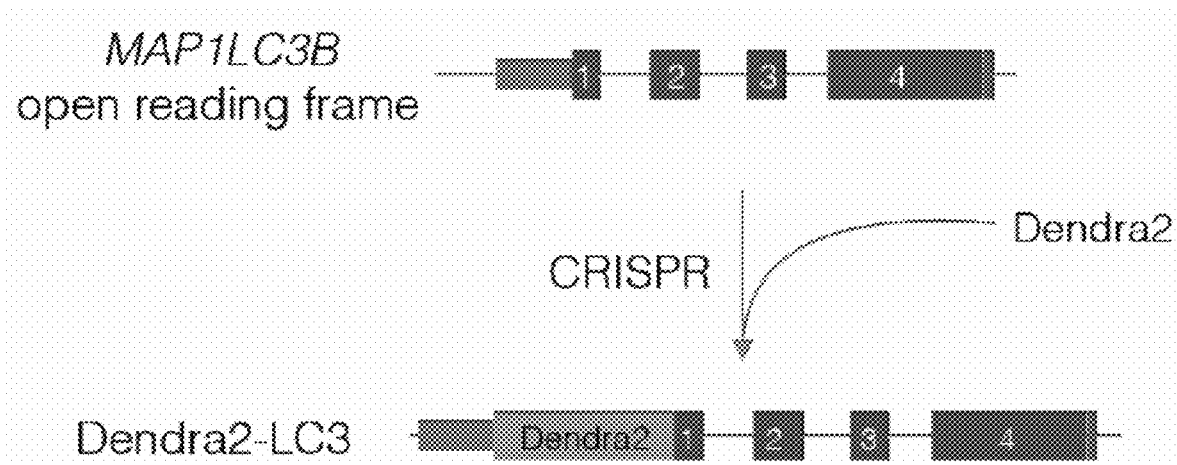
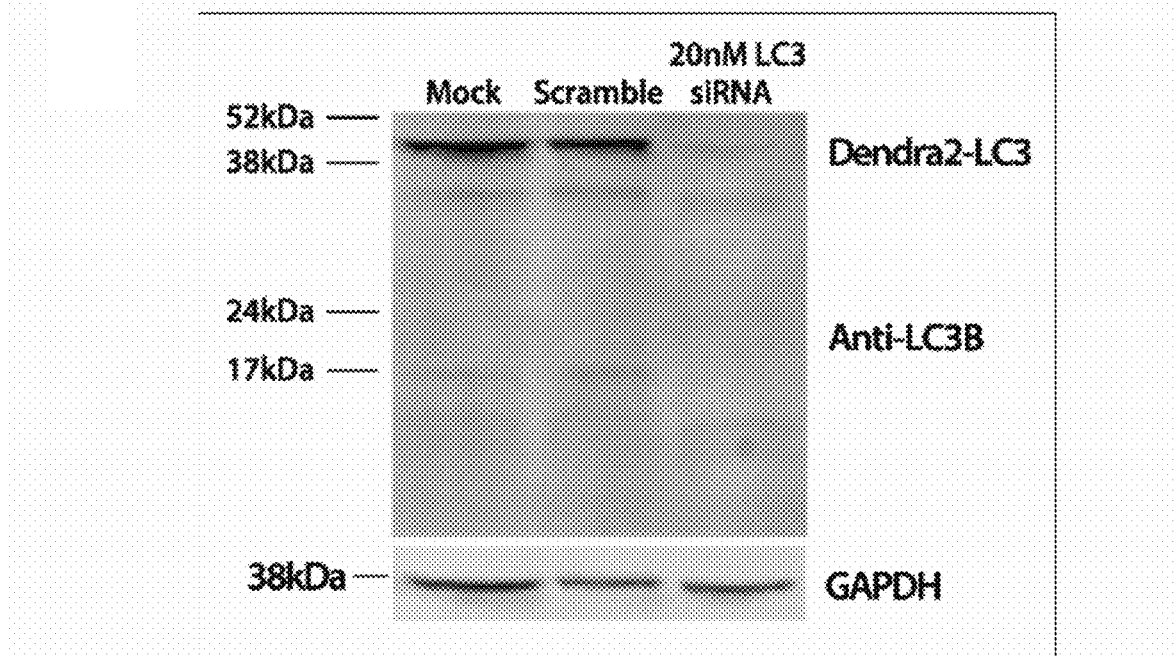
FIG. 7C

FIG. 8B
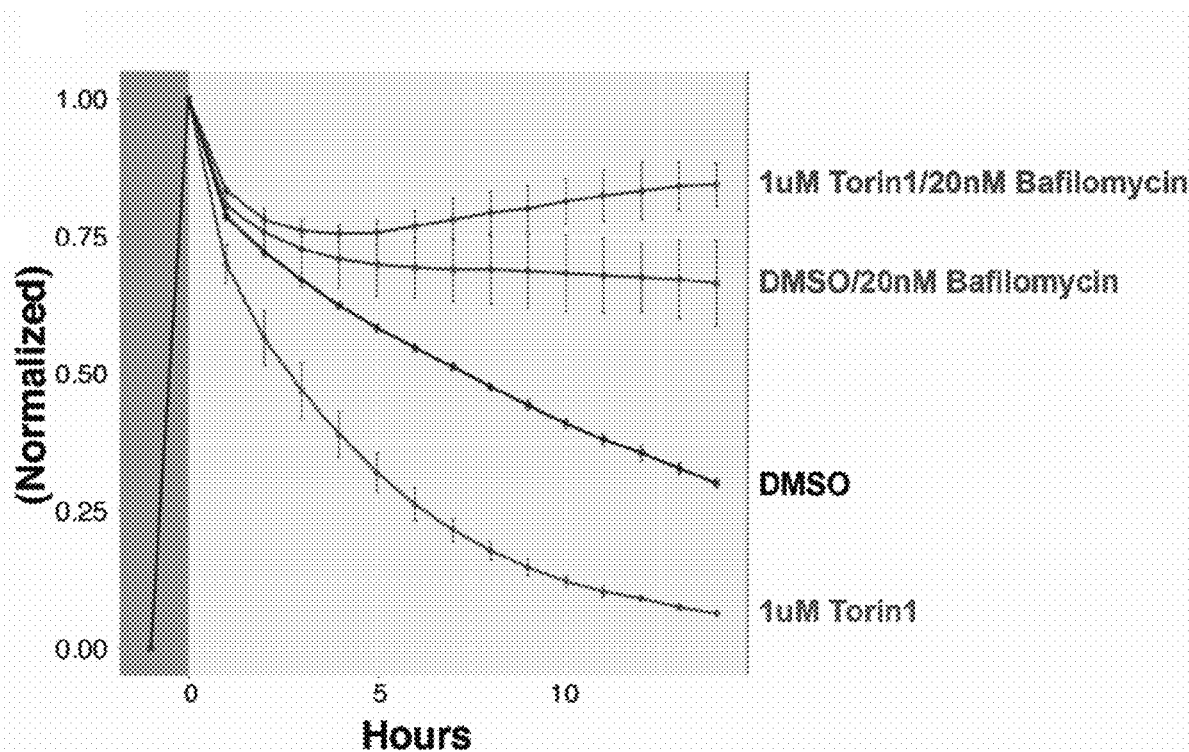
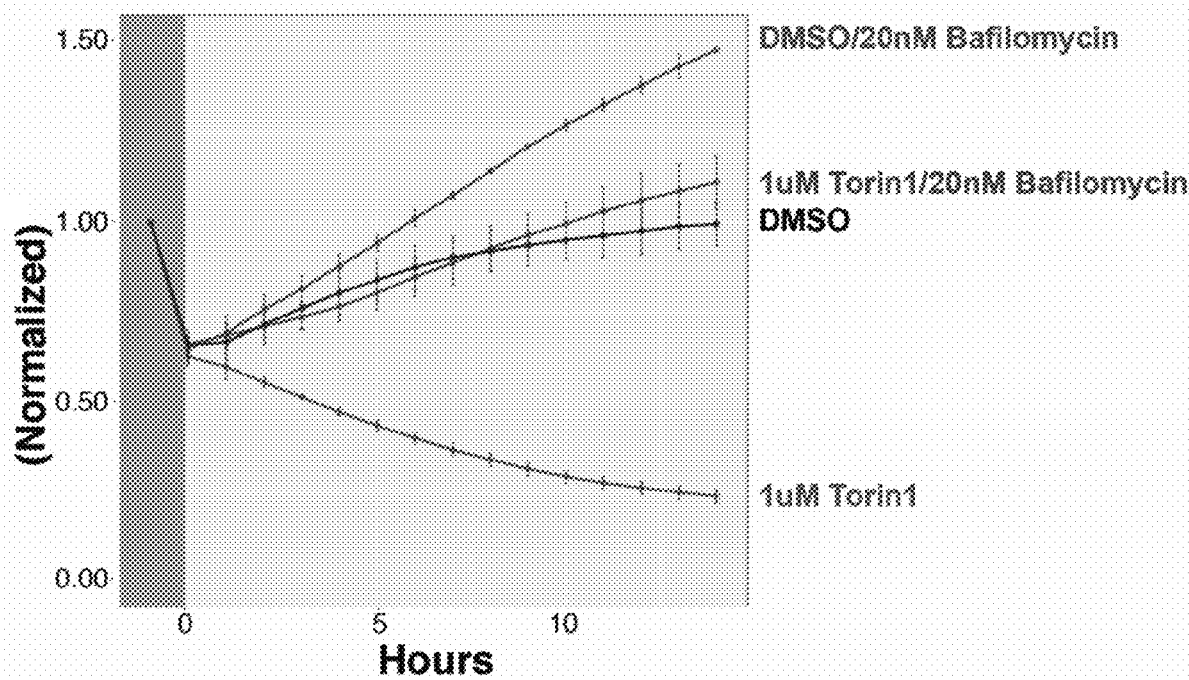
FIG. 8C

FIG. 8D
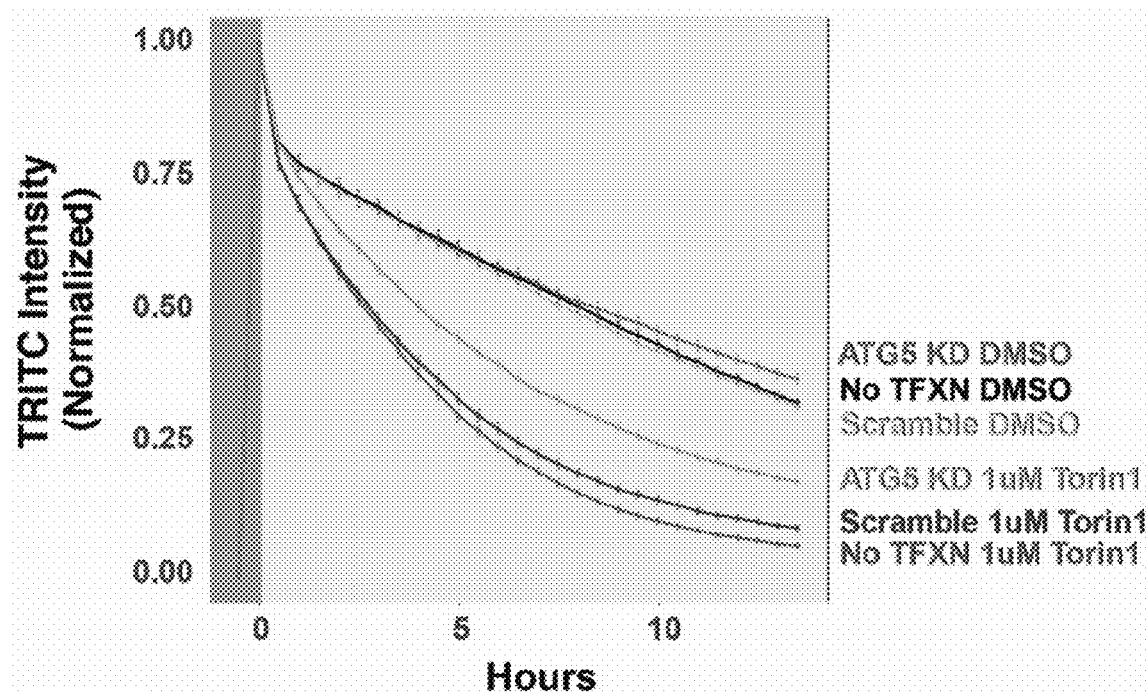
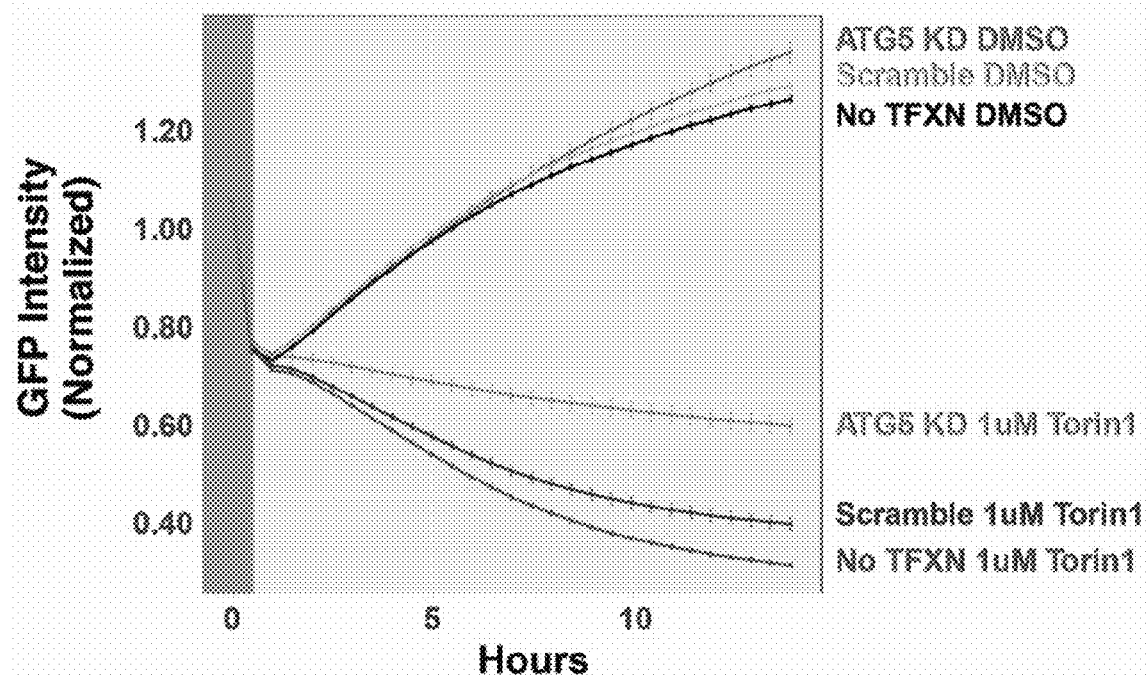
FIG. 8E

FIG. 9B (cont.)

INHIBITORS

| | Cyclohexamide | Niclosamide | Bafilomycin-A1 | Terbinafine | Bim-1 |
|---|---|---|---|---|---|
| 9H/0H RFP | 1.14 | 1.49 | 1.64 | 1.92 | 4.61 |
| 15H/0H GFP | 0.64 | 0.83 | 1.74 | 0.96 | 1.00 |

FIG. 12B

| RANK COMPOUND (after secondary) | GFP 0H / 15H | RFP 0H / 6H | Reordered 0H / 6H | Z-SCORE PRIMARY INIT | PRIMARY CONF | SECONDARY INIT | SECONDARY CONF | FRESH |
|---|---|---|---|---|---|---|---|---|
| 1 CCG-245836 | | | | 3.9 | 5.4 | 36.3 | 28.9 | 9.5 |
| 2 CCG-254522 | | | | 3.3 | 6.4 | 19.7 | 15.2 | 10.3 |
| 3 CCG-45858 | | | | 4.7 | 15.8 | 10.3 | 19.2 | 20.6 |
| 17 CCG-257373 | | | | 3.6 | 3.9 | 3.9 | 3.7 | 4.5 |
| 20 CCG-254794 | | | | 18.1 | 23.2 | 3.4 | 3.6 | 17.8 |

245536

45808

237373

254522

FIG. 13D
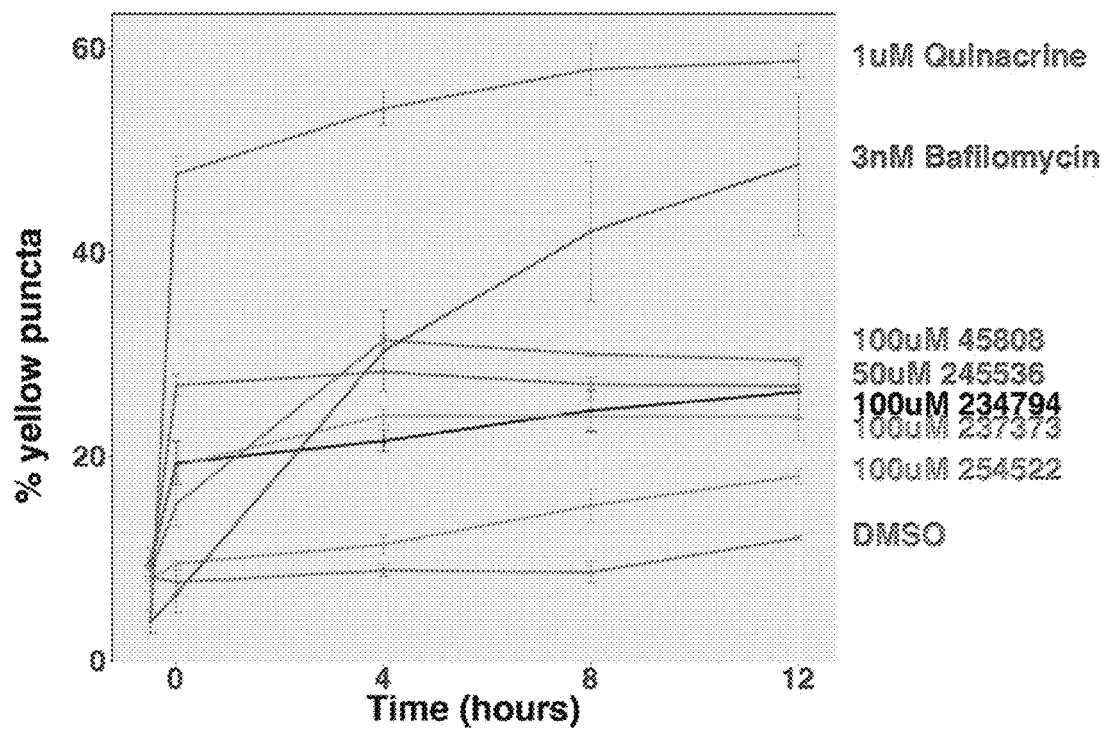
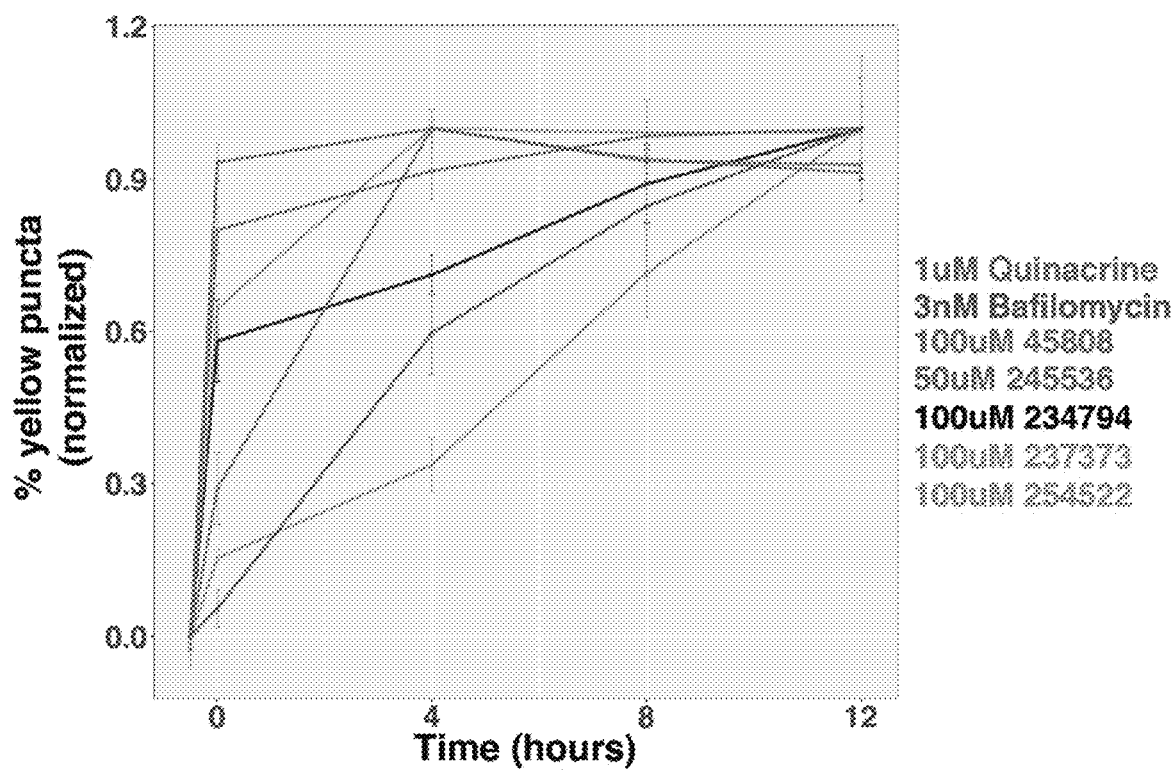
FIG. 13E

IN VITRO METHODS OF MONITORING AUTOPHAGY IN A HUMAN CELL USING A PHOTOCONVERTABLE FLUORESCENT PROTEIN LINKED BIOMARKER

CROSS-REFERENCE TO RELATED APPLICATIONS

The present application claims priority to U.S. Provisional Patent Application No. 62/637,503, filed Mar. 2, 2018, which is incorporated by reference in its entirety.

STATEMENT REGARDING FEDERAL FUNDING

This invention was made with government support under NS097542 awarded by the National Institutes of Health. The government has certain rights in the invention.

FIELD

Provided herein are compositions and systems comprising engineered cells useful for the measurement of autophagy induction, maturation and flux in a high-throughput manner. In particular, provided herein are human embryonic kidney (HEK) cells that express the native autophagy substrate and marker protein LC3 fused to Dendra2, a photoconvertable fluorescent protein; this manipulation allows assessment of all three stages of autophagy (e.g., induction, maturation, and cargo degradation), noninvasively in living cells, without the need for protein overexpression that may interfere with autophagy activity.

BACKGROUND

The formation of protein inclusions is a universal finding in neurodegenerative diseases. This observation suggests a fundamental deficiency in protein homeostasis as an underlying mechanism contributing to neuron loss. Genetic disruption of autophagy, a highly conserved pathway for the degradation of long-lived protein aggregates and organelles, leads to neurodegeneration. Conversely, stimulating autophagy prevents neurodegeneration and ameliorates symptoms of disease in cellular and animal models. Furthermore, age-dependent reductions in autophagic flux may predispose to neurodegeneration in late life, differences in autophagy correlate with the susceptibility of select neuron subtypes to degeneration. These observations indicate that autophagy is broadly neuroprotective, making this pathway an important and potentially rich therapeutic target.

Over a century ago, the French neurologist Jean Louis-Charcot described amyotrophic lateral sclerosis (ALS) as a relentless condition characterized by progressive weakness and muscle loss (Ref. 1; herein incorporated by reference in its entirety). Although ALS patients rarely show frank memory problems, upon closer inspection up to 50% of individuals demonstrate cognitive deficits, including problems with language, personality and behavior, consistent with frontotemporal dementia (FTD) (Refs. 2-4; herein incorporated by reference in their entireties). Conversely, up to ⅓ of FTD patients exhibit motor neuron disease indistinguishable from ALS (Ref. 5; herein incorporated by reference in its entirety), providing strong evidence of a link between the two conditions. In support of such a connection, most patients with ALS and FTD demonstrate neuronal inclusions rich in the RNA binding protein TDP43 (Refs. 6-7; herein incorporated by reference in its entirety), and mutations in several shared genes lead to familial forms of both disorders (Refs. 8-9; herein incorporated by reference in their entireties). To date, there are no effective disease modifying treatments for either ALS or FTD. Even so, the convergent clinical and pathological observations suggest that therapies developed for one disorder may also be effective for the other.

The accumulation of TDP43 deposits in ALS and FTD highlights a fundamental deficiency in protein homeostasis contributing to neuron loss in these disorders. Genetic disruption of autophagy, a highly conserved pathway for the degradation of long-lived protein aggregates and organelles, leads to neurodegeneration (Refs. 10-12; herein incorporated by reference in their entireties). Likewise, stimulating autophagy extends neuronal survival and ameliorates symptoms of disease in cellular and animal models of ALS, FTD and related disorders (Ref.s 13-17; herein incorporated by reference in their entireties). Age-dependent reductions in autophagic flux may predispose to neurodegeneration in late life (Refs. 18-22; herein incorporated by reference in their entireties). These observations indicate that autophagy is broadly neuroprotective in ALS and FTD, making this pathway an important and potentially rich therapeutic target.

SUMMARY

Provided herein are compositions and systems comprising engineered cells useful for the measurement of autophagy induction, maturation and flux in a high-throughput manner. In particular, provided herein are human embryonic kidney (HEK) cells that express the native autophagy substrate and marker protein LC3 fused to Dendra2, a photoconvertable fluorescent protein; this manipulation allows assessment of all three stages of autophagy (e.g., induction, maturation, and cargo degradation), noninvasively in living cells, without the need for protein overexpression that may interfere with autophagy activity.

In some embodiments, provided herein are polypeptides comprising an autophagy biomarker fused to a photoconvertable fluorescent protein (fcFP). In some embodiments, the autophagy biomarker is selected from the group consisting of microtubule-associated proteins 1A/1B light chain 3B (LC3), p62/sequestosome 1, and Beclin 1. In some embodiments, the autophagy biomarker is LC3. In some embodiments, the fcFP is an irreversible fcFP. In some embodiments, the fcFP is selected from the group consisting of PAGFP, PS-CFP, PS-CFP2, PAmRFP1-1, PAmRFP1-2, PAmRFP1-3, PAmCherry1, PAmCherry2, PAmCherry3, KFP, Kaede, mEosFP, mEos2, KikGR, mKikGR, and IrisFP. In some embodiments, the fcFP is a reversible fcFP. In some embodiments, the fcFP is selected from the group consisting of Dronpa, Dendra, Dendra2, and IrisFP. In some embodiments, the fcFP is Dendra2. In some embodiments, the fcFP and the autophagy biomarker are directly fused. In some embodiments, the fcFP and the autophagy biomarker are fused via a linker segment. In some embodiments, the autophagy biomarker is microtubule-associated proteins 1A/1B light chain 3B (LC3) and the fcFP is Dendra2.

In some embodiments, provided herein are nucleic acids encoding the autophagy biomarker/fcFP fusions described herein.

In some embodiments, provided herein are vectors comprising nucleic acids encoding the autophagy biomarker/fcFP fusions described herein. In some embodiments, vectors further comprise one or more expression elements (e.g. IRIS, promoter, etc.).

In some embodiments, provided herein are cells comprising nucleic acids encoding the autophagy biomarker/fcFP fusions described herein. In some embodiments, the nucleic acid is stably incorporated into the genetic material of the cell. In some embodiments, the cell expresses the polypeptide from the nucleic acid. In some embodiments, provided herein are cells comprising the autophagy biomarker/fcFP fusions described herein. In some embodiments, the cell is a mammalian cell. In some embodiments, the cell is a human cell. In some embodiments, the cell is a human embryonic kidney (HEK) cells.

In some embodiments, provided herein are methods of monitoring autophagy in a cell, the cell expressing a polypeptide comprising an autophagy biomarker fused to a photoconvertable fluorescent protein (fcFP), comprising: (a) exposing the cell to an appropriate wavelength of light to photoconvert the fcFP; and (b) monitoring a pre-conversion and/or post-conversion emission wavelength of the fcFP over time. In some embodiments, the autophagy biomarker is selected from the group consisting of microtubule-associated proteins 1A/1B light chain 3B (LC3), p62/sequestosome 1, and Beclin 1. In some embodiments, the autophagy biomarker is LC3. In some embodiments, the fcFP is an irreversible fcFP. In some embodiments, the fcFP is selected from the group consisting of PAGFP, PS-CFP, PS-CFP2, PAmRFP1-1, PAmRFP1-2, PAmRFP1-3, PAmCherry1, PAmCherry2, PAmCherry3, KFP, Kaede, mEosFP, mEos2, KikGR, mKikGR, and IrisFP. In some embodiments, the fcFP is a reversible fcFP. In some embodiments, the fcFP is selected from the group consisting of Dronpa, Dendra, Dendra2, and IrisFP. In some embodiments, the fcFP is Dendra2. In some embodiments, the autophagy biomarker is microtubule-associated proteins 1A/1B light chain 3B (LC3) and the fcFP is Dendra2. In some embodiments, time-dependent reduction in emission at the post-conversion wavelength correlates to autophagy flux for the cell. In some embodiments, time-dependent increase in emission at the pre-conversion wavelength correlates to activity of the autophagy pathway. In some embodiments, pre-conversion and/or post-conversion emission is monitored at discrete time points. In some embodiments, pre-conversion and/or post-conversion emission is monitored in real-time.

In some embodiments, provided herein are methods for screening for modulators of autophagy, comprising: (a) providing a cell expressing a polypeptide comprising an autophagy biomarker fused to a photoconvertable fluorescent protein (fcFP); (b) exposing the cell to an appropriate wavelength of light to photoconvert the fcFP; (c) contacting the cell with a candidate autophagy modulator; (d) monitoring a pre-conversion and/or post-conversion emission wavelength of the fcFP over time; and (e) comparing the pre-conversion and/or post-conversion emission over time with pre-conversion and/or post-conversion emission of a control cell not exposed to the candidate autophagy modulator. In some embodiments, the screening is performed in a high-throughput manner.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-D. Optical pulse labeling for assessing autophagy flux. (FIG. 1A) Cartoon depicting the three phases of autophagy. (FIG. 1B) Schematic of optical pulse labeling (OPL). Dendra2 is fused to LC3, and photoconverted with blue (405 nm) light. Photoconverted (red) Dendra2-LC3 is degraded within mature autophagosomes. Autophagy flux is assessed by measuring the loss of photoconverted (Dendra2-LC3 (FIG. 1C) or the return of native Dendra2-LC3 (FIG. 1D).

(FIG. 2A) endra2 was inserted into the MAP1LC3B locus using CRISPR/Cas9. (FIG. 2B) Photoconversion of Dendra2-LC3 in modified HEK cells. Scale bar, 50 Dendra2-LC3 (*) knockdown with MAP1LC3B siRNA, as visualized by western blot (FIG. 2C) and native GFP fluorescence (FIG. 2D). IB, immunoblot.

FIGS. 3A-E. Development of an in cellulo, high-throughput autophagy screen. (FIG. 3A) Upon nutrient deprivation, Dendra2-LC3 HEK cells show reduced diffuse GFP signal but more puncta (arrows). (FIG. 3B) Fluphenazine (FPZ, 0.5 µM) and torin1 (1 µM) have similar effects. (FIG. 3C) As measured by the drop in photoconverted Dendra2-LC3, Torin1 significantly accelerates Dendra2-LC3 degradation, indicative of enhanced autophagic flux. BafilomycinA1 (BafA1), an inhibitor of autophagosome maturation, blocks induction by torin1. (FIG. 3D) Assessment of native (green) Dendra2-LC3 return to equilibrium after photoconversion confirms the effects of torin1 and BafA1 on autophagy flux, emphasizing the difference between torin1 and vehicle (DMSO) control. (FIG. 3E) Using the normalized GFP (T15/T0) ratio, the calculated Z' in a 384-well format is 0.56. The threshold values for identification of autophagy inhibitors and inducers in this assay are 3SD above and below the mean for vehicle (DMSO) control. * $p<0.05$; ** $p<0.0001$, one-way ANOVA with Dunnett's post-test.

FIGS. 7A-D. Creation of an exemplary stable cell line serving as a reporter for autophagic flux. (FIG. 7A) Illustration depicting the use of optical pulse labeling to measure autophagic flux. Dendra2 is a photoconvertible protein that upon exposure to 405 nm light irreversibly shifts its fluorescence from green to red. As photoconverted Dendra2-LC3 is degraded in lysosomes red fluorescent intensity decreases. The time dependent decay of red signal serves as an estimate of autophagic flux without the confound of new LC3 synthesis, which is green. (FIG. 7B) Schematic of strategy for tagging native LC3 using CRISPR/Cas9 genome editing. In HEK293 cells Dendra2 was introduced into the MAP1LC3B locus upstream of exon 1 creating an N-terminal fusion protein. (FIG. 7C) Western blot confirming the successful labeling of LC3 with Dendra2. Dendra2-LC3 stable HEK cells were treated with 20 nM scramble or LC3 siRNA. Lysates were collected after 48 hours and immunoblotted with an LC3 antibody. LC3 runs at a molecular weight corresponding to the predicted size of Dendra2-LC3 and this band disappears upon siRNA knockdown of LC3. GAPDH lane serves as a loading control. (FIG. 7D) Dendra2-LC3 reporter line imaged in GFP channel 48 hours after treatment with either scramble or siRNA targeting LC3.

FIGS. 8A-E. Time dependent decay of Dendra2-LC3 as an assay of autophagic flux. (FIG. 8A) Dendra2-LC3 reporter cells were imaged prior to photoconversion to measure background TRITC intensity. Immediately following photoconversion with a 5 second pulse of 405 nM light, cells were treated with DMSO, 1 uM Torin1, or 10 nM Bafilomycin-A1 and then were subsequently imaged at the indicated time points. Images are psuedocolored to better highlight intensity differences. (FIGS. 8B-E) Time dependent changes in photoconverted Dendra2-LC3 fluorescence in the TRITC (FIGS. 8B, D) and GFP (FIGS. 8C, E) channels. Gray boxes represent the pre and post-photoconversion time points. TRITC intensity values are normalized, setting the background intensity prior to conversion to 0 and the post-conversion value to 1. GFP values are normalized to the pre-conversion intensity. Error bars represent the SEM from three replicate experiments. (FIG. 8B) Treatment with 1 uM Torin1 accelerates decay reflecting enhanced autophagic degradation of the reporter, while treatment with bafilomycin extends it through reporter stabilization. (FIG. 8C) Following photoconversion there is a 40% drop in GFP intensity. As new Dendra2-LC3 is synthesized, GFP levels return to pre-photoconversion levels over the span of 13.5 hours. However, this return is prevented by accelerating flux with 1 uM Torin1 treatment. Genetic inhibition of autophagy via partial knockdown of ATG5 attenuates the effects of the autophagy inducer Torin1 in both the TRITC (FIG. 8D) and GFP (FIG. 8E) channels. Cells were transfected with 20 nM ATG5 siRNA two days prior to imaging.

(FIG. 9A) An unbiased screen of the Enzo Autophagy compound library identified several known autophagy compounds as hits providing construct validity to the assay. Rapamycin, NVP-BEZ235 and AKT inhibitor X, were among the compounds appropriately identified as enhancers while Bafilomycin registered as an inhibitor. Several drugs are highlighted for their failure to markedly affect flux including trehalose and carbamazepine. Cells were imaged in RFP to measure background fluorescence, then photoconverted with a 4 second DAPI exposure and immediately imaged again to establish the postconversion intensity. Drugs from the Enzo Autophagy library were added at a concentration of 10 uM via a robotic liquid handler. 9 hours later the cells were imaged again in order to assess the efficacy of the drugs. Hits were defined as follows: enhancer: $[Sample_{9H\ RFP/OH\ RFP}] < [DMSO_{9H\ RFP/OH\ RFP} - 3SD_{DMSO}]$, inhibitor: $[Sample_{9H\ RFP/OH\ RFP}] > [DMSO_{9H\ RFP/OH\ RFP}\ 3SD_{DMSO}]$. Z'=0.79 (FIG. 9B) Images highlighting exemplary hits, as wells as drugs that failed to show an effect. Imaging of the compound library was repeated in GFP. Intensity values are reported 15 hours after drug treatment. (FIG. 9C) The reduction in Dendra2-LC3 half-life observed upon treatment of autophagic flux enhancers is attenuated with partial knockdown of ATG5. Cells were transfected with 20 nM ATG5 siRNA 2 days prior to imaging. Error bars represent SEM from three replicate experiments.

(FIG. 10A) Dendra2-LC3 HEK cells were treated with increasing concentrations of Torin1 and Bafilomycin. Images are pseudocolored to accentuate intensity variations. (FIG. 10B) Decay of Dendra2-LC3 by Torin1 increased in a dose dependent manner, demonstrating the ability of the assay to detect small changes in autophagic flux. (FIG. 10C) These changes are more apparent in the GFP channel highlighting its superior sensitivity. A similar, tunable response can be seen with the lysosomal inhibitor bafilomycin in both the RFP (FIG. 10D) and GFP (FIG. 10E) channels. For FIG. 10B-D error bars represent SEM from 8 replicate wells. (FIG. 10F) Dose response curves for torin1, NVP-BEZ235, rapamycin, and bafilomycin. For autophagy enhancers, the greatest reduction in RFP intensity 7 hours after drug treatment relative to DMSO was set to 1 and the lowest reduction set to 0. Conversely for Bafilomycin, the maximum effect represents the greatest increase in RFP intensity 7 hours after drug treatment. Effects in the GFP channel are reported the same way but at 14 hours after drug treatment. Concentration is plotted in nM on a log(2) scale. At each concentration at least three replicate wells are reported for each channel shown as colored dots. EC50 and IC50 values are reported along the x-axis for both RFP and GFP.

(FIG. 11A) "90/10" experiment validating the measurement of Dendra-LC3 in the GFP channels as a primary assay. In three replicate experiments 320 wells of a 384w plate were treated with DMSO and 32 were treated with 1 uM Torin1. Plates were imaged in GFP immediately before, and 15 hours after drug treatment. Enhancers are defined as: $[Sample_{15H\ GFP/OH\ GFP}] < [DMSO_{15H\ GFP/OH\ GFP} - 3SD_{DMSO}]$. and inhibitors as: $[Sample_{15H\ GFP/OH\ GFP}] > [DMSO_{15H\ GFP/OH\ GFP}\ 3SD_{DMSO}]$. Z'=0.52±0.04 in three experiments. (FIG. 11B) Schematic illustrating sequential screening hierarchy. (FIG. 11C) Primary screen of the Prestwick drug library. Z-score is calculated as number of $SD_{DMSO}$ greater or less than mean $DMSO_{15H/OH}$. Whether a drug result in a significant change in flux, toxicity, or puncta is indicated by its color and size according to the figure key. A break in the Y-axis was made in order to fit in the compound quinacrine. (FIG. 11D) The time dependent decay in red fluorescent intensity of Dendra2-LC3 was used as a secondary screen of the non-toxic hits from the primary screen. Hits were defined as follows: enhancer= $[Sample_{9H\ RFP/OH\ RFP}] < [DMSO_{9H\ RFP/OH\ RFP} - 3SD_{DMSO}]$, inhibitor=$[Sample_{9H\ RFP/OH\ RFP}] > [DMSO_{9H\ RFP/OH\ RFP} + 3SD_{DMSO}]$. Error bars represent the SEM from 6 images comprised of two images per well of three replicate wells.

FIGS. 12A-B. High throughput screen identifies autophagy inhibitors. (FIG. 12A) The primary screen was performed using the Maybridge 24K library, which consists of 24,000 compounds spanning wide chemical space. As in the primary screen in FIG. 11, enhancers are defined as: $[Sample_{15H\ GFP/OH\ GFP}] < [DMSO_{15H\ GFP/OH\ GFP} - 3SD_{DMSO}]$ and inhibitors as: $[Sample_{15H\ GFP/OH\ GFP}] > [DMSO_{15H\ GFP/OH\ GFP} + 3SD_{DMSO}]$. The magnitude of effect for each compound was normalized to that of 1 uM Torin1's ability to accelerate the clearance of Dendra2-LC3. Non-toxic compounds that passed the primary screen were then further filtered in a series of counter screens including a primary screen re-test, a secondary screen, secondary screen retest, and another secondary screen re-test using the compound produced by a different distributor. Those compounds that passed every screen are presented in black. The color and size of the failed compounds denotes what step they were screened out at, in accordance with the figure key. (FIG. 12B) Representative images of the primary screen, secondary screen, and secondary screen re-test with reordered compounds for the 5 confirmed autophagy inhibitors. Z-scores are reported for each screening phase. Compounds are ranked based on the magnitude of their effect in the initial secondary screen.

FIG. 13A-E. Validation of novel autophagy inhibitors with an independent measure of autophagic flux. (FIG. 13A) Tandem reporter (RFP-GFP-LC3) HeLa cells treated with the indicated compounds and imaged after 12 hours in RFP (middle panels) GFP (bottom panels). Composite images are displayed on the top row. Concentrations used correspond to the lowest dose resulting in the maximum degree of colocalization between GFP and RFP puncta as calculated in (B). These are: 3 nM Bafilomycin, 1 uM Quinacrine, 50 uM 245536, and 100 uM of 254522, 45808, 234794, and 237373. (Scale bar: 50 µm) (FIG. 13B) The percentage of RFP positive puncta that are also GFP positive in tandem reporter HeLa cells was analyzed using Cell Profiler. First GFP (1a) and RFP (1b) images of the same field of cells are uploaded into Cell Profiler. Using the GFP images, nuclei are identified (2a-green outlines) and a nuclear mask (2b) is generated. Nuclei that do not pass size or intensity thresholds, or are on the edges of an image, are excluded (2a-purple outlines). Cellular boundries are identified (3a-purple outlines) and a cellular mask is created. The nuclear mask is subtracted from the cellular mask to produce a cytoplasmic mask (3b). Only puncta within this mask will be evaluated in subsequent steps. Image processing is performed to selectively enhance the intensity of cytoplasmic puncta in both the GFP (4a) and RFP (5a) images and masks corresponding to GFP positive puncta (4b) and RFP positive puncta (5b) are made. Finally, RFP puncta that overlap with GFP puncta are identified (6b). This pipeline allows for the accurate identification of GFP+/RFP+ autophaosomes that appear as yellow puncta in panel 6a. (Scale bar: 50 um). (FIG. 13C) Dose response curves showing degree of autophagy inhibition with increasing drug concentrations. Effect represents the % of RFP puncta that are GFP positive, where the greatest and lowest % are set to 1.0 and 0, respectively. Concentration is plotted on a log 2 scale. Dots represent replicate wells. (FIG. 13D) Tandem reporter HeLa cells were imaged once prior to drug treatment and then treated with the lowest dose that produced the maximum response as calculated in (FIG. 13C) and imaged immediately after. Cells were subsequent imaged again at 4 hours, 8 hours, and 12 hours. Each point is calculated by taking the mean % of (GFP+/RFP+ puncta)/(RFP+) from 8 technical replicates. Error bars represent the SEM from three replicate experiments. (FIG. 13E) % (RFP+/GFP+ puncta/RFP+ puncta) as depicted in (FIG. 13D) but normalized in order to emphasize the rate at which each drug works. Error bars represent SEM for three replicate experiments.

(FIG. 14A) Measuring basal autophagy in primary neurons. Mixed rat spinal neurons were transfected on DIV 4 with Dendra2-LC3. On the day following transfection neurons were imaged once to measure baseline levels of GFP and background levels of TRITC (DAY 1 pre). Next a brief pulse (200-500 ms) of 405 nm light was applied to photoconvert Dendra2-LC3. Over the next two days thousands of neurons were longitudinally imaged in order to track their time-dependent loss of red fluorescence. (Scale bars=100 µm) (FIG. 14B) Schematic depicting how rates of basal autophagy are related to neuronal survival. For each cell a Dendra2-LC3 half-life is calculated as explained in panel A. Next in stage 2, each of these neurons are prospectively tracked using automated fluorescence microscopy to determine their time of death (red number and corresponding arrow). Combining these two measurements makes provides prediction of survival based on a neuron's rate of basal autophagy. Only cells that live the entire phase of stage 1 are included in analysis. (FIG. 14C) Penalized splines modeling the relationship between Dendra2-LC3 half-life and survival in both primary rat cortical and spinal neurons. For both neuronal populations there is a strong linear relationship (cortical: $p=3.4E-9$, spinal $p=1.1E-6$) between half-life and survival. In both instances neurons with shorter Dendra2-LC3 half-lives, and therefore higher rates of basal autophagy, lived longer. Each hash mark represents an individual neuron. Grey dotted lines mark 95% confidence intervals. (FIG. 14D) NVP-BEZ235 (25 nM) treatment suppresses toxicity in primary rat cortical neurons overexpressing WT-TDP43-GFP. $p<0.05$, Hazard ratio=0.89, Cox proportional hazards analysis. N for each group represents total neurons pooled from three replicate experiments.

DEFINITIONS

Figure 1A:
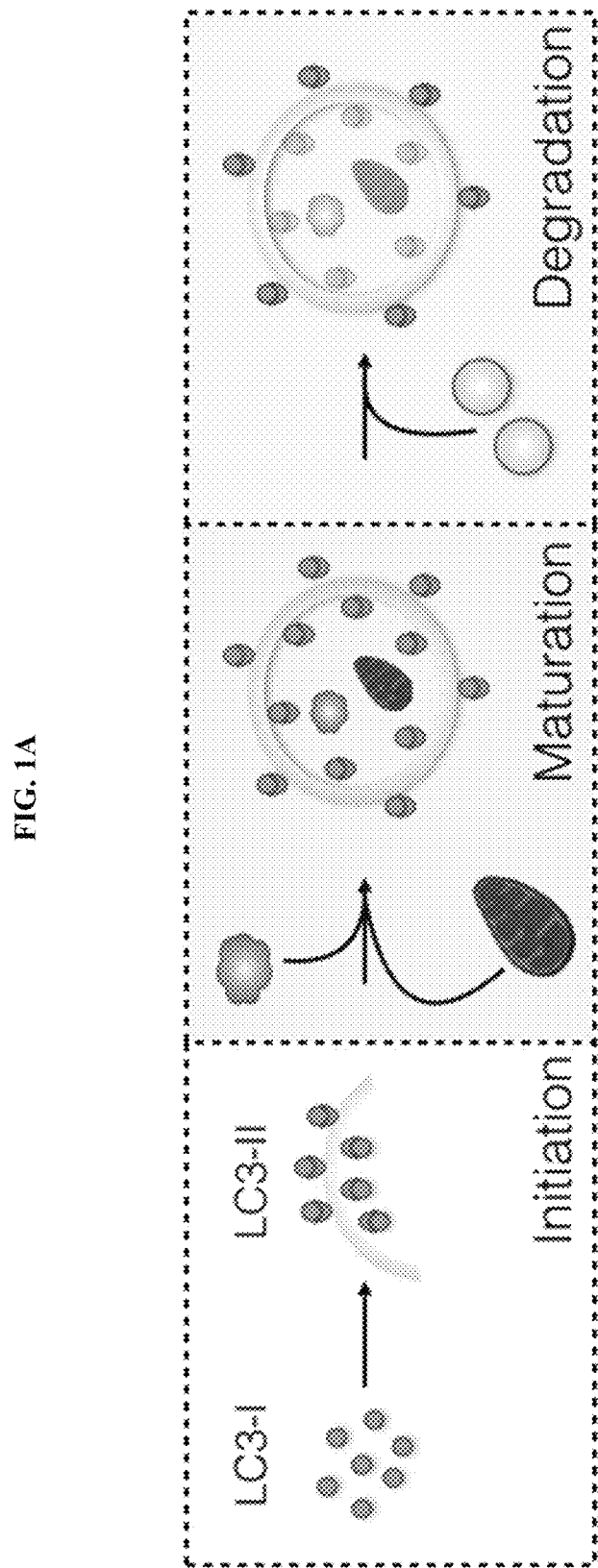

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a cell" is a reference to one or more cells and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the terms "engineered cell" or "engineered cell line" refer to a cell (or cell line) that had been genetically modified (e.g., via CRISPR/Cas9, via transfection, via recombinant DNA technology, etc.). An engineered cell expresses, produces, displays, etc. one or more small molecules, nucleic acids, peptides, proteins, carbohydrates, etc. that are not native to the parent cell, and/or expresses, produces, displays, etc. one or more small molecules, nucleic acids, peptides, proteins, carbohydrates, etc. at a level that is not native to the parent cell.

As used herein, the terms "parent cell" or parent cell line" refer to a cell (or cell line) that is identical to a particular engineered cell, but lacking the particular genetic modification of the engineered cell. The parent cell may be a cell that is used as a starting material for the production of an engineered cell, or may be a descendant of the cell used as the starting material.

As used herein, the term "photoconvertible fluorescent protein (pcFP)" refers to a fluorescent protein that, when exposed to a specific wavelength of light (e.g., specific range of wavelengths), undergoes an irreversible alteration in emission wavelength (e.g., from green to red).

DETAILED DESCRIPTION

Provided herein are compositions and systems comprising engineered cells useful for the measurement of autophagy induction, maturation and flux in a high-throughput manner.

Experiments were conducted during development of embodiments herein to establish a screening platform and develop/discover therapies and/or therapeutics capable of reversing neurodegeneration in ALS and FTD.

Autophagy has three major steps (Refs. 26-28; herein incorporated by reference in their entireties): (1) induction, (2) fusion of lysosomes with autophagosomes (maturation), and (3) cargo degradation (FIG. 1a). Available assays for autophagy are limited in their capacity to distinguish between these steps (Ref. 27; herein incorporated by reference in its entirety). Most rely upon the detection of pathway intermediates, precluding accurate estimates of autophagic activity or flux. Others perturb lysosomal function and therefore disrupt the very process they are intended to measure. Experiments conducted during development of embodiments herein utilized CRISPR/Cas9 genome editing (Refs. 29-30; herein incorporated by reference in their entireties) to create unique human cell lines that provide for simultaneous measurement of autophagy induction, maturation and flux in a high-throughput manner. In modified human embryonic kidney (HEK) cells, the native autophagy substrate and marker protein LC3 (Ref. 27; herein incorporated by reference in its entirety) is fused to Dendra2, a photoconvertible fluorescent protein (Refs. 32-33), providing a system to assess the separate stages of autophagy noninvasively in living cells, without the need for protein overexpression that may interfere with pathway activity. In experiments conducted during development of embodiments herein, Dendra2-LC3 HEK cells were used in a robust high-throughput screen (HTS) to identify potent autophagy modulators.

Figure 1B:
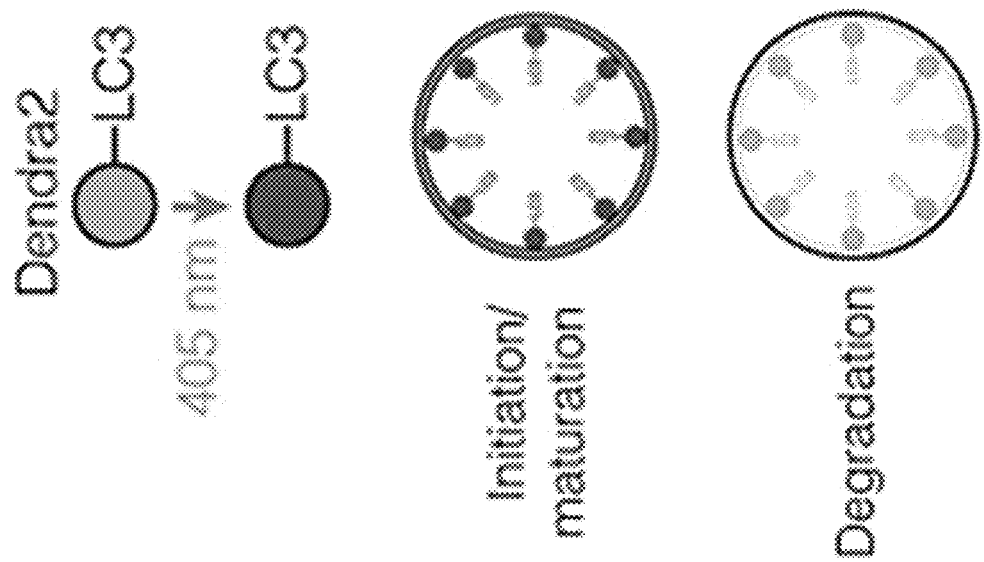

Experiments were conducted during development of embodiments herein to develop a sensitive method—optical pulse labeling (OPL)—that takes advantage of the photoconvertible fluorescent protein Dendra2 for estimations of autophagic flux in cellulo (Refs 14, 34; herein incorporated by reference in their entireties) (FIG. 1b). At baseline, Dendra2 exhibits spectral properties similar to green fluorescent protein (GFP), but following exposure to 405 nm light, it is irreversibly converted to a red fluorescent protein (Refs. 32-33; herein incorporated by reference in their entireties). Dendra2 was fused to LC3, a specific marker of autophagosomes and itself an autophagy substrate (Refs. 27, 31; herein incorporated by reference in their entireties). Following photoconversion, the time-dependent reduction in red LC3-Dendra2 (FIG. 1c) is used to calculate protein half-life, representing an estimate of autophagy flux for individual cells (Refs. 14, 34; herein incorporated by reference in their entireties) Furthermore, because LC3 is degraded as autophagosomes mature, the return to steady-state levels of green Dendra2-LC3 after photoconversion (FIG. 1d) reflects activity within the pathway as a whole. The assay is noninvasive, permitting longitudinal analyses of autophagy kinetics in living cells, and amenable to HTS. This method has proved to be sensitive and specific, demonstrating autophagic induction at 10-fold lower levels compared to conventional approaches (Ref. 14; herein incorporated by reference in its entirety). It has also been successfully employed to identify a series of small molecule autophagy inducers in primary rodent neurons (Ref. 14; herein incorporated by reference in its entirety), demonstrating the utility of OPL for measuring changes in autophagic flux.

Figure 2A:
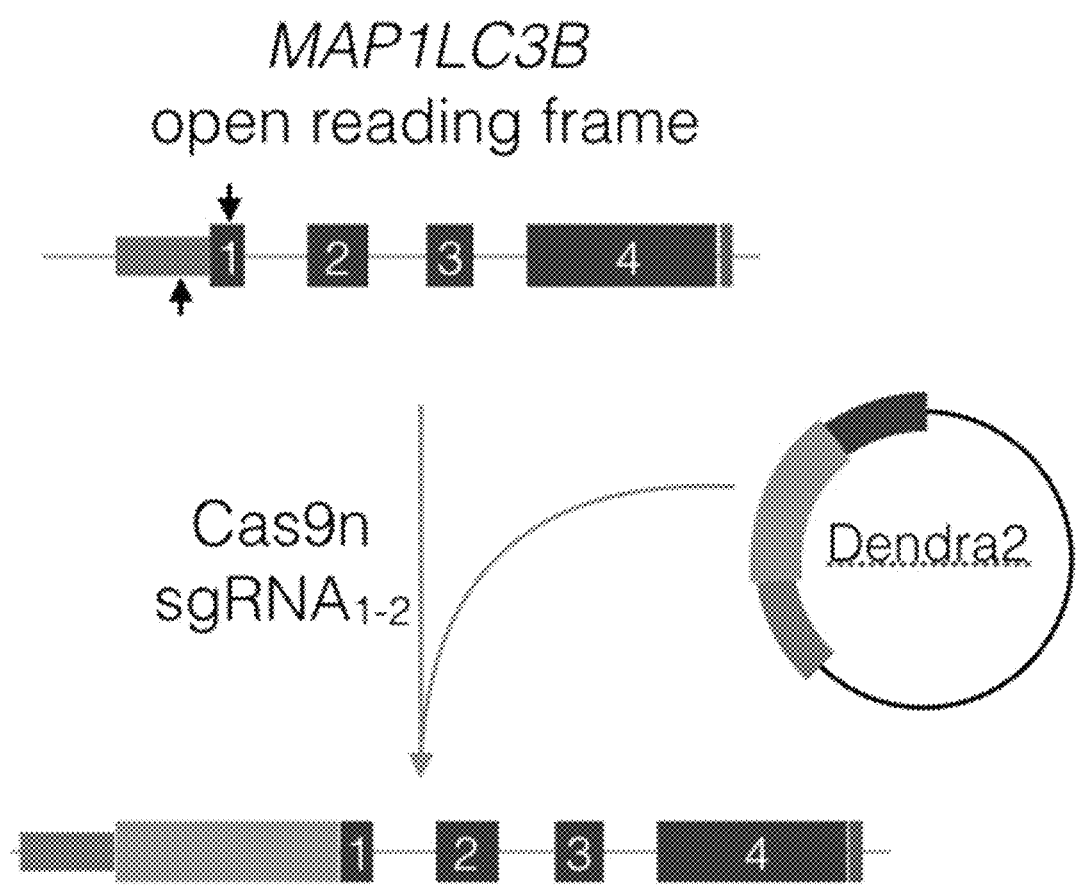
FIGS. 2A-D. Creation of an exemplary Dendra2-LC3 reporter cell line.
Figure 2B:
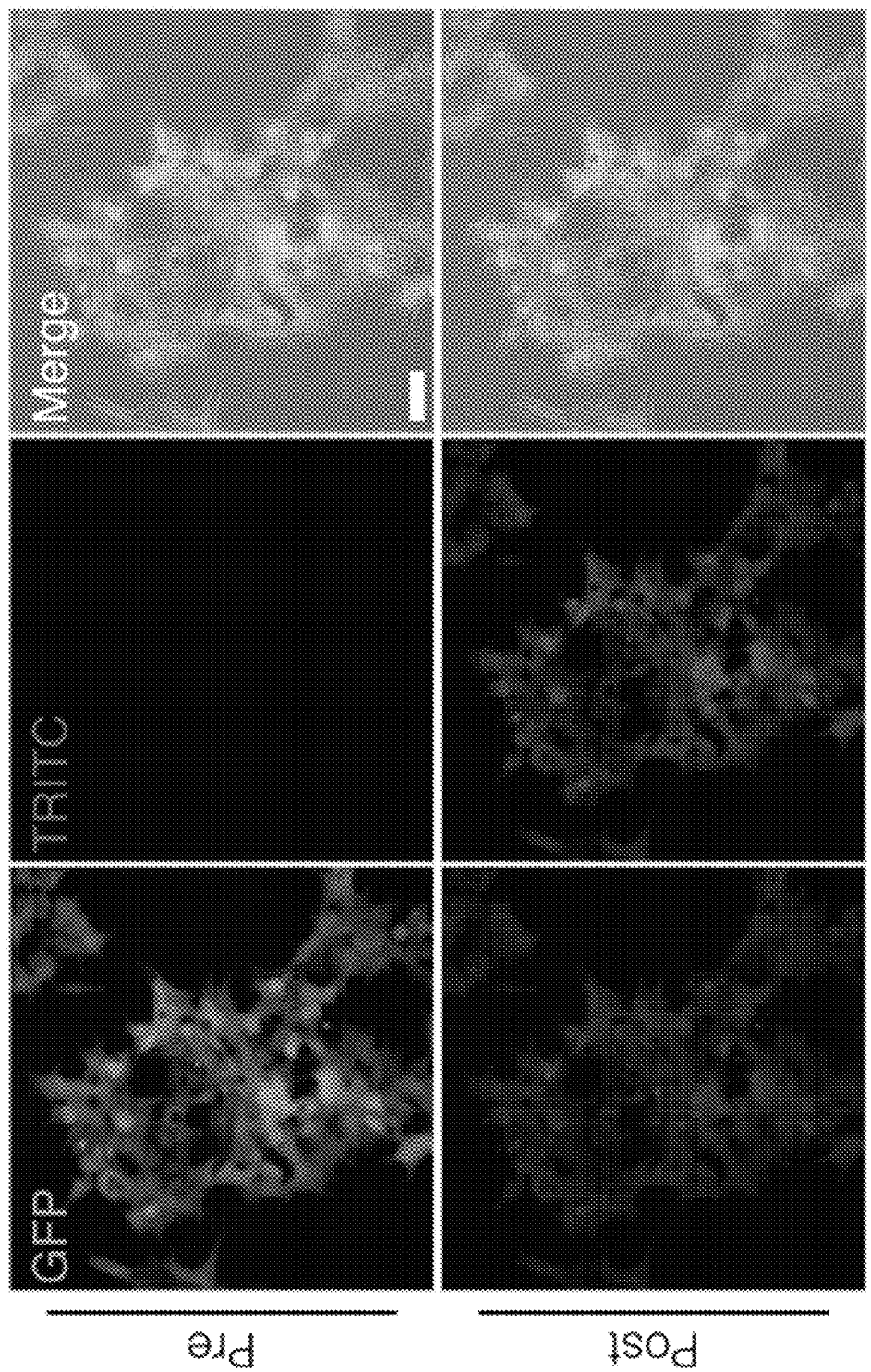
Figure 2D:
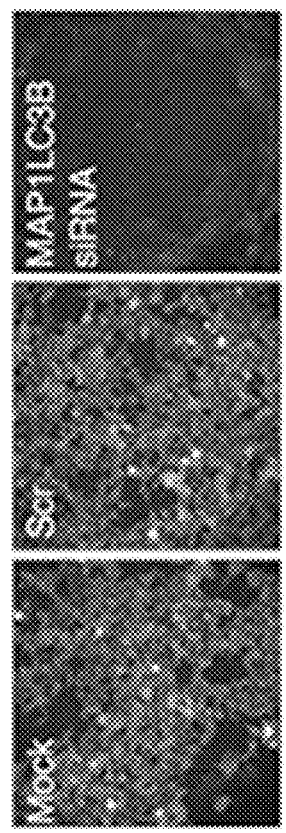
Figure 2C:
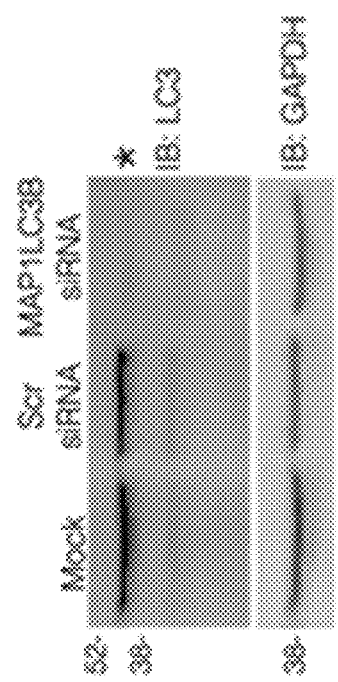
Figure 3B:
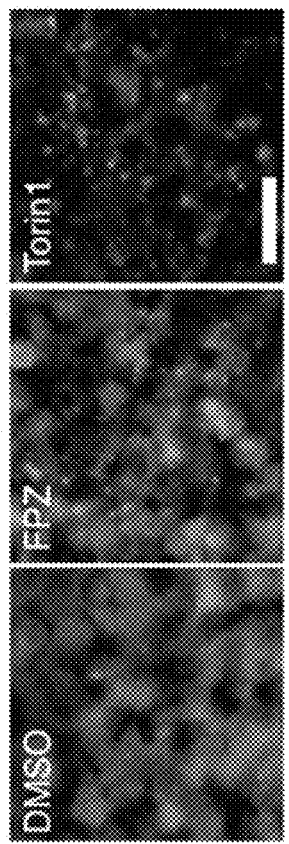
Figure 3A:

Conventional methods for estimating autophagy flux rely upon the assessment of LC3 or other autophagy substrates by Western blotting or immunocytochemistry (Ref. 27; herein incorporated by reference in its entirety); by their very nature, these techniques are static and limited to dead cells. Fluorescence-based methods that use tagged substrates allow visualization of autophagy within living cells, but typically require the overexpression of autophagy target proteins that may disrupt the very process they are intended to measure. To assess autophagy in human cells without compromising or interfering with the pathway, experiments were conducted during development of embodiments herein utilizing CRISPR/Cas9 genome editing (Refs. 29-30; herein incorporated by reference in their entireties) to insert the Dendra2 open reading frame into the MAP1LC3B locus (encoding LC3) of HEK cells (FIG. 2a). A mutated, nickase version of Cas9 (Cas9n) was used that is incapable of making double-stranded DNA breaks, thereby minimizing the risk of non-homologous end joining and unwanted insertions or deletions (Refs. 29, 35; herein incorporated by reference in their entireties). Two separate single guide RNAs (sgRNAs) were designed that recognize sequences just upstream and downstream of the MAP1LC3B start codon, and a homology directed repair (HDR) vector encoding the Dendra2 open reading frame flanked by 400 bp of homologous sequence surrounding the MAP1LC3B start codon (FIG. 2a). Following expression of the sgRNAs, Cas9n and the HDR in HEK cells, colonies were selected based upon green fluorescence and passaged to homogeneity (FIG. 2b). The insertion site was confirmed by DNA sequencing, PCR, and immunocytochemistry using antibodies that recognize LC3. Providing further validation of the insertion, transfection with siRNA directed against the MAP1LC3B locus elicited a significant reduction in Dendra2-LC3 protein levels as measured by western blotting and native GFP fluorescence (FIG. 2c, d). In untreated cells, Dendra2-LC3 fluorescence appears diffuse, as expected (FIG. 3a). Live-cell, time-lapse microscopy demonstrated the rapid formation of small fluorescent puncta upon nutrient deprivation (a common method for stimulating autophagy (Ref. 27; herein incorporated by reference in its entirety), concomitant with a reduction in the diffuse GFP signal. Furthermore, application of torin-1 and fluphenazine (FPZ), mTOR-dependent and -independent autophagy inducers identified in previous work (Refs. 14, 36; herein incorporated by reference in their entireties), effectively elicits the formation of LC3-positive puncta and reduces the steady-state GFP intensity (FIG. 3b). These observations demonstrate that genetically-modified Dendra2-LC3 HEK cells are useful in assessing autophagy induction by a variety of stimuli. Second, autophagy induction in these cells is accompanied not only by the formation of puncta, but also by relative decreases in diffuse Dendra2-LC3 fluorescence, as indicated by the model in FIG. 1.

Based on these results, a screening platform was developed based on Dendra2-LC3 HEK cells for the detection of small molecule and genetic modifiers of autophagy flux. For these studies the potent mTOR inhibitor torin1 (Ref. 36; herein incorporated by reference in its entirety) was selected as a positive control for autophagy induction, and the vacuolar ATPase inhibitor bafilomycin-A1 (Ref. 37; herein incorporated by reference in its entirety) as a positive control for autophagy inhibition. In each case, DMSO served as a vehicle (negative) control. Dendra2-LC3 was photoconverted immediately prior to drug application, and the fluorescence intensity in the green (GFP) and red (RFP) channels was measured at regular intervals for 15 h. Torin1 significantly enhanced Dendra2-LC3 degradation, while bafilomycin-A1 slowed its clearance (FIG. 3c). In concordance with its ability to prevent lysosomal and autophagosomal acidification, bafilomycin-A1 completely blocked the effects of torin1 on Dendra2-LC3 degradation.

Figure 3E:
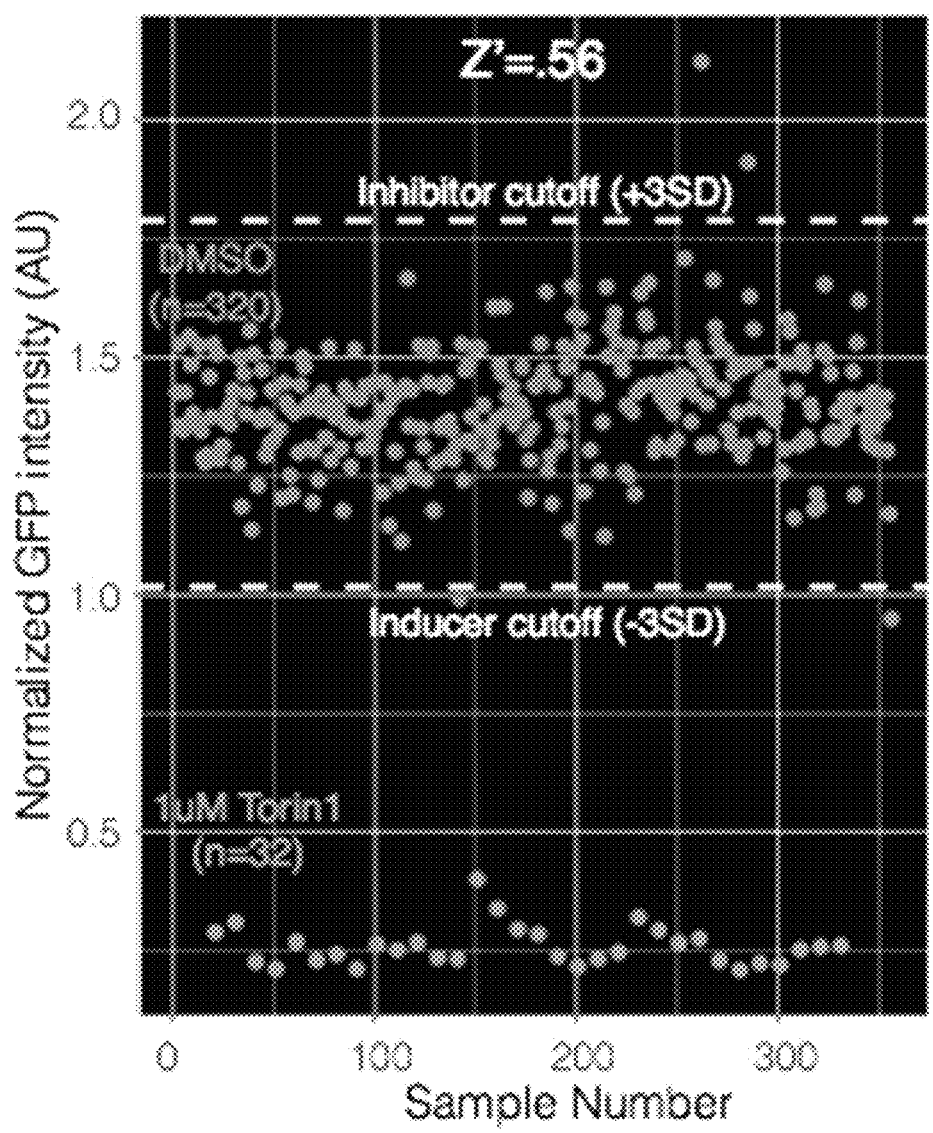

Despite these promising results, the absolute difference in Dendra2-LC3 half-life between DMSO- and torin1-treated cells was only 2.5 h, limiting the usefulness of this readout in a primary screening assay. In contrast, following photoconversion a dramatic difference between DMSO and torin1 was observed in the GFP channel (FIG. 3d). Treatment with torin1 elicited a highly significant and durable reduction in GFP intensity in Dendra2-LC3 HEK cells that was fully blocked by bafilomycin-A1. The relative change in GFP signal measured 15 hours after application of torin1 proved to be a rigorous and consistent measure of autophagy flux over repeated experiments. The Z' value for the effect of torin1 on the normalized GFP intensity, calculated as a ratio of GFP intensity at 15 h to that at 0 h (T15/T0), was 0.63 when the assay was conducted in a 96-well format in our laboratory, and 0.56 when conducted in a 384-well format at the Center for Chemical Genomics (CCG, FIG. 3e), indicative of a robust screening platform (Ref. 38; herein incorporated by reference in its entirety). Using a cutoff of 3 standard deviations (SD) above and below the mean normalized GFP intensity (T15/T0) for DMSO-treated cells, a 1% false positive rate was estimated for the identification of both autophagy inducers and inhibitors. The false negative rate was near zero, ensuring a highly sensitive assay.

Figure 4:
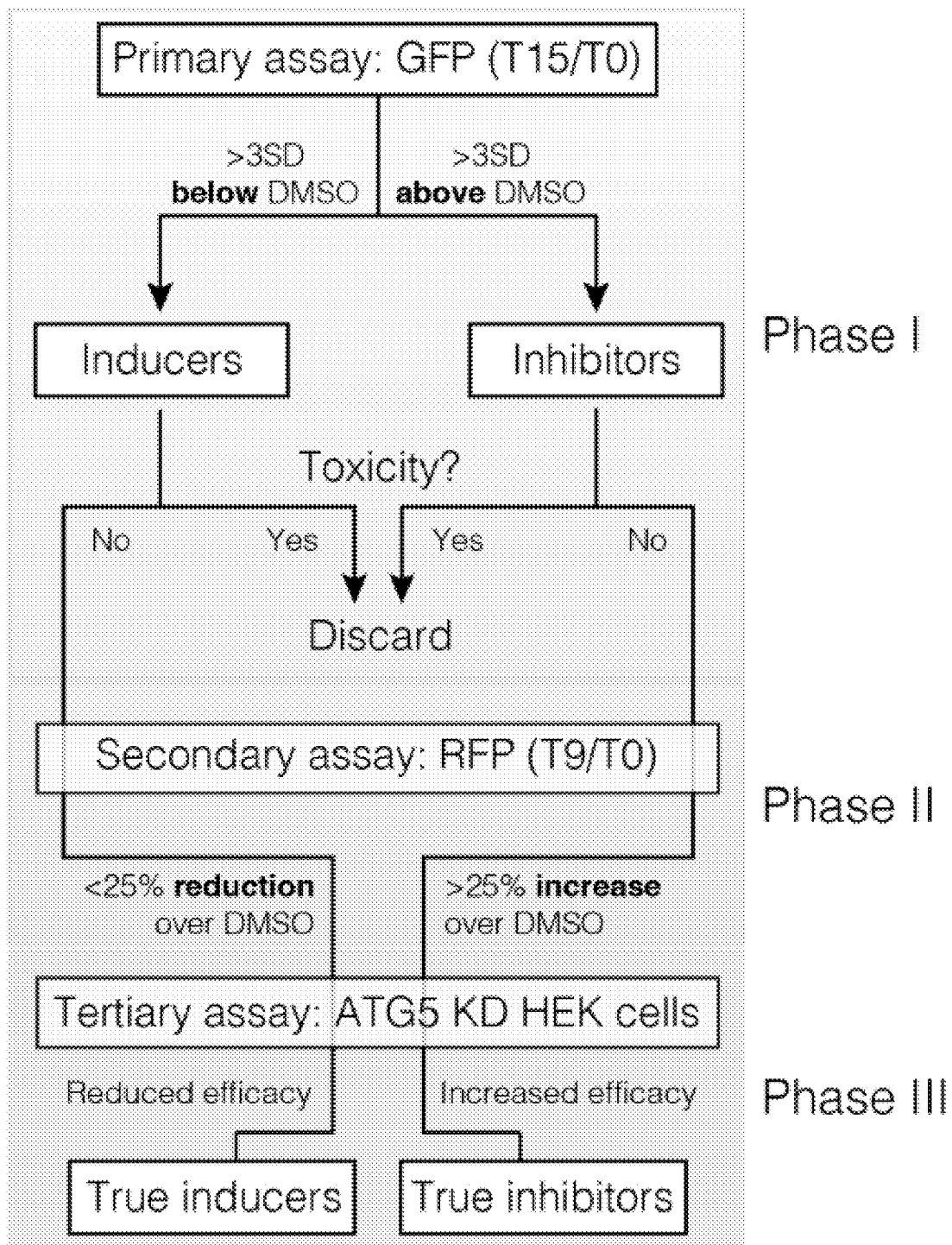
FIG. 4. Exemplary screening pipeline for the identification of true autophagy inducers and inhibitors.

Based on these data, a 3-phase screening pipeline was established for the identification of autophagy-modulating compounds (FIG. 4). The bidirectional aspect of the phase I readout permits classification of autophagy inducers as well as inhibitors; both may be valuable for future investigations of regulatory pathways governing autophagy activity in HEK and other cell types. The possibility that cell death and toxicity mimics the reduction in GFP intensity that would otherwise denote autophagy induction was also addressed. To avoid confounding from toxicity, the area occupied by cells in each image is calculated using ImageJ software and used as a proxy for cell number; since all wells received the same number of cells, >25% reductions in the area occupied by cells at the end of the experiment indicates toxicity. The formation of Dendra2-LC3 puncta in each condition is scored simultaneously using the 'analyze particles' function in ImageJ. Phase II of the screening pipeline involves the measurement of Dendra2-LC3 degradation kinetics by OPL (FIG. 3c), providing additional verification of the effects of each compound on autophagy flux. This step is also necessary for eliminating compounds that reduce steady-state Dendra2-LC3 GFP fluorescence via global impairments in protein synthesis. In phase III, lead compounds are screened in Dendra2-LC3 HEK cells deficient in the essential autophagy gene ATG5 (Ref. 11; herein incorporated by reference in its entirety). True autophagy inducers will be ineffective in these cells, while true autophagy inhibitors will compound ATG5-related impairments in autophagy flux.

Figure 5:
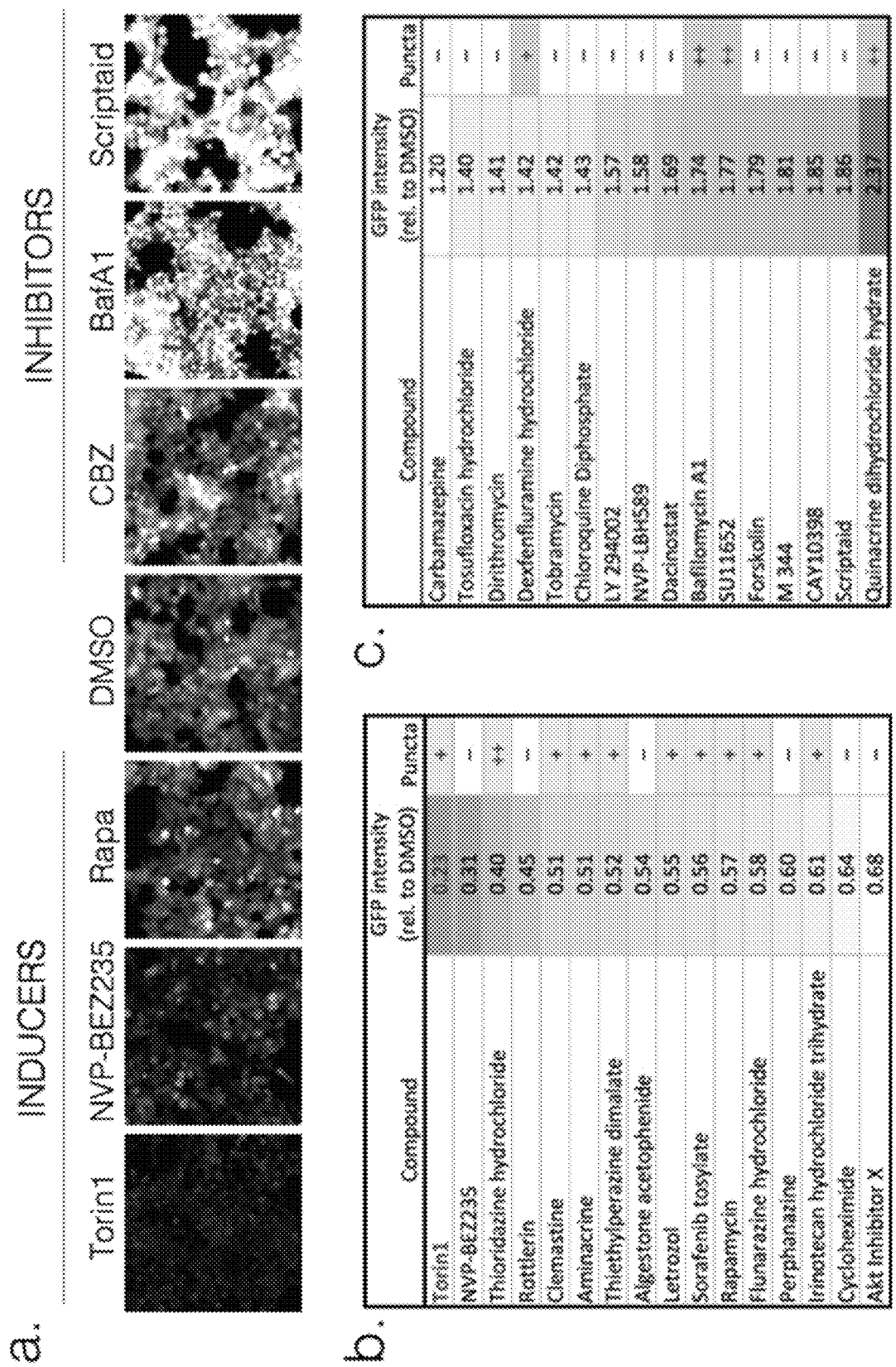
FIG. 5, panels a-c. Autophagy inducers and inhibitors revealed by Phase I screening in Dendra2-LC3 HEK cells. (Panel a) Representative images of Dendra2-LC3 HEK cells 15 h after treatment with the indicated compounds, showing a reduction in GFP fluorescence for inducers (left) and an increase for inhibitors (right). Select inducers and inhibitors are listed in (Panel b) and (Panel c), respectively, alongside the change in GFP intensity relative to vehicle (DMSO) control, and presence (+) or absence (−) of Dendra2-LC3 puncta.

Experiments conducted during development of embodiments herein involving phase I and phase II screening indicate that the approach outlined in FIG. 4 is both valid and effective for identifying autophagy-modulating molecules. The Prestwick library of 1,280 compounds, consisting of drugs approved by the FDA, EMA and related agencies for the treatment of a wide variety of human disorders, was screened. The Enzo autophagy collection, made up of 248 molecules with previously demonstrated effects (both positive and negative) on autophagy, was also screened. In phase I, the normalized GFP intensity (T15/T0) cleanly distinguished potential autophagy inducers from inhibitors and compounds without significant effects on autophagy (FIG. 5a-c). The data highlighted several examples of autophagy inducers noted in prior studies, including rapamycin and Akt inhibitor X (Refs. 15, 39; herein incorporated by reference in their entireties), confirming construct validity for the assay. An enrichment for first-generation antipsychotics has previously been observed among autophagy inducers (Refs. 14-15; herein incorporated by reference in their entireties), an effect replicated in the current experiments four of the 16 compounds listed in FIG. 5b are first generation antipsychotics. As expected from their mode of action, mTOR inhibitors (torin1, rapamycin, and NVP-BEZ235) also rank among the most potent inducers. Additionally, however, several novel autophagy-inducing compounds were identified that promise to reveal new and important pathways responsible for the regulation of autophagy. Of the potential autophagy inducers, some had recognized effects on protein synthesis, such as cycloheximide. In phase II experiments, these compounds failed to affect Dendra2-LC3 degradation kinetics, demonstrating the ability of the screening platform to eliminate false positives while highlighting compounds with veritable effects on autophagy flux.

The Prestwick and Enzo collections contained a number of compounds with purported autophagy-inducing activity, yet in the phase I assay many of these drugs were instead identified as autophagy inhibitors (FIG. 5b). For example, carbamazepine (CBZ) and Scriptaid were previously described as autophagy inducers based on the accumulation of LC3-II in cells treated with either compound. However, significant increases in Dendra2-LC3 GFP fluorescence were observed upon application of either compound, indicating autophagy inhibition. This interpretation was confirmed by limited phase II experiments, in which Dendra2-LC3 degradation kinetics was measured in HEK cells treated with CBZ and Scriptaid. Both significantly slowed Dendra2-LC3 degradation in comparison to DMSO, indicating inhibition rather than induction of autophagy. These results provide additional evidence that the screening pipeline described herein is particularly useful in discriminating true autophagy inducers from inhibitors and other compounds with indeterminate effects on autophagy.

In some embodiments, provided herein are polypeptides comprising an autophagy biomarker fused to a photoconvertable fluorescent protein (fcFP). In some embodiments, the fusion of the autophagy biomarker and the fcFP is expressed within a cell. In some embodiments, provided herein are engineered cells and cell lines that express the fusions herein. In some embodiments, the fusions are produced, displayed, degraded, etc. under the same conditions (e.g., autophagy) as the autophagy biomarker alone. Therefore, detection, quantification, and/or monitoring of the fusions herein provides systems and methods for monitoring/measuring/detecting autophagy with a cell.

In some embodiments, any autophagy biomarker that correlates with level of autophagy, autophagy flux, or one or more of the steps of autophagy finds use as an autophagy biomarker in the fusions, cells, systems, and methods herein. For example, in some embodiments, an autophagy biomarker is selected from the group consisting of microtubule-associated proteins 1A/1B light chain 3B (LC3), p62/sequestosome 1, and Beclin 1. In some embodiments, the autophagy biomarker is LC3.

In some embodiments, the fcFP fused to the autophagy biomarker provides a reporter for the level of autophagy. In some embodiments, because the reporter is photoconvertable, it is possible to identify whether the fusion was generated before or after photoconversion, and it is possible to separate the degradation of post-converted fcFP from the generation of new fcFP.

In some embodiments, the fcFP is an irreversible fcFP. In some embodiments, an irreversible fcFP is selected from the group consisting of PAGFP, PS-CFP, PS-CFP2, PAmRFP1-1, PAmRFP1-2, PAmRFP1-3, PAmCherry1, PAmCherry2, PAmCherry3, KFP, Kaede, mEosFP, mEos2, KikGR, mKikGR, and IrisFP. In some embodiments, the fcFP is a reversible fcFP. In some embodiments, the reversible fcFP is selected from the group consisting of Dronpa, Dendra, Dendra2, and IrisFP. In some embodiments, the fcFP is Dendra2.

In some embodiments, the autophagy biomarker is microtubule-associated proteins 1A/1B light chain 3B (LC3) and the fcFP is Dendra2.

In some embodiments, the fcFP and the autophagy biomarker are directly fused. In some embodiments, the fcFP and the autophagy biomarker are fused via a linker segment. In some embodiments, a linker segment is between 1 and 200 amino acids in length (e.g., 1, 2, 3, 4, 5, 6, 7, 8, 9, 10, 20, 30, 40, 50, 75, 100, 125, 150, 175, 200, or ranges of amino acids therebetween). In some embodiments, a linker facilitates the two portions of the fusion performing their separate functions with minimal interference.

In some embodiments, the cell lines, systems and methods herein find use in screening of agents or methods for altering autophagy. In some embodiments, such screens are performed in a high-throughput manner to analyze a large library of compounds, peptides, or other agents. In some embodiments, screens are conducted in microtiter assay plates. Exemplary assay plates include 96-well, 384-well, 1,536-well, or 3,456-well microtiter plates. In some embodiments, the total assay volume is less than 5 µl, 10 µl, 15 µl, 20 µl, 25 µl, 30 µl, 40 µl, 50 µl, 75 µl, or 100 µl (or ranges therebetween). In some embodiments, candidate modulators of autophagy may be screened at single concentrations or in dose-responses. In some embodiments, candidate modulators of autophagy are screened at single concentrations (e.g., 100 nM, 1 µM, 2 µM, 5 µM, 10 µM, 20 µM, 50 µM, 75 µM, 100 µM, or ranges therebetween). In some embodiments, candidate modulators of autophagy are screened in dose-responses, with a highest final concentration of 100 nM, 1 µM, 2 µM, 5 µM, 10 µM, 20 µM, 50 µM, 75 µM 100 µM, or ranges therebetween. In some embodiments, a cell or a group of cells is contacted with the candidate modulators of autophagy individually, e.g., in separate microtiter plate wells, or in pools of up to 2, 3, 4, 5, 7, 8, 9, or 10, 20, 50, 100, or ranges therebetween. In some embodiments, the screen is completed within a 24 hour time period. In some embodiments, the screen is conducted using automated screening equipment, such as plate handling robotics and automated liquid handling.

In some embodiments, provided herein are nucleic acids and nucleic acid sequences encoding polypeptides and fusions described above and vectors and cells harboring such nucleic acids. In some embodiments, nucleic acid molecules are recombinant nucleic acid molecules. In some embodiments, nucleic acid molecules are synthetic. Nucleic acids encoding polypeptides and fusions described herein comprise DNA, RNA, PNA (peptide nucleic acid), and hybrids thereof.

In some embodiments, a nucleic acid encoding polypeptide and/or fusion described herein comprises one or more regulatory sequences. For example, promoters, transcriptional enhancers and/or sequences that allow for induced expression of the polynucleotide of the disclosure may be employed. In some embodiments, nucleic acid molecules are transcribed by an appropriate vector comprising a chimeric gene that allows for the transcription of the nucleic acid molecule in the cell.

In some embodiments, a nucleic acid molecule is a recombinantly-produced chimeric nucleic acid molecule comprising any of the aforementioned nucleic acid molecules either alone or in combination. In some embodiments, the nucleic acid molecule is part of a vector.

In some embodiments, provided herein are vectors comprising the nucleic acid molecule described herein. Many suitable vectors are known to those skilled in molecular biology, the choice of which would depend on the function desired and include plasmids, cosmids, viruses, bacteriophages and other vectors used conventionally in genetic engineering. Methods that are well known to those skilled in the art can be used to construct various plasmids and vectors; see, for example, the techniques described in Sambrook et al. (1989) and Ausubel, Current Protocols in Molecular Biology, Green Publishing Associates and Wiley Interscience, N.Y. (1989), (1994); incorporated by reference in its entirety. Alternatively, the polynucleotides and vectors of the disclosure are reconstituted into liposomes for delivery to target cells. A cloning vector may be used to isolate individual sequences of DNA. Relevant sequences can be transferred into expression vectors where expression of a particular polypeptide is required. Typical cloning vectors include pBluescript SK, pGEM, pUC9, pBR322 and pGBT9. Typical expression vectors include pTRE, pCAL-n-EK, pESP-1, pOP13CAT.

In some embodiments, a vector comprises a nucleic acid sequence that is a regulatory sequence operably linked to the nucleic acid sequence encoding a polypeptide and/or fusion described herein. Such regulatory sequences (control elements) are known to the artisan and may include a promoter, a splice cassette, translation initiation codon, and insertion site for introducing an insert into the vector. In specific embodiments, the nucleic acid molecule is operatively linked to said expression control sequences allowing expression in eukaryotic or prokaryotic cells.

In some embodiments, the vector is a viral vector, such as a lentiviral vector or adenovirus associate vector.

In some embodiments, nucleic acids and/or vectors are used in a cell to express encoded polypeptides and/or fusions in the cells. The nucleic acid molecules or vectors containing the DNA sequence(s) encoding any of polypeptides and fusions described herein are introduced into the cells that in turn produce the polypeptide(s) and/or fusion(s). The recited nucleic acid molecules and vectors may be designed for direct introduction or for introduction via liposomes, or viral vectors (e.g., adenoviral, retroviral) into a cell.

In some embodiments, provided herein are methods comprising culturing a host cell defined herein above under conditions allowing the introduction of the nucleic acid and/or vector. In some embodiments, provided herein are methods comprising culturing a host cell defined herein above under conditions allowing expression of a construct (e.g., comprising a polypeptide and/or fusion described herein). Conditions for the culturing of cells harboring an expression construct are known in the art.

In some embodiments, nucleic acids encoding the polypeptides and/or fusions are inserted into the genetic material of a host cell (parent cell) using a CRISPR/Cas9 system. CRISPRs are DNA loci comprising short repetitions of base sequences. Each repetition is followed by short segments of "spacer DNA" from previous exposures to a virus. CRISPRs are often associated with Cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms. The CRISPR/Cas system may be used for gene editing. By delivering the Cas9 protein and appropriate guide RNAs into a cell, the organism's genome can be cut at any desired location. Methods for using CRISPR/Cas9 systems, and other systems, for insertion of a gene into a host cell to produce an engineered cell are described in, for example, U.S. Pub. No. 20180049412; herein incorporated by reference in its entirety.

In some embodiments, the cells, fusions, and nucleic acids described herein find use in a variety of applications. In some embodiments, systems and methods are provided herein for performing high-throughput screens to identify compounds, genetic strategies, and other agents that stimulate autophagy flux.

The cell lines, systems and methods herein exhibit numerous advantageous characteristics for measuring/monitoring autophagy. For example, the cell lines, systems and methods herein are not dependent on pathway intermediates, directly measures activity of the autophagy pathway itself, are highly amenable to high-throughput screening (Z'>0.5), and adaptable to pharmacologic and genetic screening strategies, do not require protein (e.g., fusion) overexpression that confounds the measurement of autophagy flux, and provide high-content as well as high-throughput analyses of the three separate stages of autophagy.

EXPERIMENTAL

Example 1

Screening a Library of 24,000 Diverse Compounds for Novel Autophagy Inducers and Inhibitors Experiments conducted during development of embodiments herein demonstrate Dendra2-LC3 HEK cells are a powerful means of identifying true autophagy inducers and inhibitors. HTS assay parameters were optimized and a 3-phase screening pipeline was validated (FIG. 4) for identifying autophagy-modulating compounds. The 24,000 compound Maybridge library is selected for additional testing of the system.

In phase I of the screening pipeline, Dendra2-LC3 HEK cells are plated in 384-well plates using the Biomek FX high-density replication pin tool (Beckman), photoconverted and imaged using the ImageXpress MicroCellular Imaging and Analysis System (MDS Analytical Technologies). Immediately before and after photoconversion with 405 nm light, 2 images per well in the GFP channel are acquired. Compounds are then applied at a standard dose (final concentration, 6.5 µM per well) using the Biomek FX liquid handler. After 15 h, images are acquired once more in the GFP channel, and a ratio of GFP (T15/T0h) calculated to determine relative autophagy flux in each condition (FIG. 3d). Using custom scripts in ImageJ, images are inspected for puncta formation and surface area occupied by the cells; conditions demonstrating >25% reduction in area are discarded due to toxicity.

Compounds demonstrating a >3 SD change in normalized GFP intensity (T15/T0) and minimal toxicity are selected for phase II of the pipeline (FIG. 4). Dendra2-LC3 cells are imaged in the red channel just before and after photoconversion using the ImageXpress, thereby detecting photoconverted Dendra2-LC3. Select compounds that passed the phase I criteria (estimated hit rate 1%, or 2400 compounds) are applied using the Mosquito X1 liquid handler (TTP Labtech), and the plates imaged in the red channel at hourly intervals for a 15 h period. For each condition, Dendra2-LC3 degradation kinetics (FIG. 3c) are calculated from the resulting images using custom scripts in ImageJ and R.

Drugs capable of accelerating or slowing Dendra2-LC3 degradation by at least 25% in comparison to vehicle (DMSO) control are selected for further analysis in phase III (FIG. 4).

Figure 6:
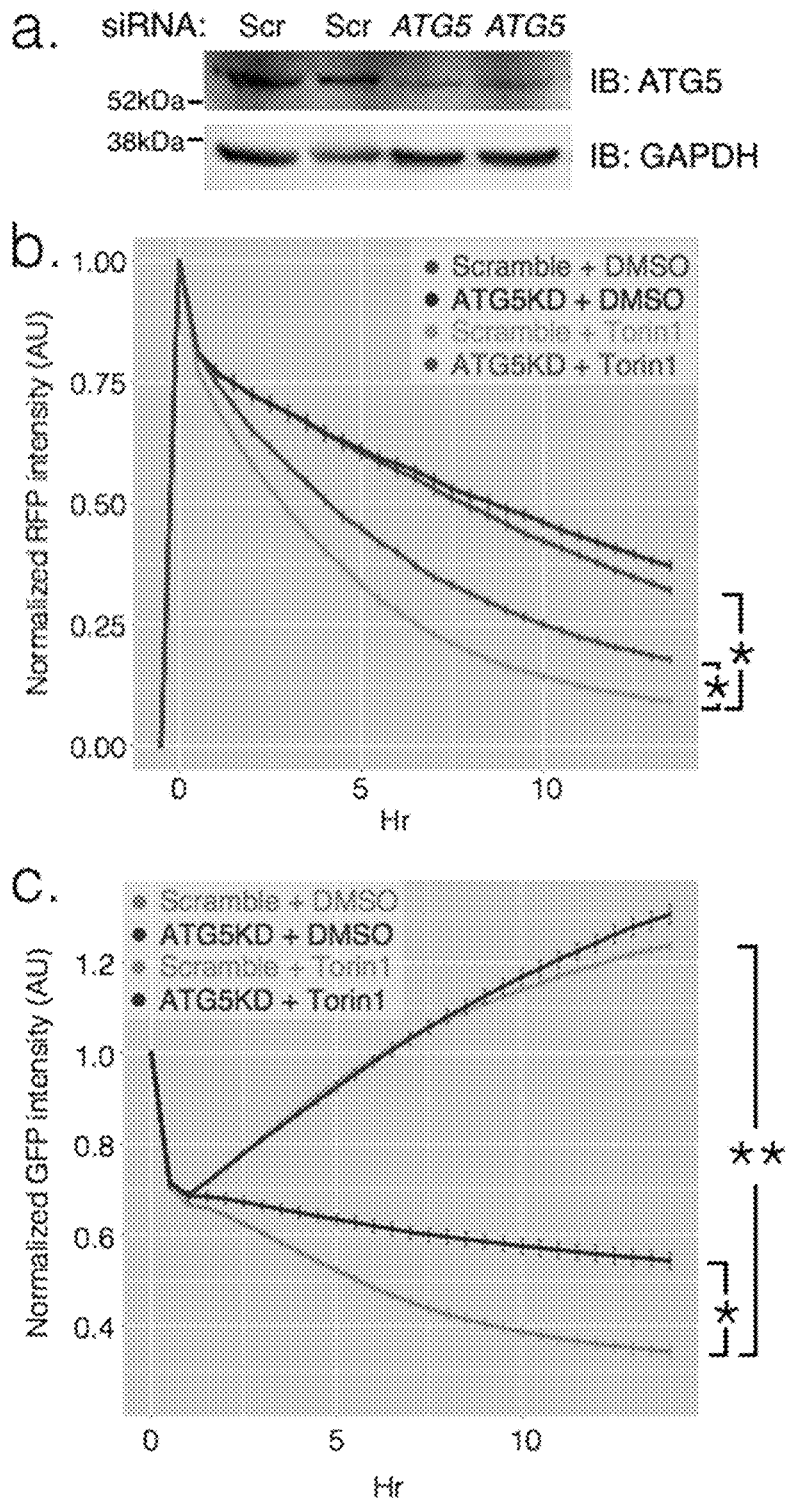
FIG. 6, panels a-c. Evaluation of autophagy-modifying compounds in ATG5-deficient cells. (Panel a) Western blot of Dendra2-LC3 HEK cells transfected with scrambled siRNA (Scr) or siRNA targeting the ATG5 locus (ATG5), demonstrating effective reduction of the ATG5 protein. IB, immunoblot. (Panels b, c) ATG5 knockdown attenuates the ability of torin1 to induce autophagic flux, as determined by the impaired degradation of photoconverted (Panel b) Dendra2-LC3, and the stalled return of native (Panel c) Dendra2-LC3 after photoconversion. * $p<0.05$; ** $p<0.0001$, one-way ANOVA with Dunnett's post-test.
Figure 7A:
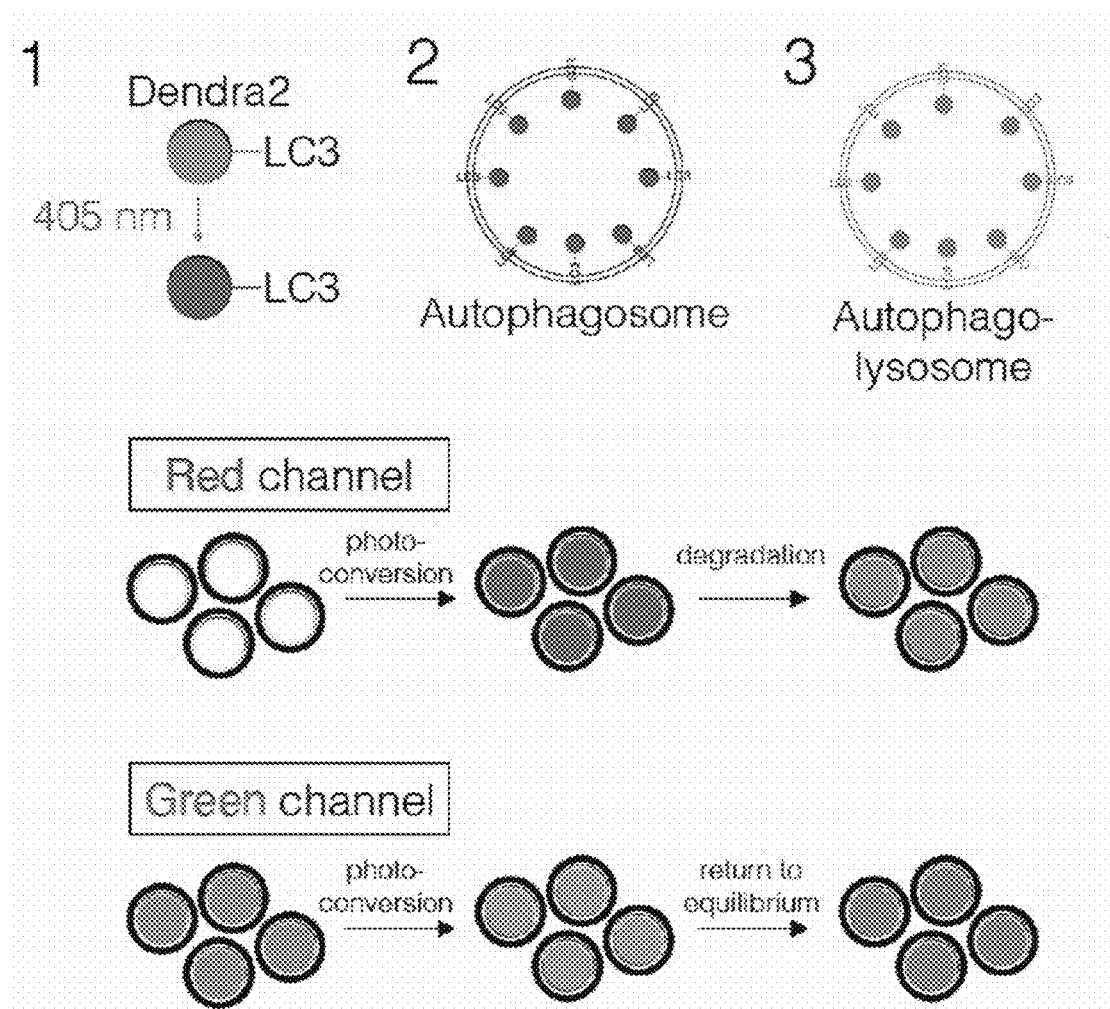
Figure 7D:
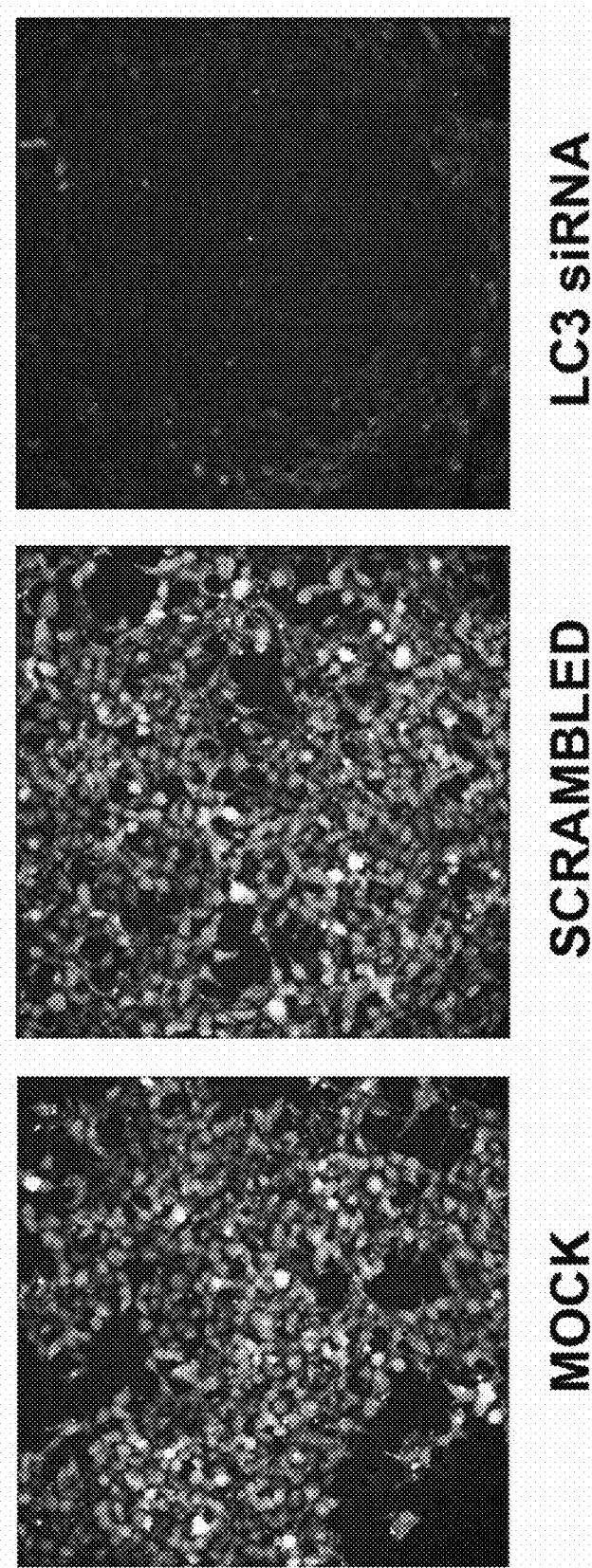
Figure 8A:
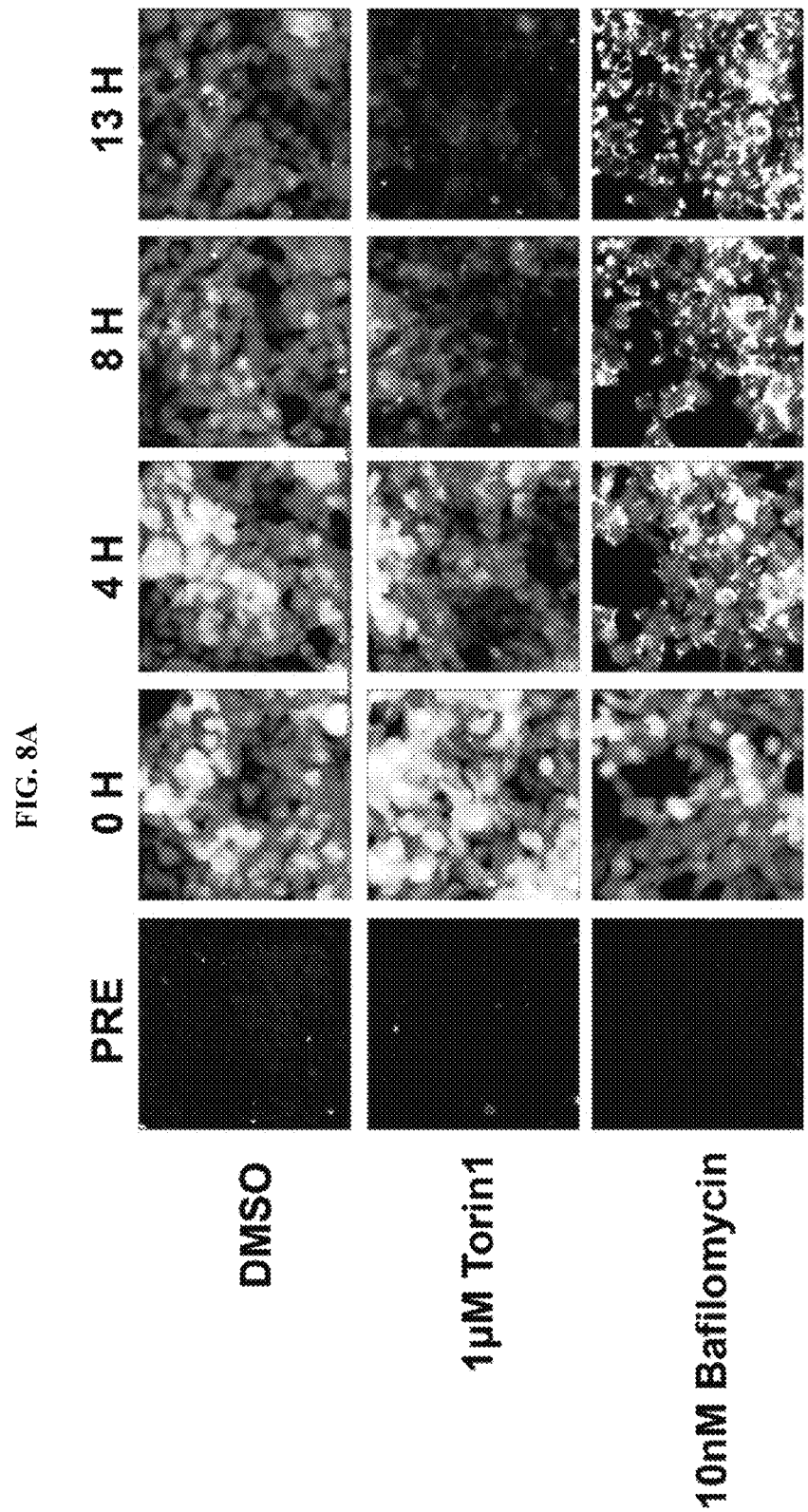
Figure 9A:
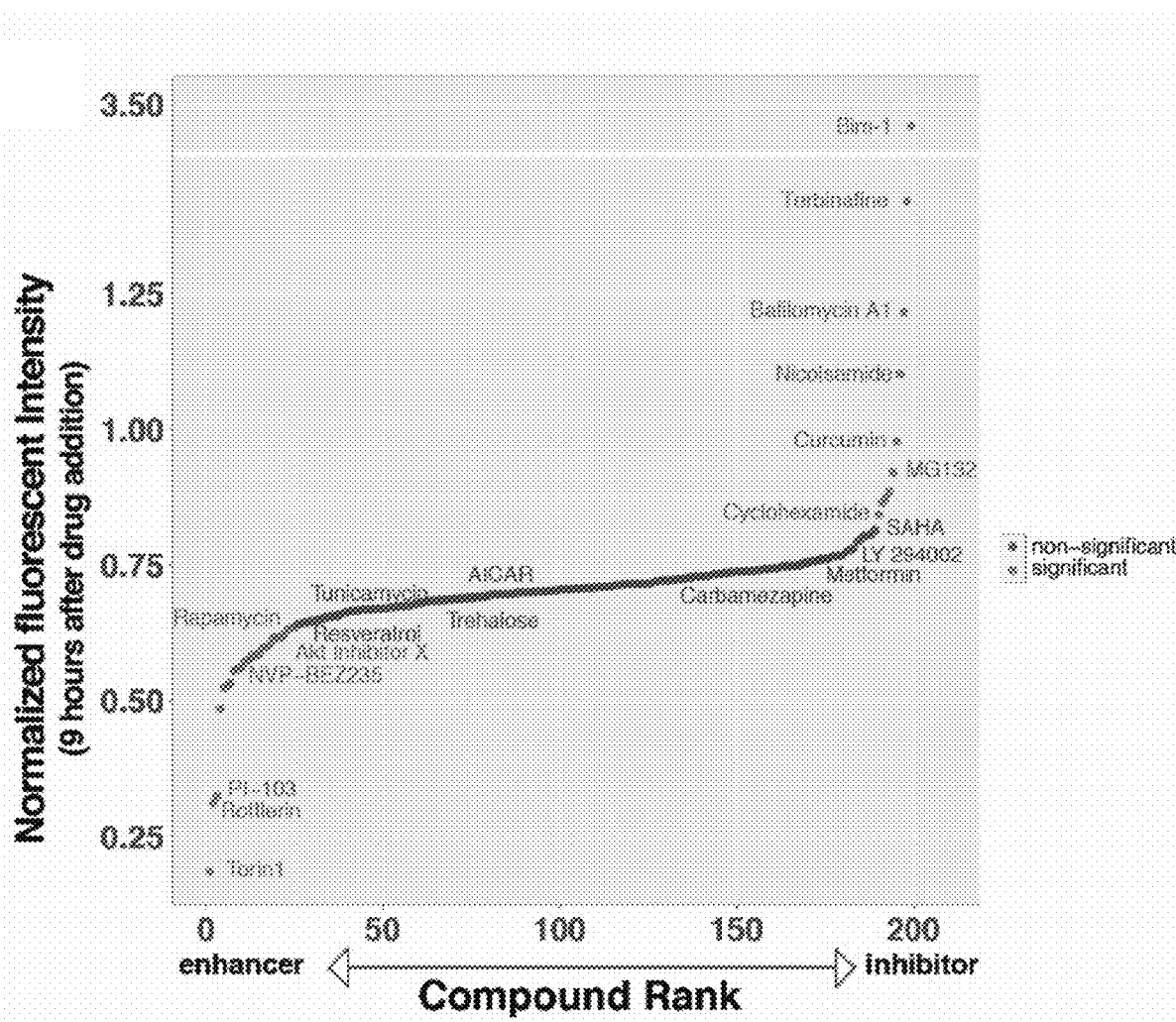
FIG. 9A-C. Evaluating the efficacy of known autophagy modulators.
Figure 9B:
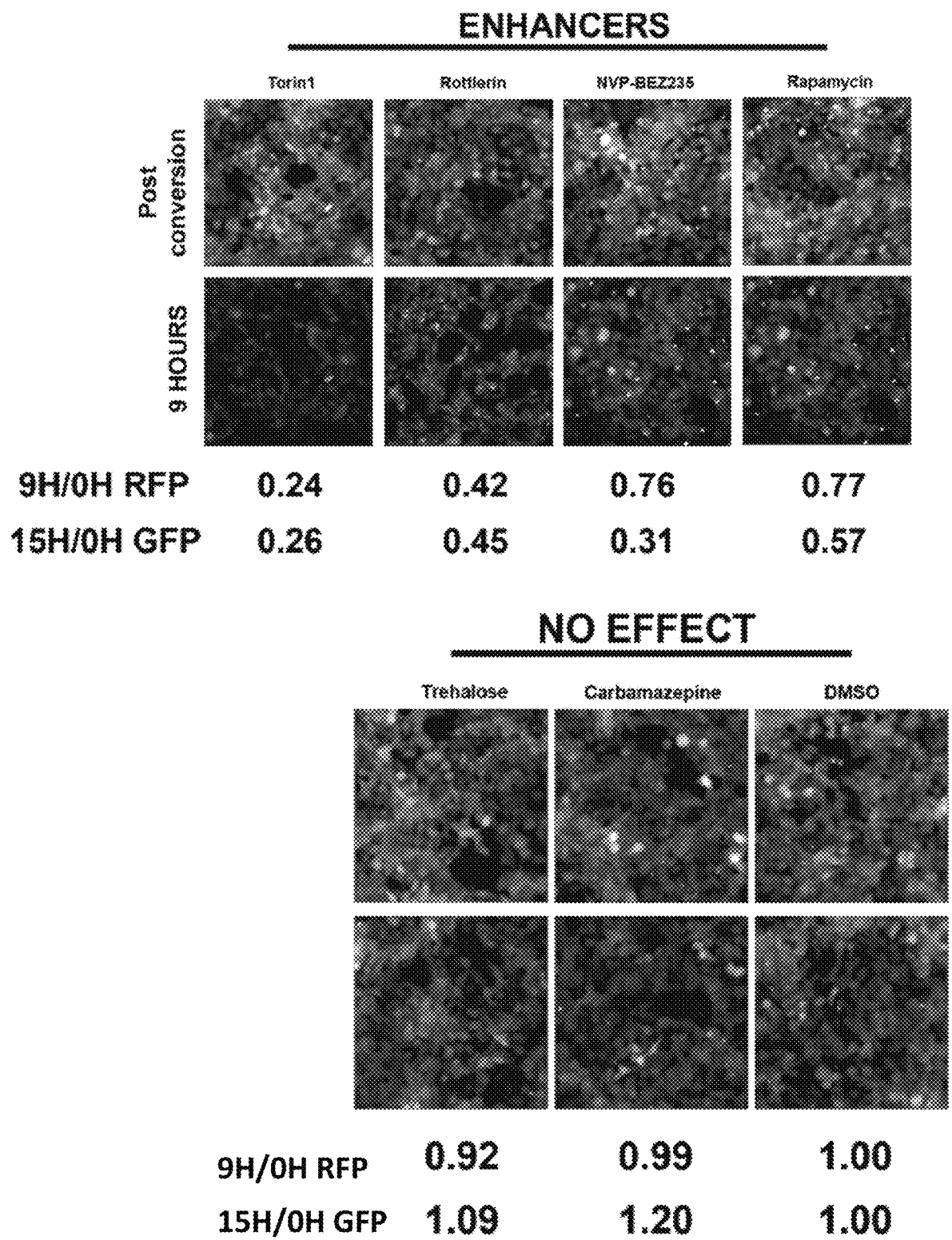
Figure 9C:
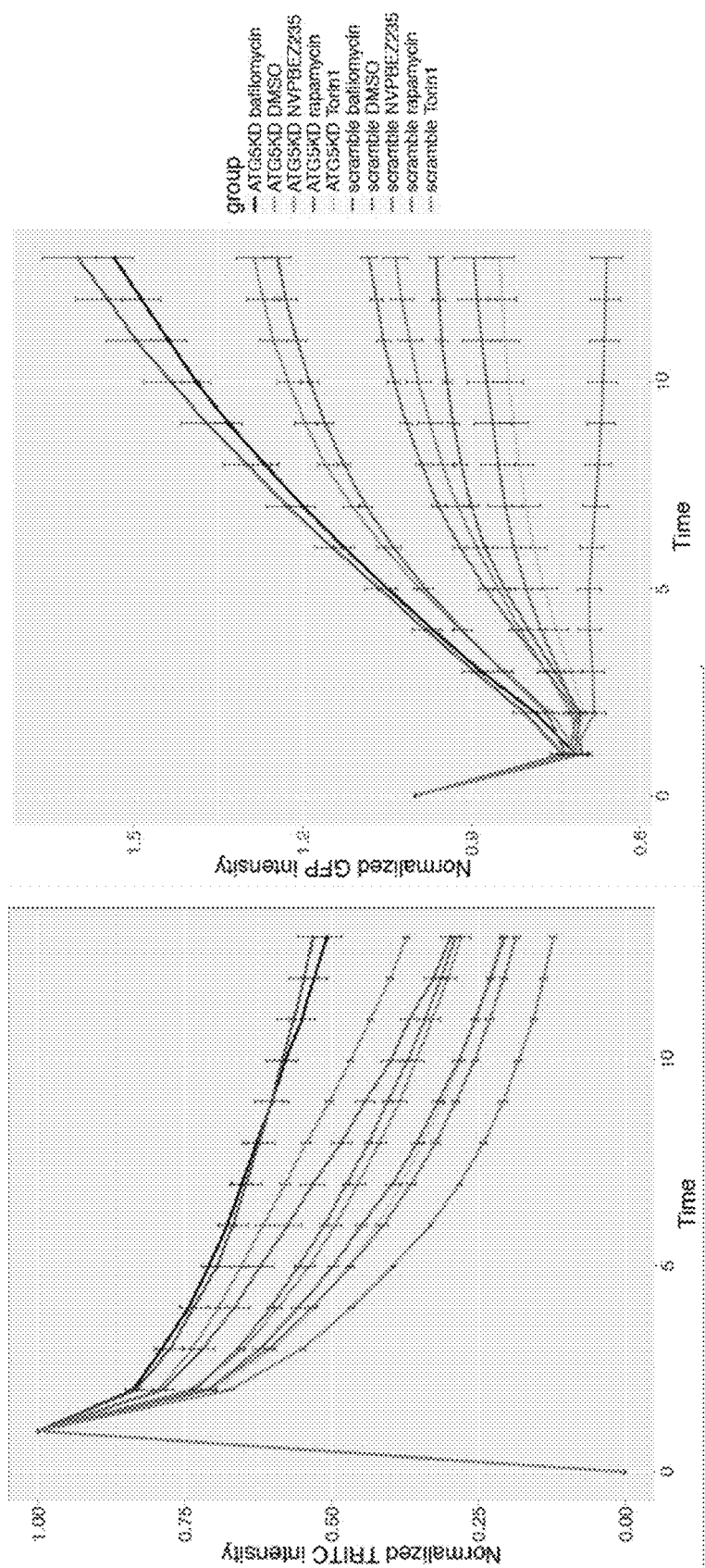
Figure 10A:
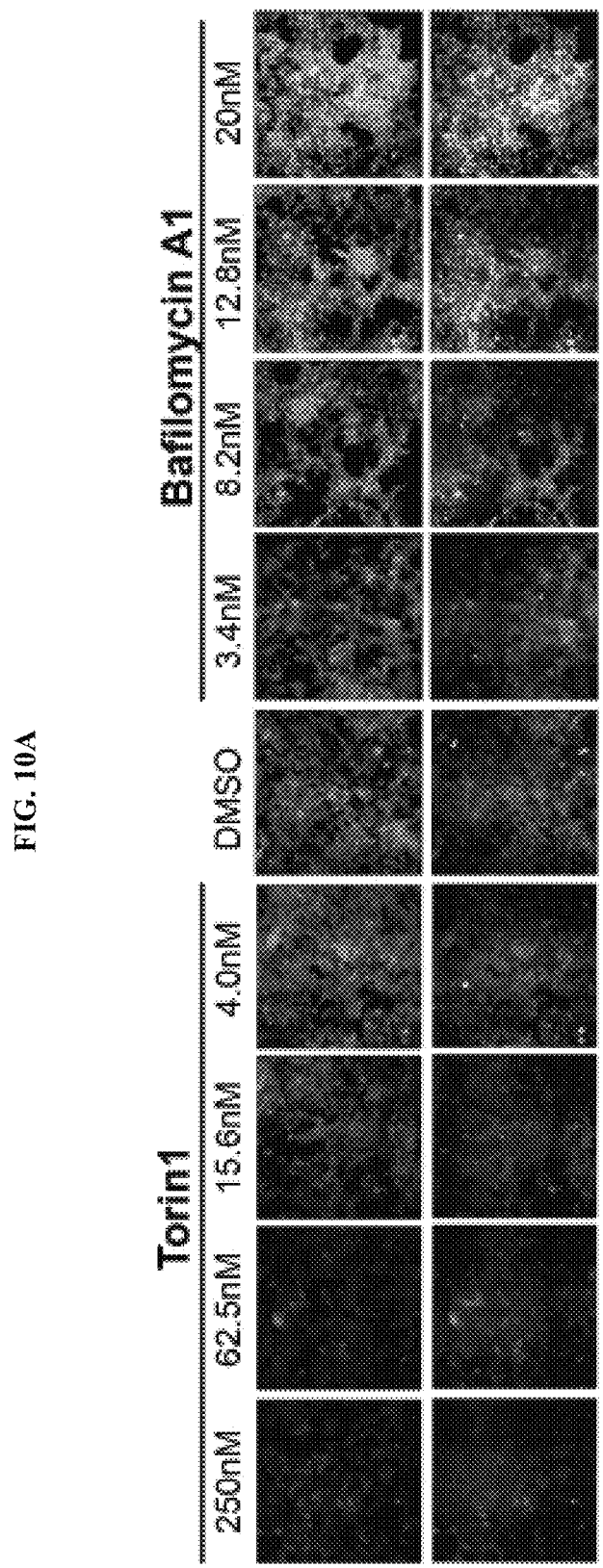
FIGS. 10A-F. Proportional and bidirectional effects of autophagy modulators highlight assay sensitivity.
Figures 10B, 10C:
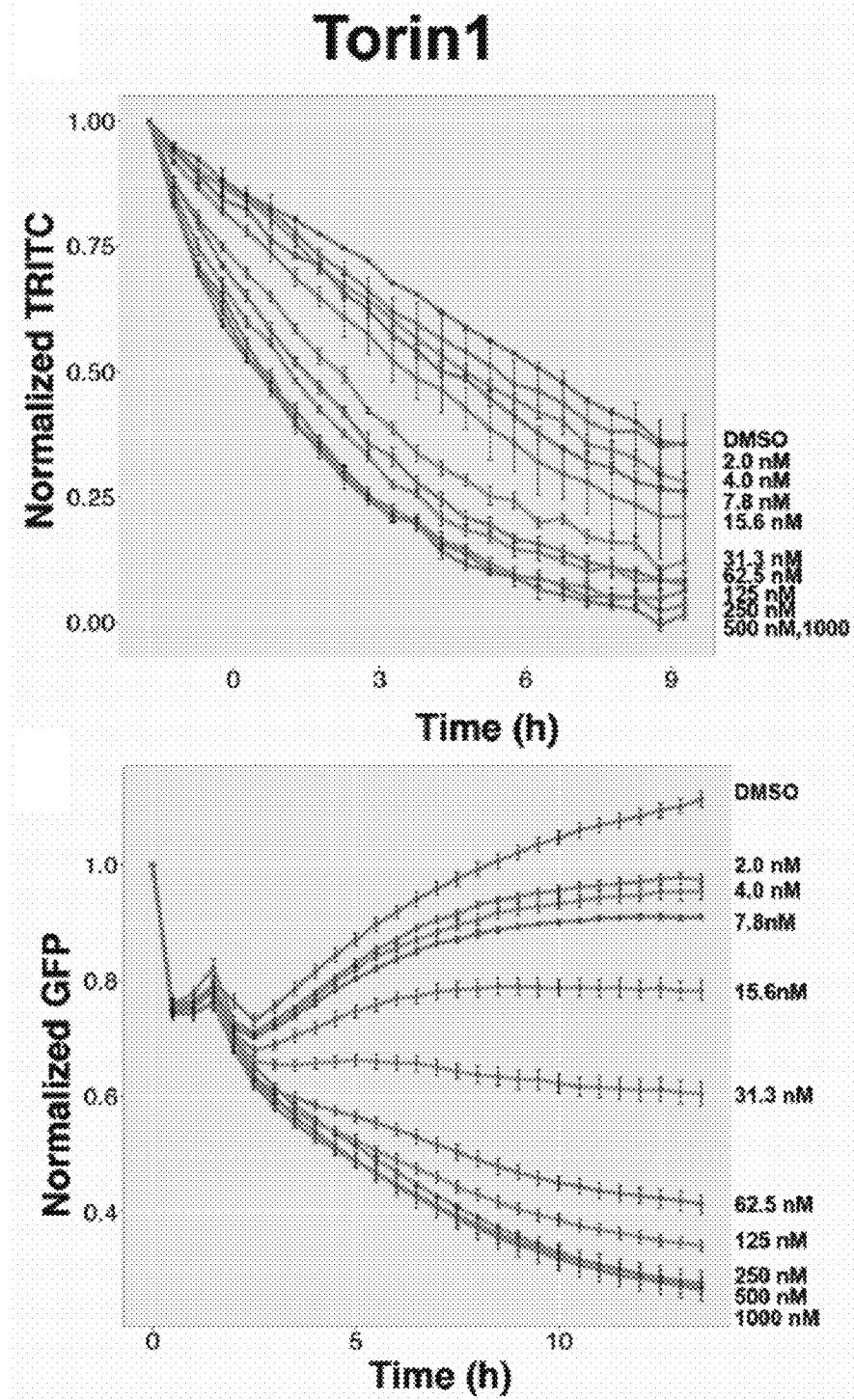
Figures 10D, 10E:
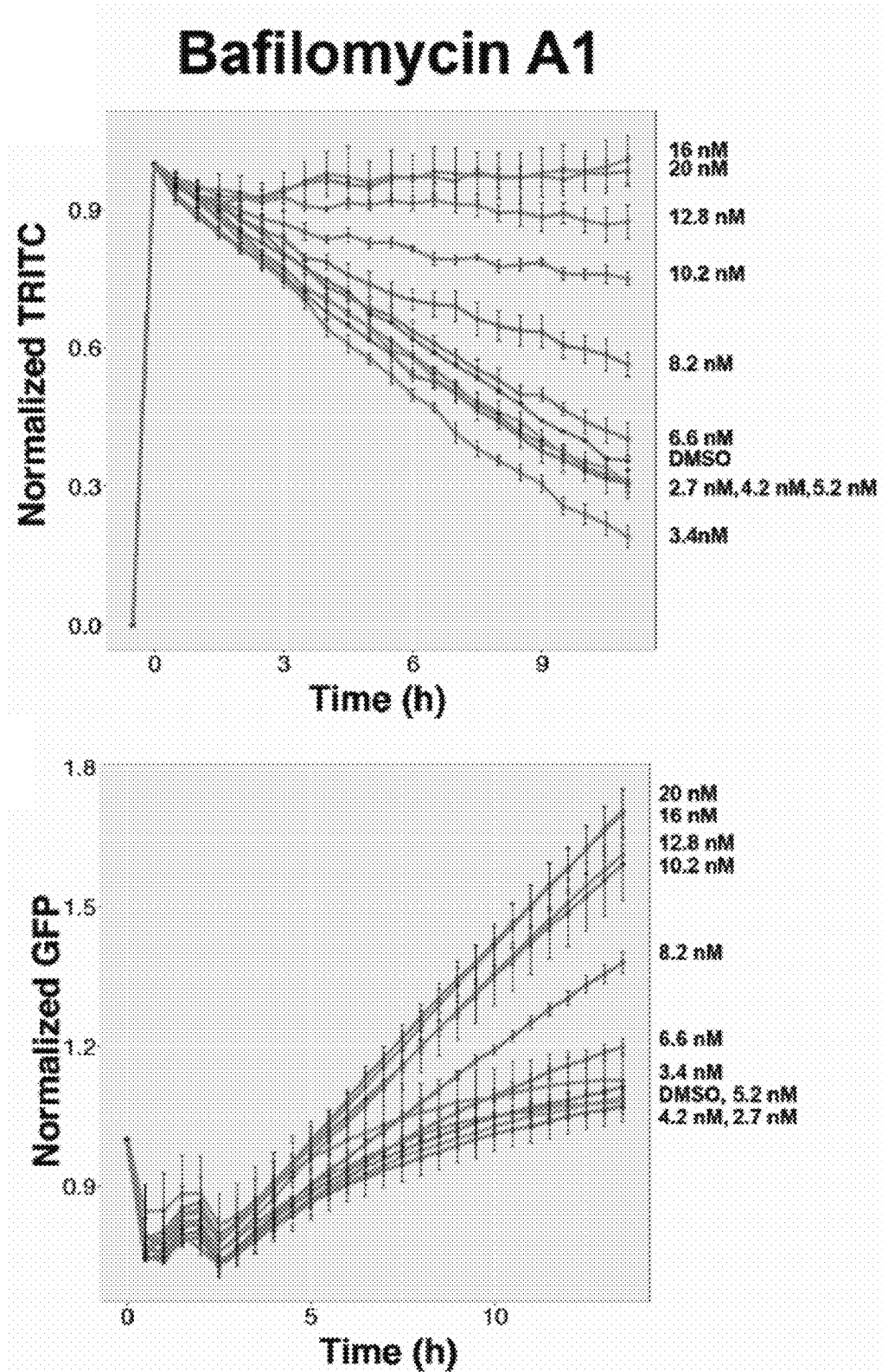
Figure 10F:
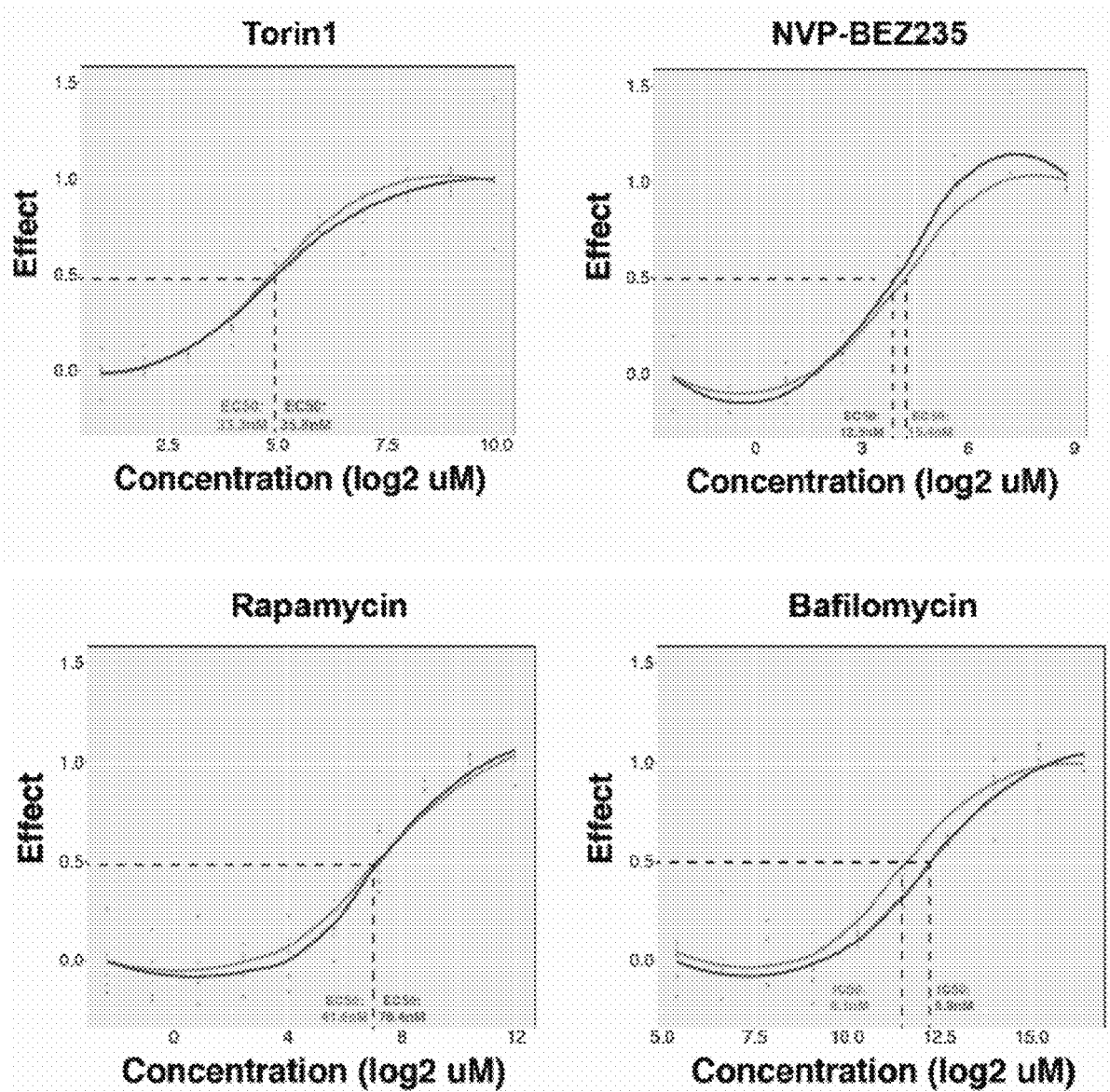
Figure 11A:
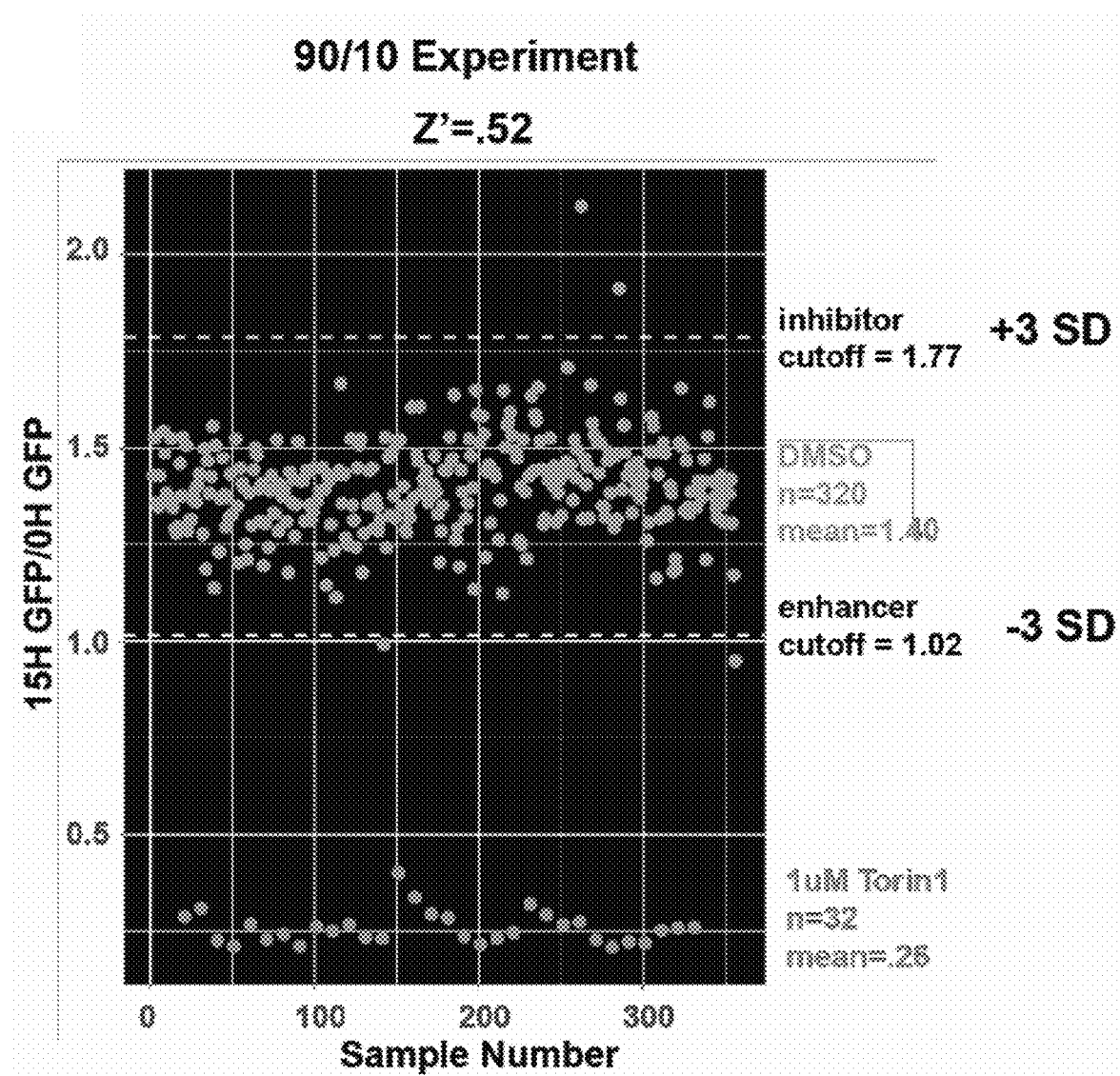
FIGS. 11A-D. Screen of the Prestwick library to detect previously unreported autophagy modulating drugs.
Figure 11B:
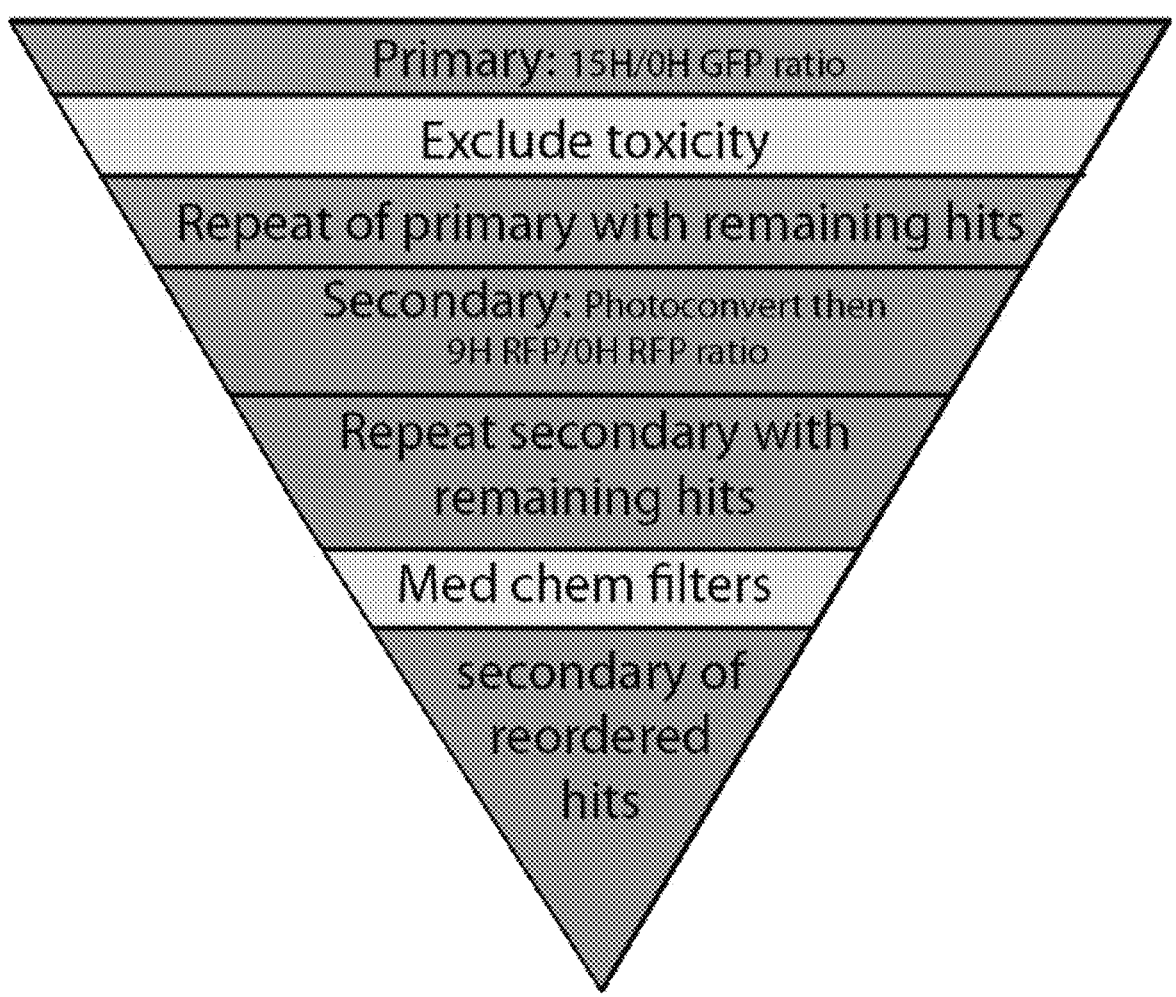
Figure 11C:
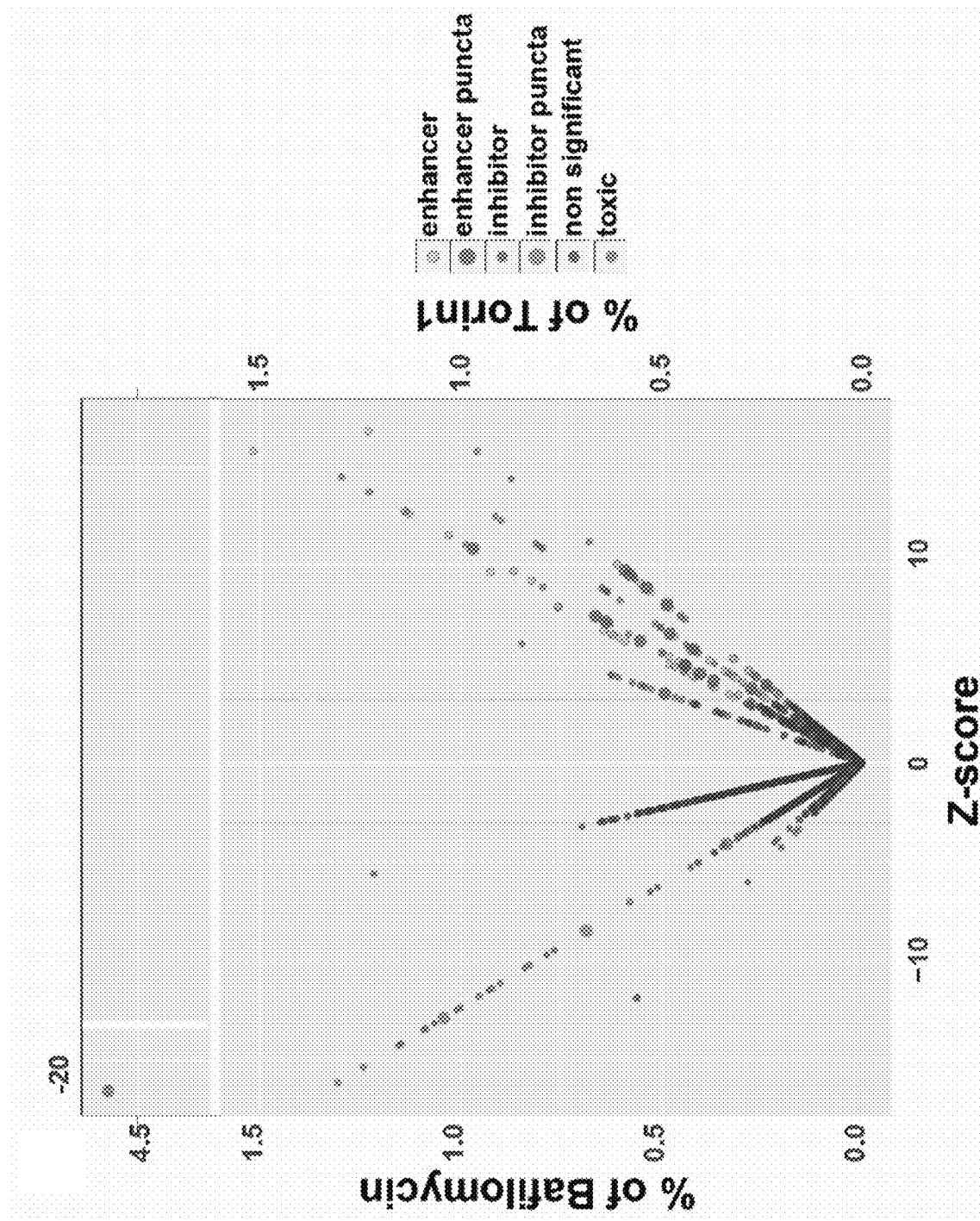
Figure 11D:
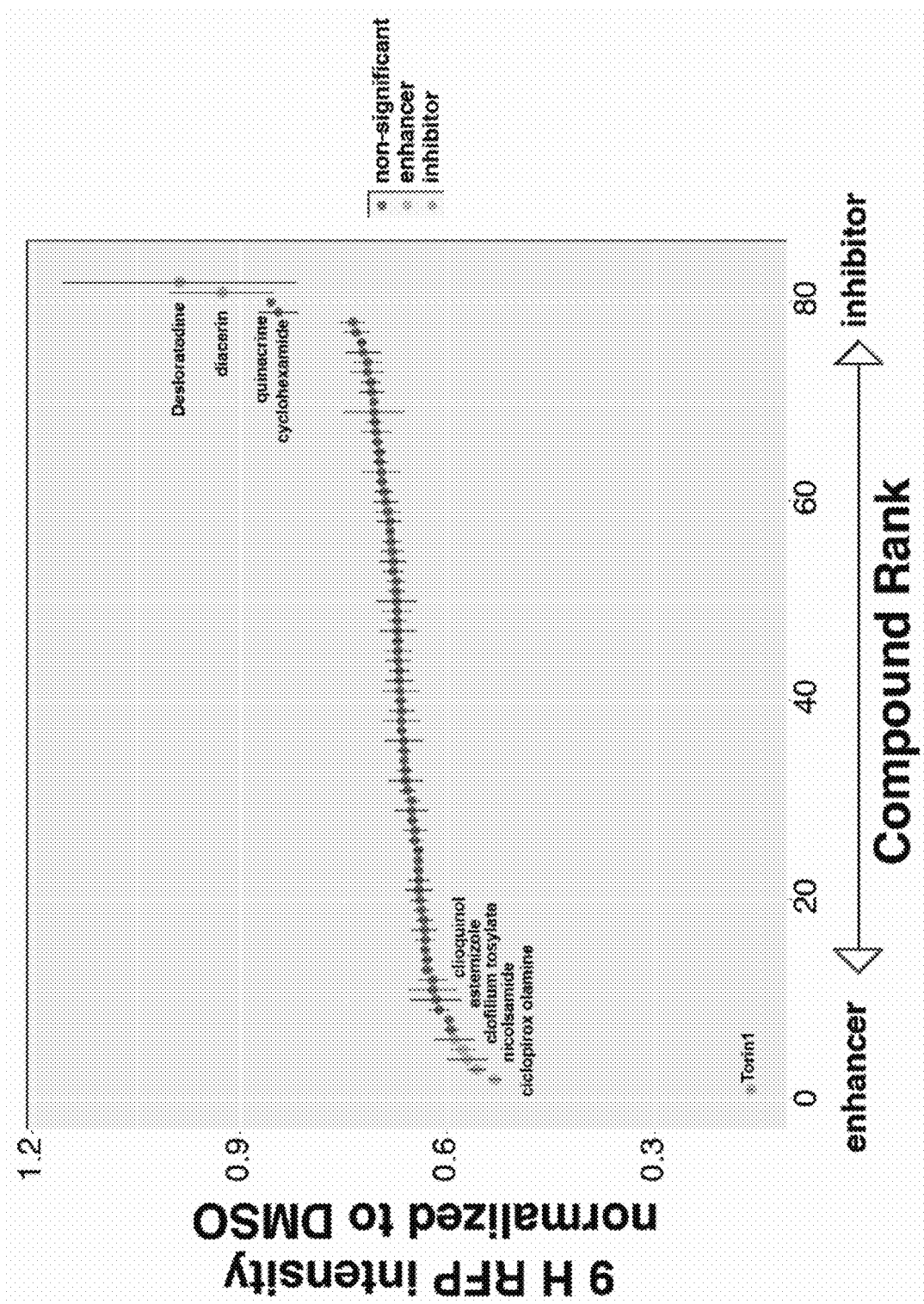
Figure 12A:
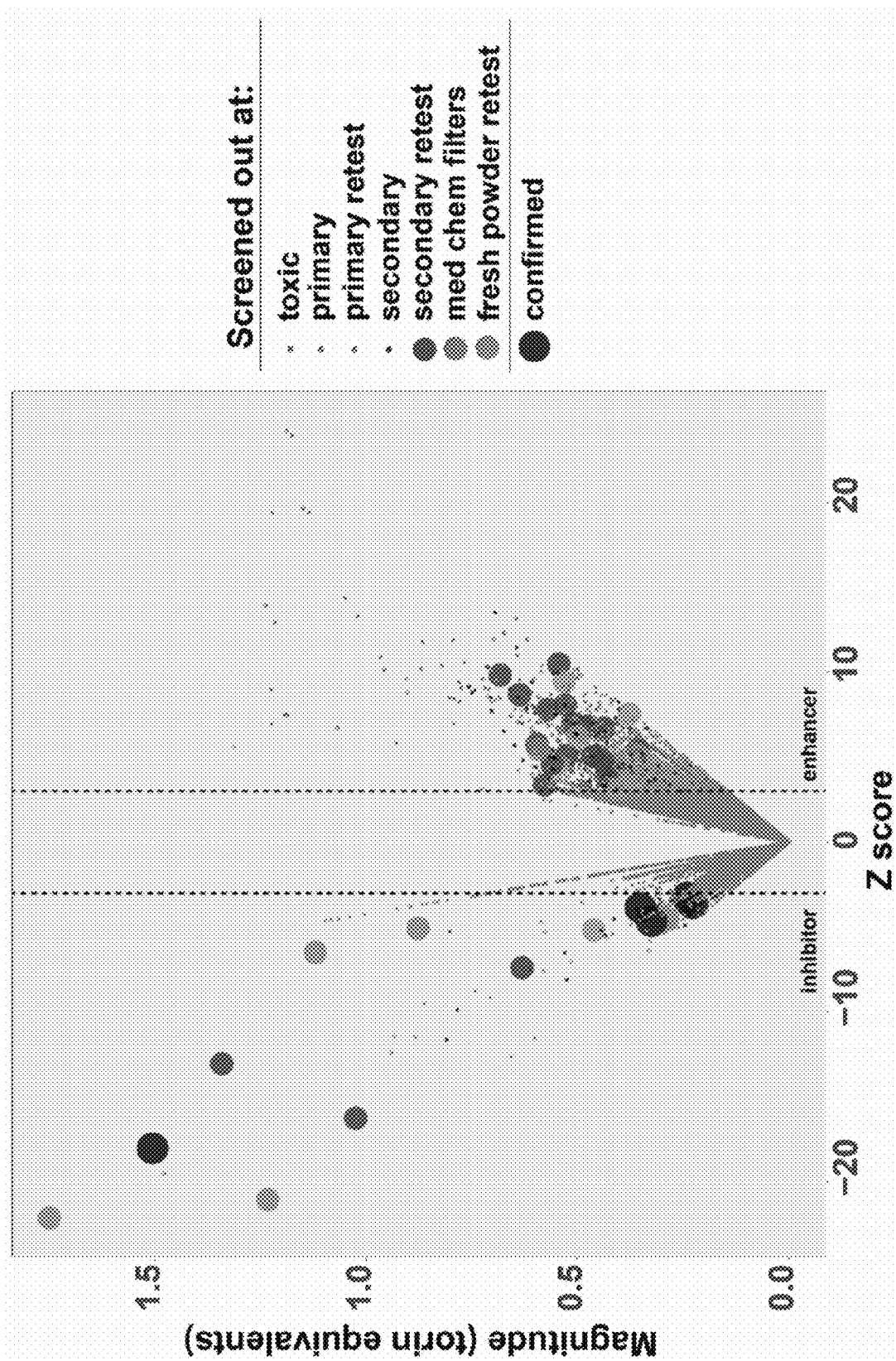
Figure 13A:
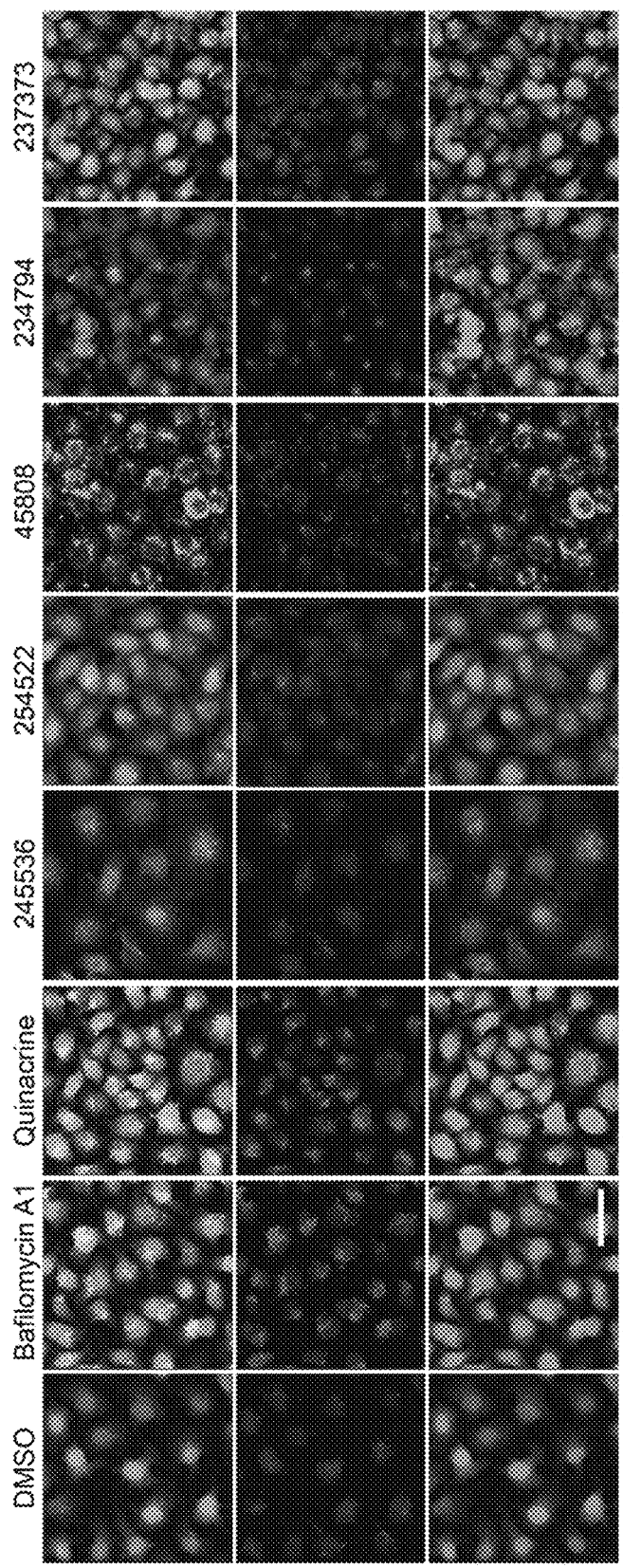
Figure 13B:
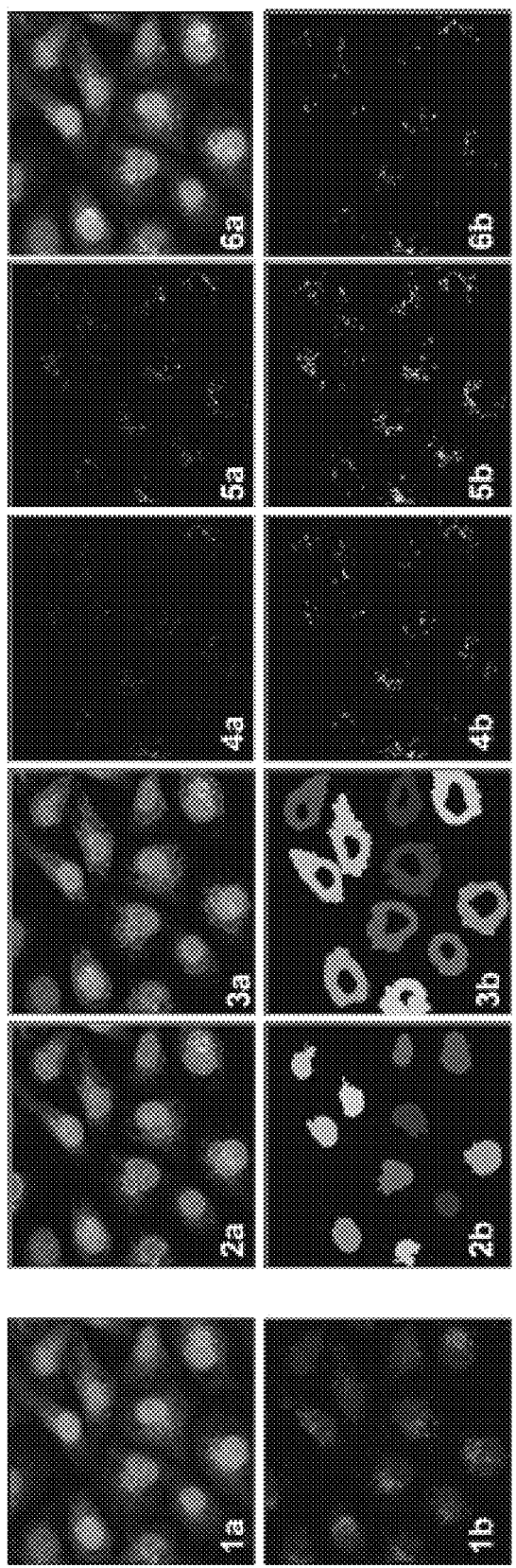
Figure 13C:
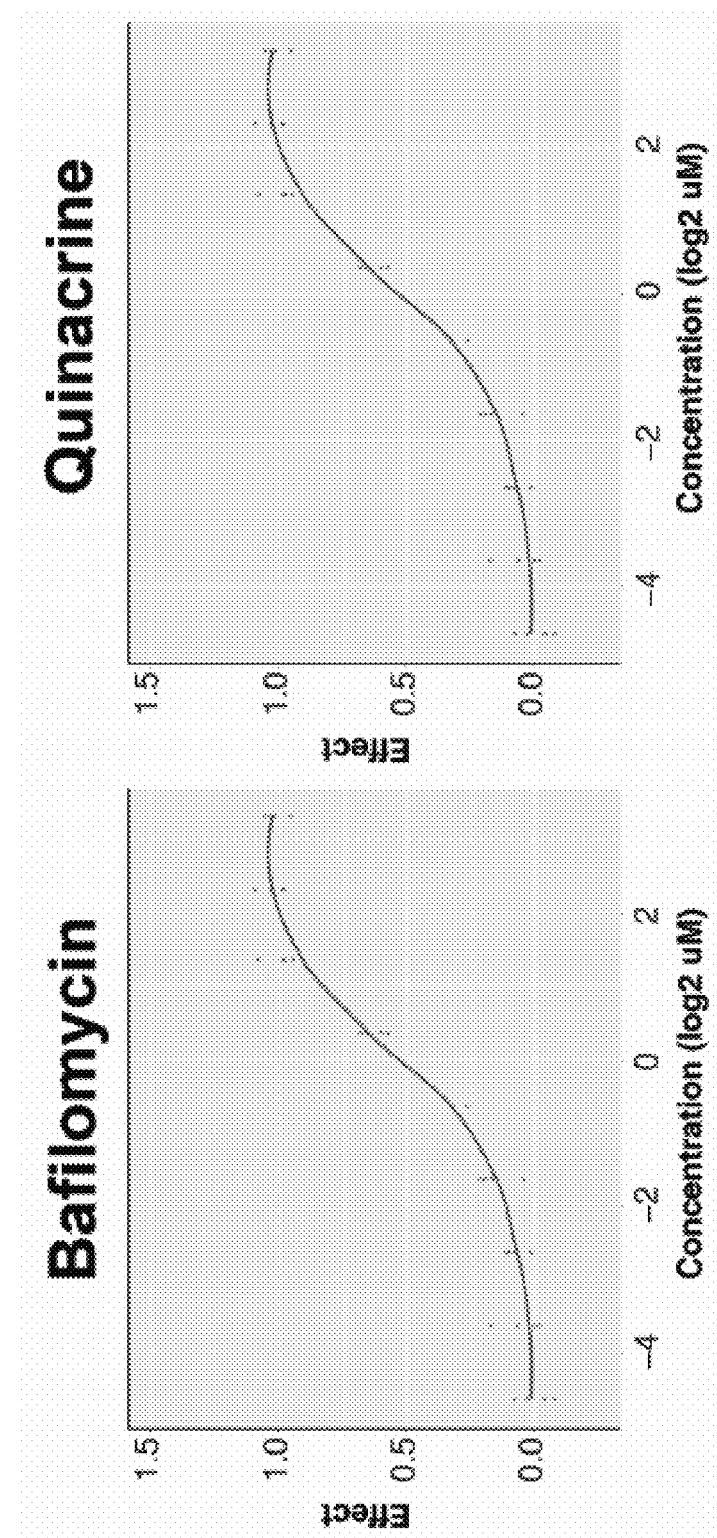
Figure 13C:
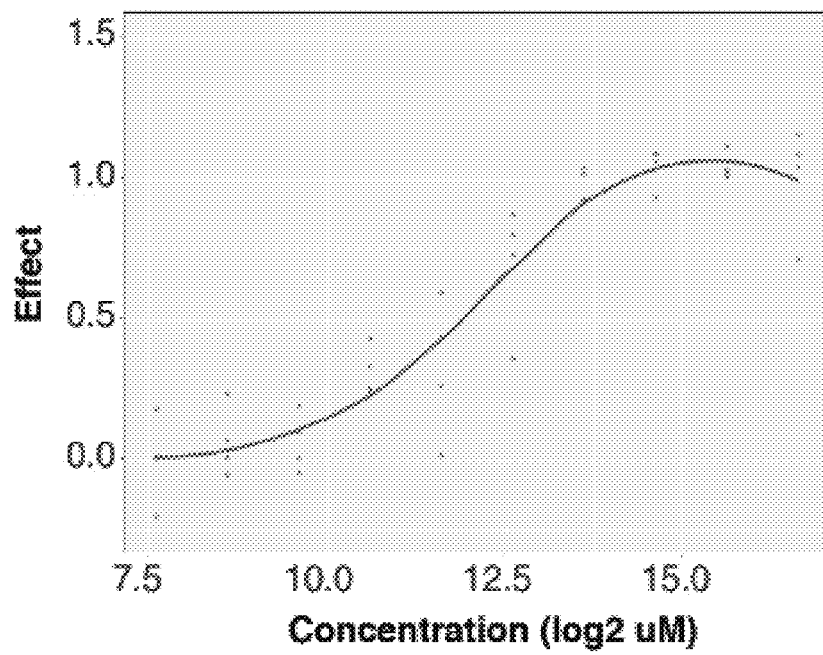
Figure 13C:
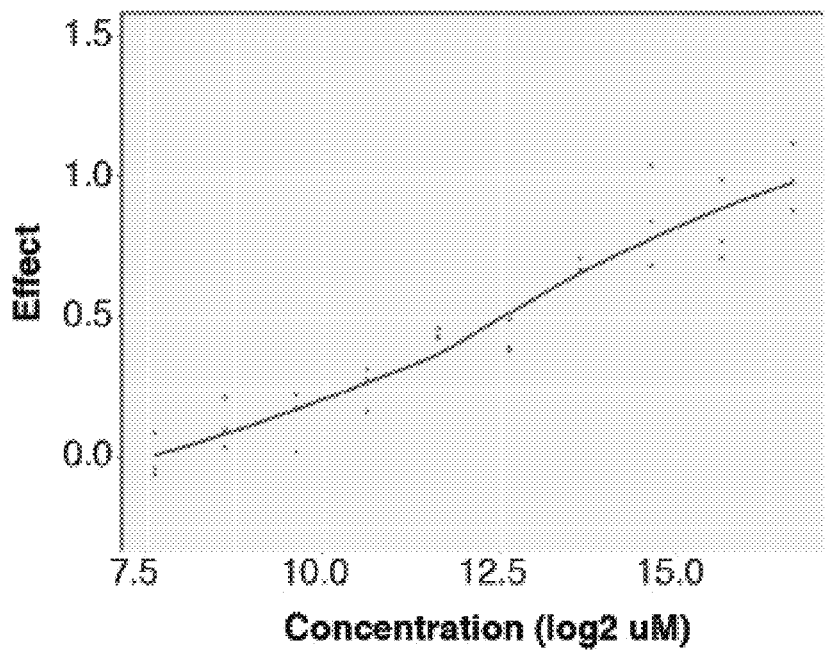
Figure 13C:
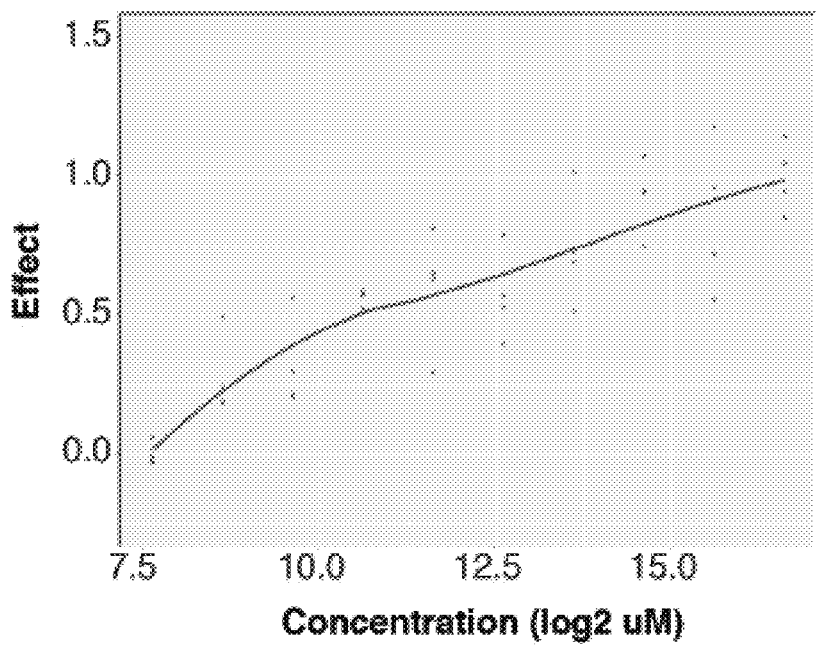
Figure 13C:
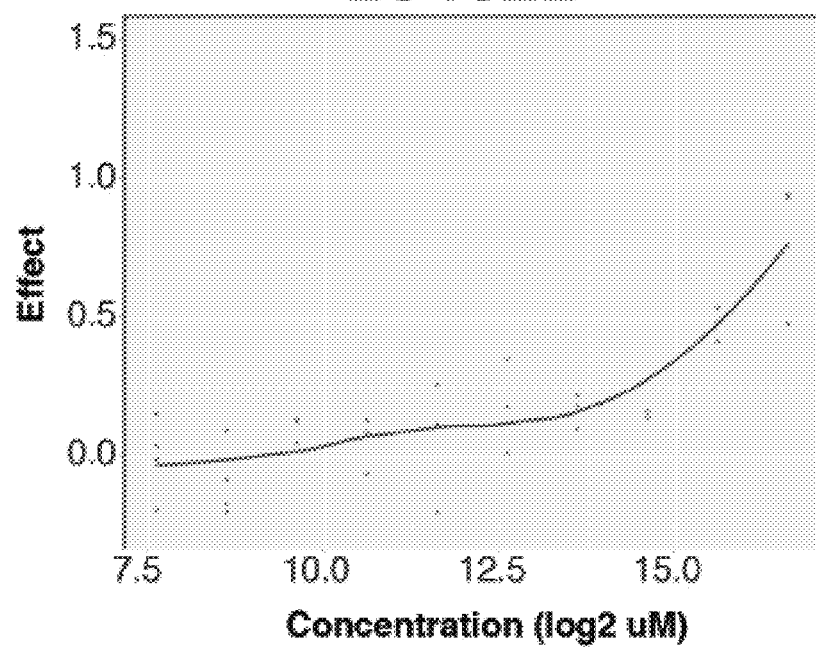
Figure 13C:
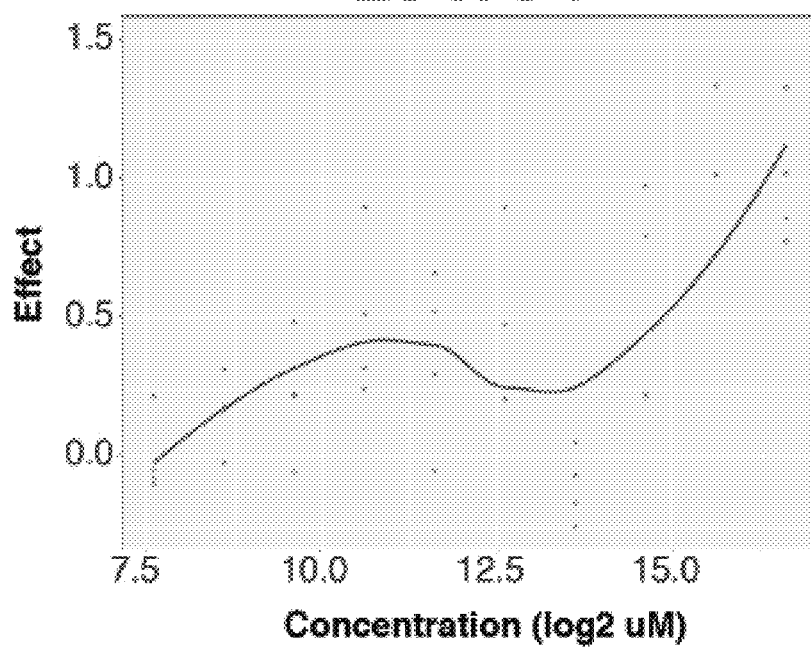
Figure 14A:
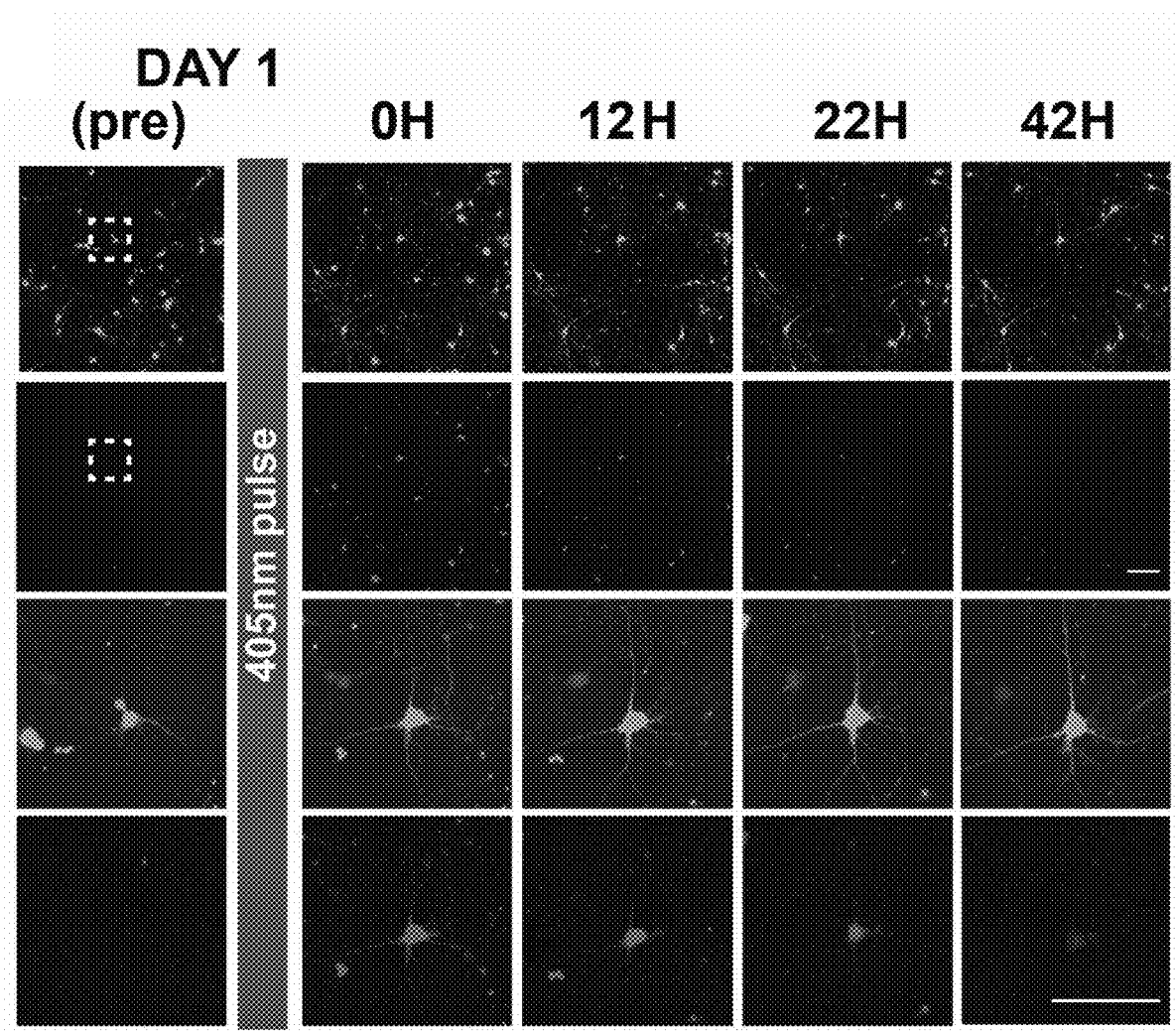
FIG. 14A-D. High rates of basal autophagy predict enhanced survival in primary neurons and enhancing autophagic flux suppresses TDP43 toxicity.
Figure 14B:
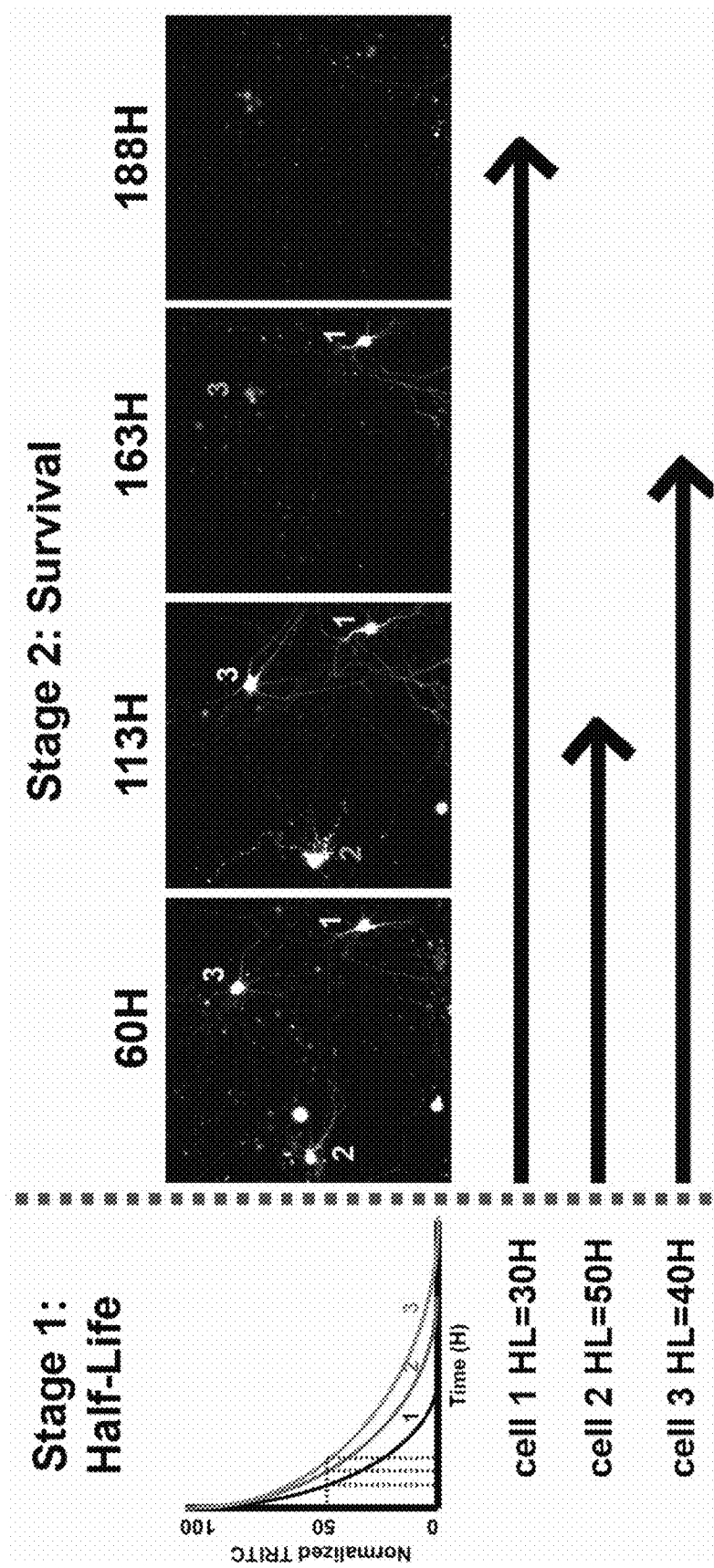
Figure 14C:
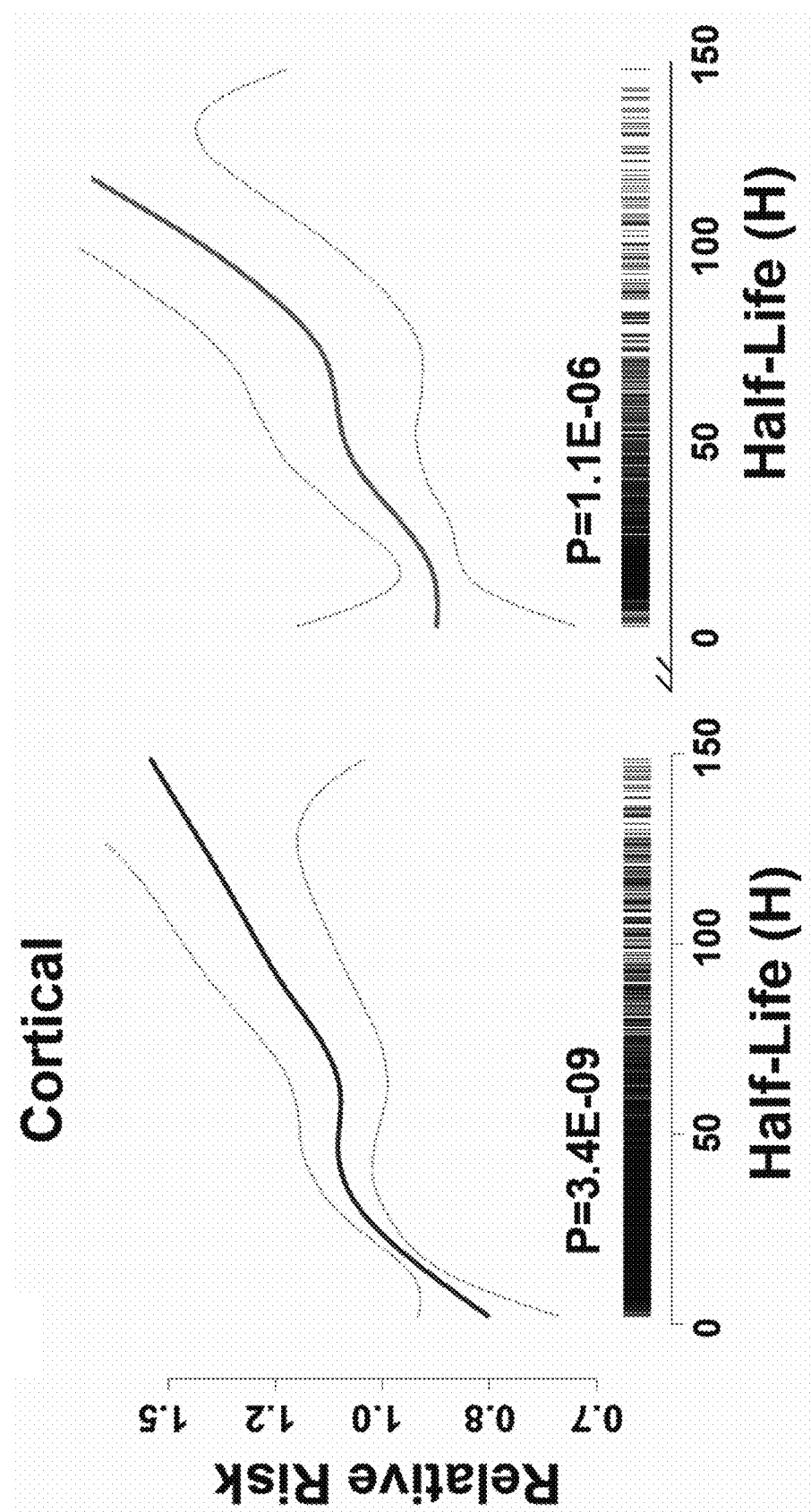
Figure 14D:
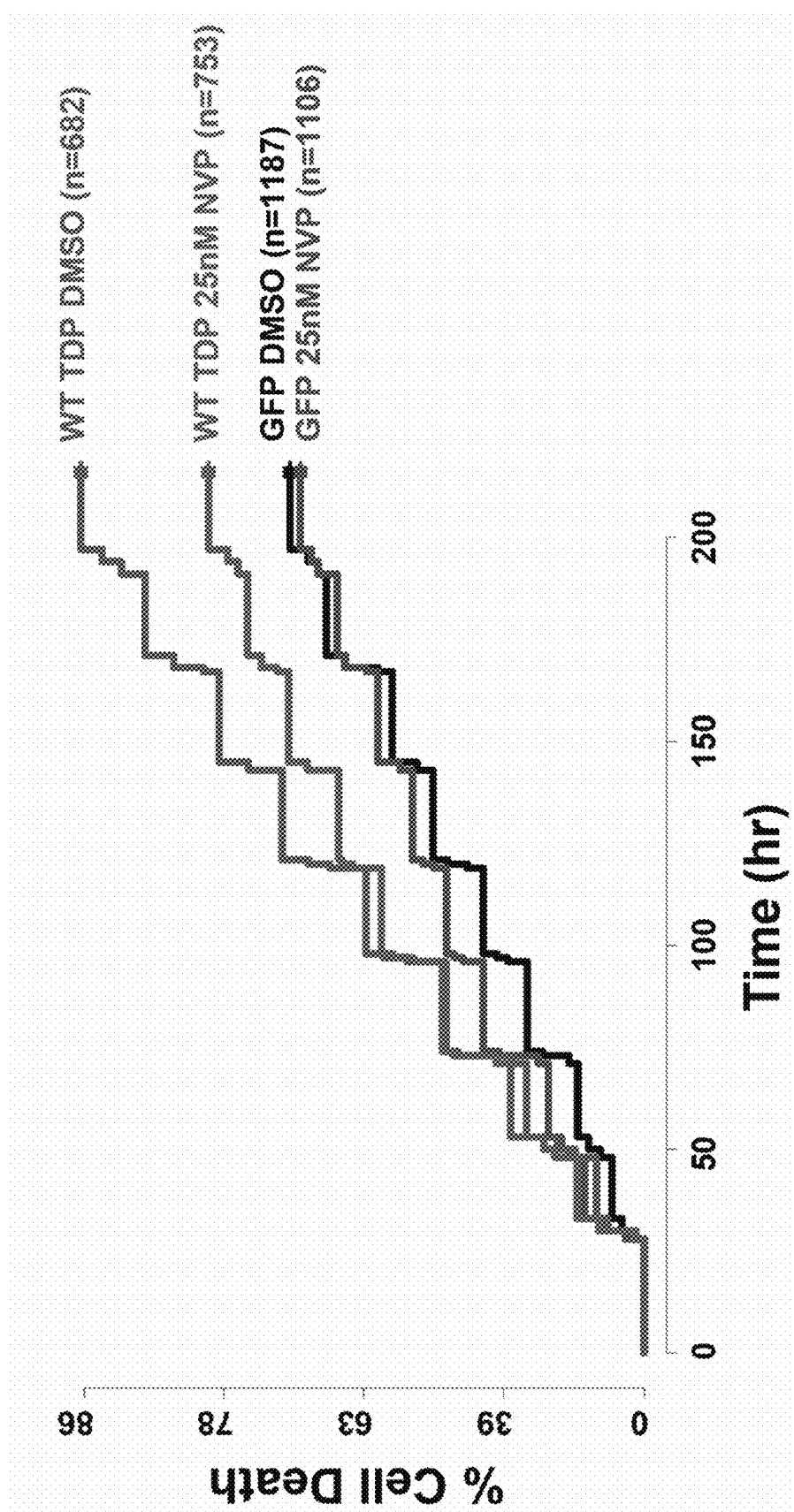
Figure 15:
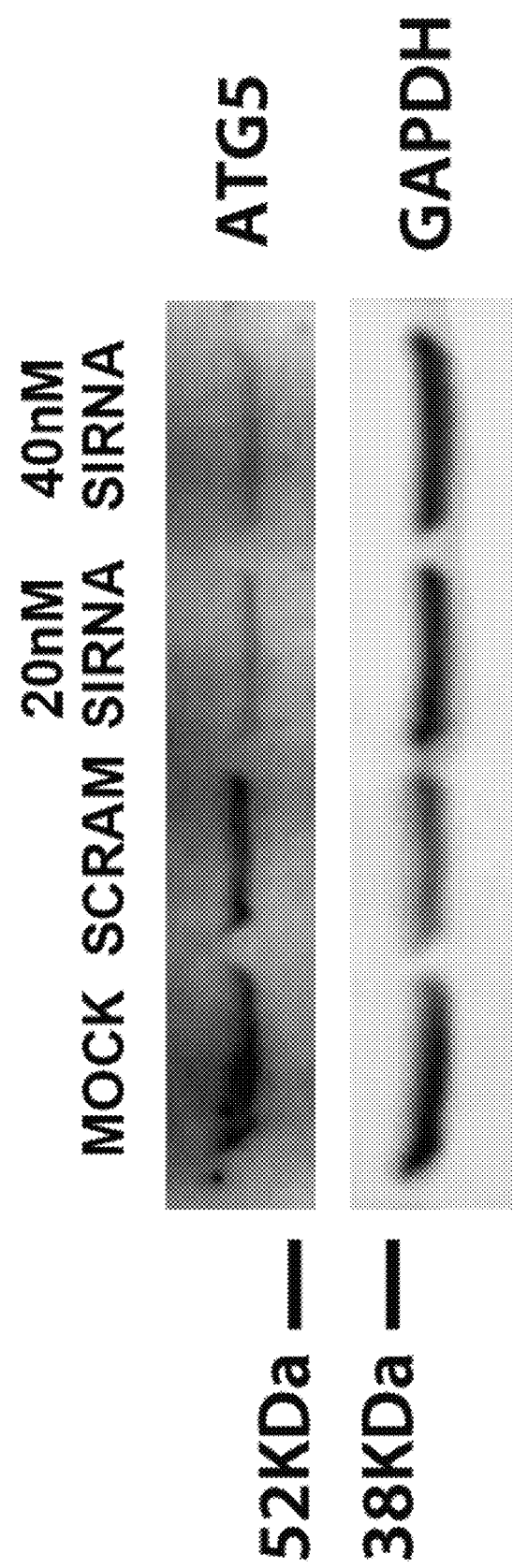
FIG. 15. siRNA knockdown of ATG5. Western blot confirming successful knockdown of ATG5 with 20 nM and 40 nM siRNA. Scramble siRNA at 40 nM.
Figure 16A:
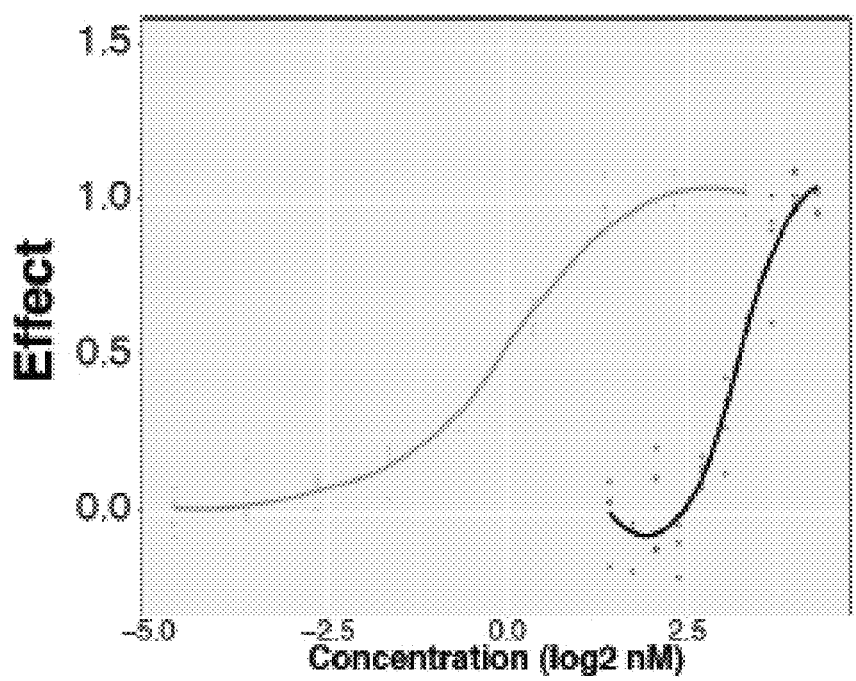
FIGS. 16A-C. Comparison of autophagic flux inhibition in Dendra2-LC3 HEK cells and GFP-RFP-LC3 HeLa cells. Plots depicting dose response relationships for each drug in Dendra-LC3 HEK cells (black) and HeLa GFP-RFP-LC3 cells (blue). In HEK Dendra2-LC3 cells the maximum effect represents the greatest increase in TRITC intensity 14 hours after drug treatment. In HeLa GFP-RFP-LC3 effect represents the % of RFP puncta that are GFP positive, where the greatest and lowest % are set to 1.0 and 0, respectively. Concentration is plotted in nM on a log(2) scale.
Figure 16A:
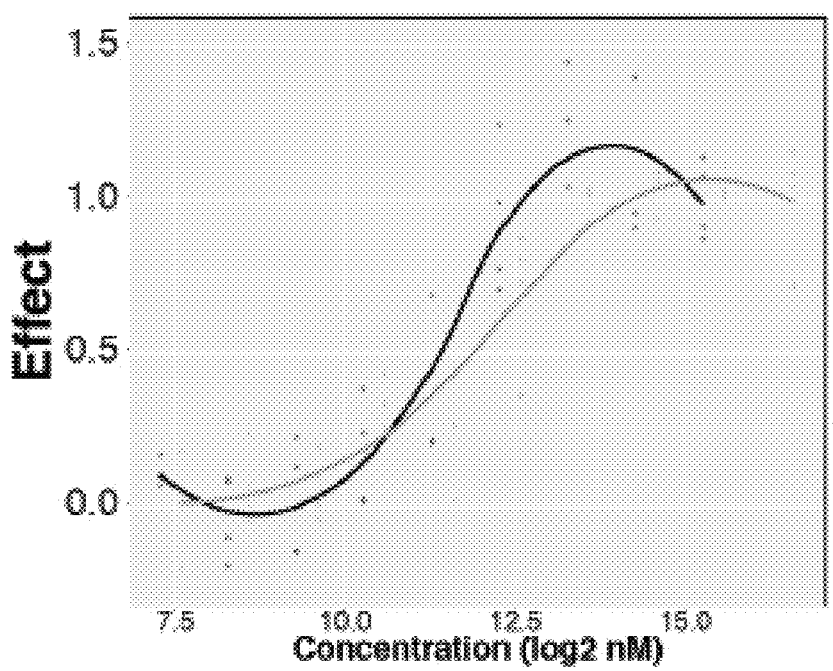
Figure 16B:
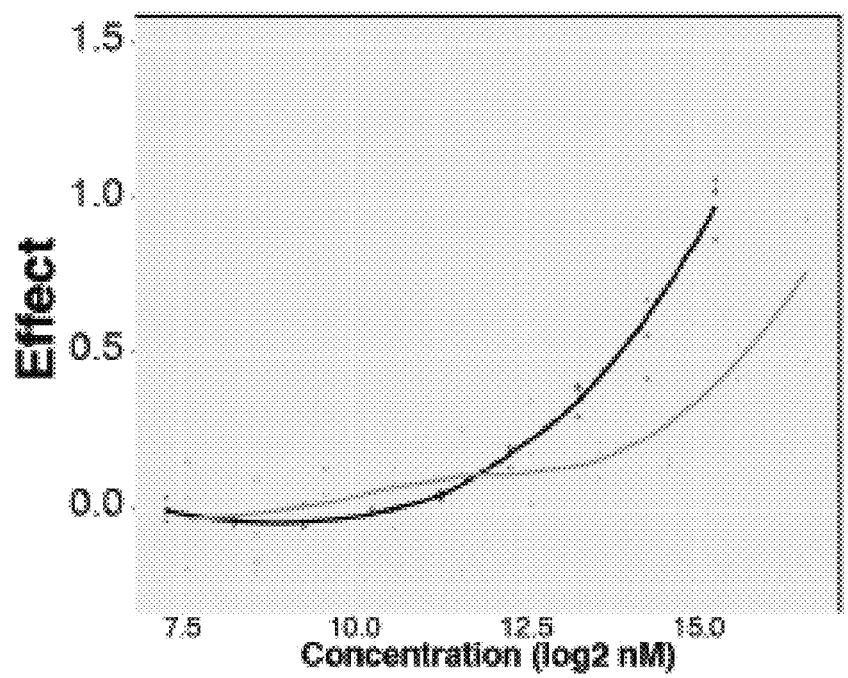
Figure 16B:
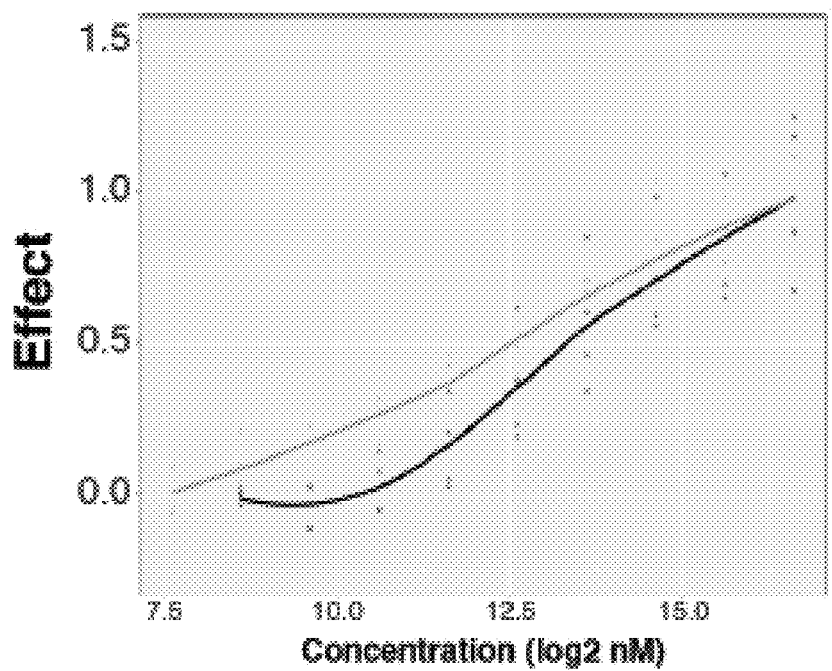
Figure 16C:
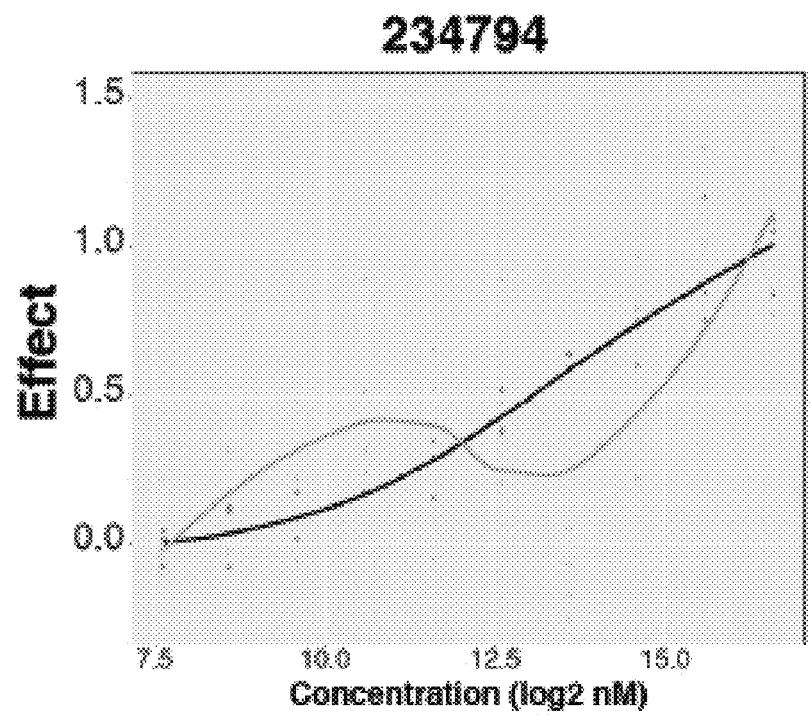
Figure 16C:
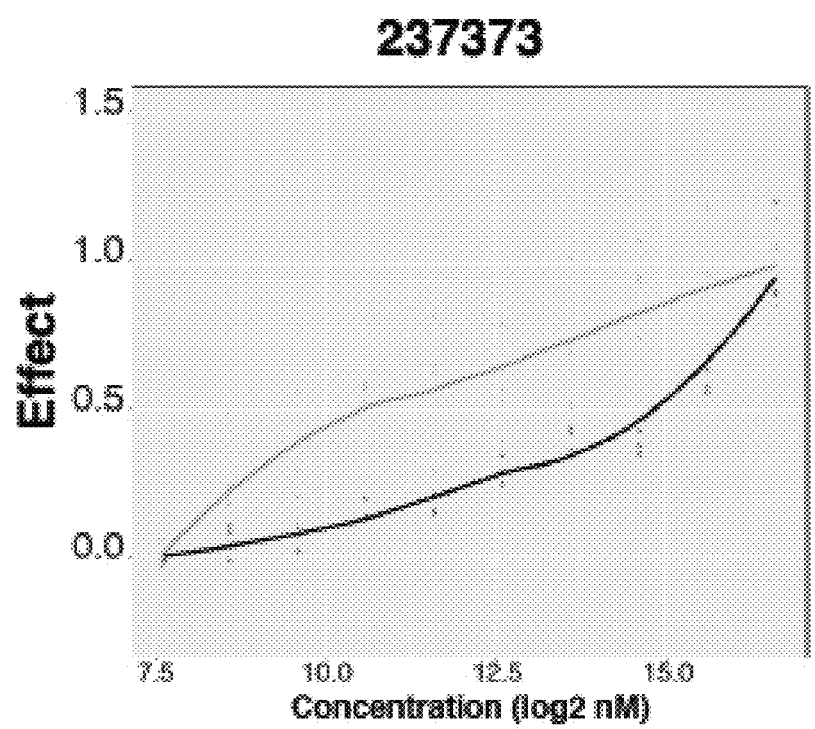
Figure 17:
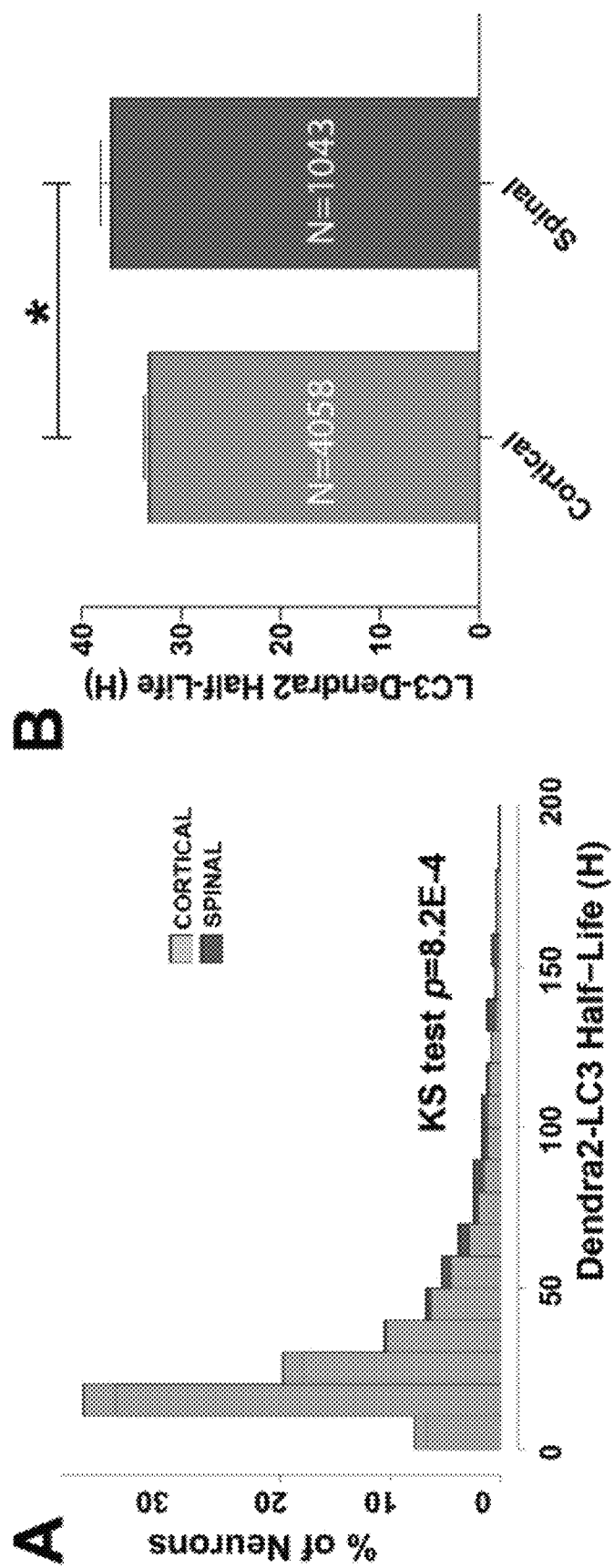
FIG. 17, panels A-B. (Panel A) Histogram depicting single cell Dendra2-LC3 half-lives in cortical and spinal neurons. Relative to spinal neurons (n=1043), a leftward shift was observed in the half-life distribution of cortical neurons (n=4058) indicating a greater frequency of cells exhibiting high rates of autophagic flux ($p=8.2E-4$, two-sample Kolmogorov-Smirnov (KS) test). (Panel B) Cortical neurons showed a lower mean single-cell Dendra2-LC3 half-life (33.2H) than spinal neurons (37.1H) ($p=7.1E-4$, Welch two sample t-test).

Experiments are conducted to assess the ability of compounds to stimulate or inhibit autophagy in Dendra2-LC3 HEK cells that are transfected with siRNA targeting ATG5, a crucial component required for LC3 maturation and autophagy initiation (Ref. 28; herein incorporated by reference in its entirety). ATG5 knockdown (FIG. 6a) mitigated the autophagy-inducing effects of torin1, as determined by imaging in both the red and green channels (FIG. 6b, c). A similar strategy is used to verify that compounds identified in phases I and II are, in fact, true autophagy inducers and inhibitors.

Example 2

Establishing Structure-Activity Relationships for Lead Compound Optimization

Experiments are conducted to identify the specific chemical or pharmacologic properties significantly associated with autophagy activity through rational and statistical modeling approaches. Autophagy inducers and inhibitors emerging screening are ranked in terms of their ability to stimulate or inhibit autophagy. A structure-activity relationship (SAR) table is assembled for these compounds (Ref. 15; herein incorporated by reference in its entirety), listing potentially relevant chemical properties and variables, as well as the normalized GFP ratio (T15/T0) and RFP ratio (T9/T0) indicating their effects on autophagy flux (FIG. 3c, d). Because a goal is to develop molecules for treating neurodegenerative disorders, a series of parameters that predict blood-brain permeability, including pH-adjusted lipophilicity (c Log D), molecular weight, polar surface area, available hydrogen bond donors, and ionization (pKa), etc. is also included. Linear and non-linear correlation analyses are applied to determine if specific properties predict autophagic flux. In addition to these statistical modeling approaches, visual inspection is valuable in linking important structural features to predicted autophagic activity.

Once the relevant structural and chemical variables have been defined, compounds that emphasize the properties most highly associated with autophagy induction or inhibition are selected. These test compounds are evaluated by OPL in Dendra2-LC3 HEK cells (FIG. 3c, d) for their ability to stimulate or inhibit autophagy, and the resulting normalized GFP (T15/T0) and RFP (T9/T0) ratios fed back into the SAR model for iterative refinement. Depending on the resulting activity and the availability of desired structural/chemical properties in commercially available libraries, a second round of SAR screening may be performed. Alternatively, a rational design of more active compounds may be developed through medicinal chemistry.

REFERENCES

The following references, some of which are cited above by number, are herein incorporated by reference in their entireties.

1 Charcot, J. M. & Joffory, A. Deux cas d'atrophie musculaire progressive avec lesions de la substance grise et des faisceaux antero-lateraux de la moelle epiniere. Arch. Physiol. Neurol. Pathol. 2, 744-754 (1869).
2. Murphy, J. M. et al. Continuum of Frontal Lobe Impairment in Amyotrophic Lateral Sclerosis. Arch Neurol 64, 530 (2007).
3. Lillo, P., Savage, S., Mioshi, E., Kiernan, M. C. & Hodges, J. R. Amyotrophic lateral sclerosis and frontotemporal dementia: A behavioural and cognitive continuum. Amyotroph Lateral Scler 13, 102-109 (2012).
4. Xu, Z., Alruwaili, A. R. S., Henderson, R. D. & McCombe, P. A. Screening for cognitive and behavioural impairment in amyotrophic lateral sclerosis: Frequency of abnormality and effect on survival. J Neurol Sci 376, 16-23 (2017).
5. Burrell, J. R., Kiernan, M. C., Vucic, S. & Hodges, J. R. Motor Neuron dysfunction in frontotemporal dementia. Brain 134, 2582-2594 (2011).
6. Neumann, M. et al. Ubiquitinated TDP-43 in frontotemporal lobar degeneration and amyotrophic lateral sclerosis. Science 314, 130-133 (2006).
7 Al-Chalabi, A. et al. The genetics and neuropathology of amyotrophic lateral sclerosis. Acta Neuropathol 124, 339-352 (2012).
8. Renton, A. E., Chió, A. & Traynor, B. J. State of play in amyotrophic lateral sclerosis genetics. Nat. Neurosci. 17, 17-23 (2013).
9. White, M. A. & Sreedharan, J. Amyotrophic lateral sclerosis. Curr Opin Neurol 29, 557-564 (2016).
10. Hara, T. et al. Suppression of basal autophagy in neural cells causes neurodegenerative disease in mice. Nat Cell Biol 441, 885-889 (2006).
11. Komatsu, M. et al. Loss of autophagy in the central nervous system causes neurodegeneration in mice. Nature 441, 880-884 (2006).
12. Lee, S., Sato, Y. & Nixon, R. A. Lysosomal Proteolysis Inhibition Selectively Disrupts Axonal Transport of Degradative Organelles and Causes an Alzheimer's-Like Axonal Dystrophy. J Neurosci 31, 7817-7830 (2011).
13. Wang, I.-F. et al. Autophagy activators rescue and alleviate pathogenesis of a mouse model with proteinopathies of the TAR DNA-binding protein 43. Proc. Natl. Acad. Sci. U.S.A. 109, 15024-15029 (2012).
14. Barmada, S. J. et al. Autophagy induction enhances TDP43 turnover and survival in neuronal ALS models. Nat. Chem. Biol. 10, 677-685 (2014).
15. Tsvetkov, A. S. et al. A small-molecule scaffold induces autophagy in primary neurons and protects against toxicity in a Huntington disease model. Proc. Natl. Acad. Sci. U.S.A. 107, 16982-16987 (2010).
16. Hetz, C. et al. XBP-1 deficiency in the nervous system protects against amyotrophic lateral sclerosis by increasing autophagy. Genes Dev 23, 2294-2306 (2009).
17. Cheng, C.-W., Lin, M.-J. & Shen, C.-K. J. Rapamycin Alleviates Pathogenesis of a New *Drosophila* Model of ALS-TDP. J Neurogenet 1-47 (2015). doi:10.3109/01677063.2015.1077832
18. Cuervo, A. M. & Dice, J. F. Age-related decline in chaperone-mediated autophagy. J Biol Chem 275, 31505-31513 (2000).
19. Donati, A. et al. Age-related changes in the regulation of autophagic proteolysis in rat isolated hepatocytes. J. Gerontol. A Biol. Sci. Med. Sci. 56, B288-93 (2001).
20. Brunk, U. T. & Terman, A. Lipofuscin: mechanisms of age-related accumulation and influence on cell function. Free Radic. Biol. Med. 33, 611-619 (2002).

21. Terman, A. The effect of age on formation and elimination of autophagic vacuoles in mouse hepatocytes. Gerontology 41 Suppl 2, 319-326 (1995).
22. Vittorini, S. et al. The age-related accumulation of protein carbonyl in rat liver correlates with the age-related decline in liver proteolytic activities. J. Gerontol. A Biol. Sci. Med. Sci. 54, B318-23 (1999).
23. Ciechanover, A. & Kwon, Y. T. Degradation of misfolded proteins in neurodegenerative diseases: therapeutic targets and strategies. Exp. Mol. Med. 47, e147 (2015).
24. Cuervo, A. M. Autophagy and aging: keeping that old broom working. Trends Genet 24, 604-612 (2008).
25. Cuervo, A. M. & Wong, E. Chaperone-mediated autophagy: roles in disease and aging. Cell Res. 24, 92-104 (2014).
26. Wong, E. & Cuervo, A. M. Integration of clearance mechanisms: the proteasome and autophagy. Cold Spring Harbor Persp Biol 2, a006734 (2010).
27. Klionsky, D. J. et al. Guidelines for the use and interpretation of assays for monitoring autophagy (3rd edition). Autophagy 12, 1-222 (2016).
28. Rubinsztein, D. C., Shpilka, T. & Elazar, Z. Mechanisms of Autophagosome Biogenesis Minireview. Curr Biol 22, R29-R34 (2012).
29. Ran, F. A. et al. Double nicking by RNA-guided CRISPR Cas9 for enhanced genome editing specificity. Cell 154, 1380-1389 (2013).
30. Cong, L. et al. Multiplex genome engineering using CRISPR/Cas systems. Science 339, 819-823 (2013).
31. Kabeya, Y. et al. LC3, a mammalian homologue of yeast Apg8p, is localized in autophagosome membranes after processing. EMBO J. 19, 5720-5728 (2000).
32. Chudakov, D. M., Lukyanov, S. & Lukyanov, K. A. Tracking intracellular protein movements using photoswitchable fluorescent proteins PS-CFP2 and Dendra2. Nat Protoc 2, 2024-2032 (2007).
33. Chudakov, D. M., Lukyanov, S. & Lukyanov, K. A. Using photoactivatable fluorescent protein Dendra2 to track protein movement. BioTechniques 42, 553-555-557 passim (2007).
34. Tsvetkov, A. S. et al. proteostasis of polyglutamine varies among neurons and predicts neurodegeneration. Nat. Chem. Biol. 9, 586-592 (2013).
35. Cho, S. W. et al. Analysis of off-target effects of CRISPR/Cas-derived RNA-guided endonucleases and nickases. Genome Res 24, 132-141 (2014).
36. Thoreen, C. C. et al. An ATP-competitive mammalian target of rapamycin inhibitor reveals rapamycin-resistant functions of mTORC1. J Biol Chem 284, 8023-8032 (2009).
37. Yoshimori, T., Yamamoto, A., Moriyama, Y., Futai, M. & Tashiro, Y. Bafilomycin Al, a specific inhibitor of vacuolar-type H(+)-ATPase, inhibits acidification and protein degradation in lysosomes of cultured cells. J Biol Chem 266, 17707-17712 (1991).
38. Malo, N., Hanley, J. A., Cerquozzi, S., Pelletier, J. & Nadon, R. Statistical practice in high-throughput screening data analysis. Nat Biotechnol 24, 167-175 (2006).
39. Kamada, Y. et al. Tor-mediated induction of autophagy via an Apgl protein kinase complex. J Cell Biol 150, 1507-1513 (2000).
40. Serra, V. et al. NVP-BEZ235, a Dual PI3K/mTOR Inhibitor, Prevents PI3K Signaling and Inhibits the Growth of Cancer Cells with Activating PI3K Mutations. Cancer Res 68, 8022-8030 (2008).
41. Li, L. et al. Autophagy Enhancer Carbamazepine Alleviates Memory Deficits and Cerebral Amyloid-β Pathology in a Mouse Model of Alzheimer's Disease. Curr Alzheimer Res 10, 433-441 (2013).
42. Renna, M., Jimenez-Sanchez, M., Sarkar, S. & Rubinsztein, D. C. Chemical Inducers of Autophagy That Enhance the Clearance of Mutant Proteins in Neurodegenerative Diseases. J Biol Chem 285, 11061-11067 (2010).
43. Berghauser Pont, L. M. E. et al. The HDAC Inhibitors Scriptaid and LBH589 Combined with the Oncolytic Virus Delta24-RGD Exert Enhanced Anti-Tumor Efficacy in Patient-Derived Glioblastoma Cells. PLoS ONE 10, e0127058-20 (2015).
44. Pajouhesh, H. & Lenz, G. R. Medicinal chemical properties of successful central nervous system drugs. NeuroRx 2, 541-553 (2005).
45. Wager, T. T., Hou, X., Verhoest, P. R. & Villalobos, A. Moving beyond Rules: The Development of a Central Nervous System Multiparameter Optimization (CNS MPO) Approach To Enable Alignment of Druglike Properties. ACS Chem. Neurosci. 1, 435-449 (2010).
46. Dixit, V. A. & Bharatam, P. V. SAR and Computer-Aided Drug Design Approaches in the Discovery of Peroxisome Proliferator-Activated Receptor yActivators: A Perspective. J Comput Med 2013, 1-38 (2013).
47. Mahé, P., Ueda, N., Akutsu, T., Perret, J.-L. & Vert, J.-P. Graph Kernels for Molecular Structure—Activity Relationship Analysis with Support Vector Machines. J. Chem. Inf. Model. 45, 939-951 (2005).
48. NIU, B., LU, W.-C., YANG, S.-S., CAI, Y.-D. & LI, G.-Z. Support vector machine for SAR/QSAR of phenethyl-amines. Acta Pharmacologica Sinica 28, 1075-1086 (2007).

The invention claimed is:

1. A method of monitoring autophagy in a human cell, the human cell engineered to express a fusion of a photoconvertable fluorescent protein (fcFP) and microtubule-associated proteins 1A/1B light chain 3B (LC3) from the MAP1LC3B locus of the human cell, the method comprising:
(a) exposing the human cell to an appropriate wavelength of light to photoconvert the fcFP; and
(b) monitoring a pre-conversion and/or a post-conversion emission wavelength of the fcFP over time, wherein time-dependent reduction in emission at the post-conversion emission wavelength correlates to autophagy flux of the human cell and time-dependent increase in emission at the pre-conversion wavelength correlates to activity of the autophagy pathway.

2. The method of claim 1, wherein the fcFP is an irreversible fcFP.

3. The method of claim 2, wherein the fcFP is selected from the group consisting of PAGFP, PS-CFP, PS-CFP2, PAmRFP1-1, PAmRFP1-2, PAmRFP1-3, PAmCherry1, PAmCherry 2, PAmCherry3, KFP, Kaede, mEosFP, mEos2, KikGR, mKikGR, and IrisFP.

4. The method of claim 1, wherein the autophagy biomarker is microtubule associated proteins 1A/1B light chain 3B (LC3) and the fcFP is Dendra2.

* * * * *